US010526573B2

(12) United States Patent
Ding et al.

(10) Patent No.: US 10,526,573 B2
(45) Date of Patent: Jan. 7, 2020

(54) DISRUPTION AND FIELD ENABLED DELIVERY OF COMPOUNDS AND COMPOSITIONS INTO CELLS

(71) Applicant: Massachusetts Institute of Technology, Cambridge, MA (US)

(72) Inventors: Xiaoyun Ding, Cambridge, MA (US); Armon R. Sharei, Watertown, MA (US); Robert S. Langer, Newton, MA (US); Klavs F. Jensen, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 30 days.

(21) Appl. No.: 15/526,517

(22) PCT Filed: Nov. 13, 2015

(86) PCT No.: PCT/US2015/060689
§ 371 (c)(1),
(2) Date: May 12, 2017

(87) PCT Pub. No.: WO2016/077761
PCT Pub. Date: May 19, 2016

(65) Prior Publication Data
US 2018/0016539 A1  Jan. 18, 2018

Related U.S. Application Data

(60) Provisional application No. 62/080,201, filed on Nov. 14, 2014, provisional application No. 62/239,241, filed on Oct. 8, 2015.

(51) Int. Cl.
| | |
|---|---|
| *C12N 13/00* | (2006.01) |
| *C12Q 1/68* | (2018.01) |
| *C12M 1/42* | (2006.01) |
| *C12N 15/87* | (2006.01) |
| *C12M 3/06* | (2006.01) |

(52) U.S. Cl.
CPC ............ *C12M 35/02* (2013.01); *C12M 23/16* (2013.01); *C12M 35/04* (2013.01); *C12N 13/00* (2013.01); *C12N 15/87* (2013.01)

(58) Field of Classification Search
None
See application file for complete search history.

(56) References Cited

U.S. PATENT DOCUMENTS

| | | | |
|---|---|---|---|
| 4,055,799 A | 10/1977 | Coster | |
| 4,835,457 A | 5/1989 | Hanss | |
| 5,023,054 A | 6/1991 | Sato et al. | |
| 5,643,577 A | 7/1997 | Pang et al. | |
| 5,658,892 A | 8/1997 | Flotte et al. | |
| 5,842,787 A | 12/1998 | Kopf-Sill et al. | |
| 5,951,976 A | 9/1999 | Segal | |
| 6,156,181 A | 12/2000 | Parce et al. | |
| 6,186,660 B1 | 2/2001 | Kopf-Sill et al. | |
| 6,218,166 B1 | 4/2001 | Ravindranath et al. | |
| 6,410,329 B1 | 6/2002 | Hansen et al. | |
| 6,461,867 B1 | 10/2002 | Cai et al. | |
| 6,562,616 B1 | 5/2003 | Toner et al. | |
| 7,109,034 B2 | 9/2006 | Ormar et al. | |
| 7,704,743 B2 | 4/2010 | Fedorov et al. | |
| 7,993,821 B2 | 8/2011 | Chiu et al. | |
| 8,211,656 B2 | 7/2012 | Hyde et al. | |
| 8,669,044 B2 | 3/2014 | Chiu et al. | |
| 8,844,570 B2 | 9/2014 | Glick et al. | |
| 9,005,579 B2 | 4/2015 | Nowinski et al. | |
| 9,017,991 B2 | 4/2015 | Diefenbach | |
| 9,157,550 B2 | 10/2015 | Wheeler et al. | |
| 9,255,245 B2 | 2/2016 | Bernick et al. | |
| 9,364,504 B2 | 6/2016 | Godfrin et al. | |
| 9,950,049 B2 | 4/2018 | Godfrin et al. | |
| 10,124,336 B2 | 11/2018 | Sharei et al. | |
| 2003/0133922 A1 | 7/2003 | Kasha, Jr. | |
| 2004/0176282 A1 | 9/2004 | Dalby et al. | |
| 2004/0197898 A1 | 10/2004 | Nakatani et al. | |
| 2005/0026283 A1 | 2/2005 | Ormar et al. | |
| 2006/0134067 A1 | 6/2006 | Liu et al. | |
| 2006/0134772 A1 | 6/2006 | Miles et al. | |
| 2006/0223185 A1 | 10/2006 | Fedorov et al. | |
| 2007/0243523 A1 | 10/2007 | Ionescu-Zanetti et al. | |
| 2007/0249038 A1 | 10/2007 | Adamo et al. | |
| 2008/0311140 A1 | 12/2008 | Lee et al. | |
| 2008/0318324 A1 | 12/2008 | Chiu et al. | |
| 2009/0209039 A1 | 9/2009 | Adamo et al. | |
| 2009/0280518 A1 | 11/2009 | Adamo et al. | |
| 2010/0203068 A1 | 8/2010 | Betz et al. | |
| 2010/0249621 A1 | 9/2010 | Ichitani | |
| 2010/0323388 A1 | 12/2010 | Chiu et al. | |
| 2011/0030808 A1 | 2/2011 | Chiou et al. | |
| 2011/0091973 A1 | 4/2011 | Glaser | |
| 2011/0300205 A1 | 12/2011 | Geall et al. | |
| 2012/0064505 A1 | 3/2012 | Suresh et al. | |
| 2012/0107925 A1 | 5/2012 | Li et al. | |
| 2012/0207745 A1 | 8/2012 | Godfrin et al. | |

(Continued)

FOREIGN PATENT DOCUMENTS

| | | |
|---|---|---|
| CN | 106244543 A | 12/2016 |
| EP | 882448 A1 | 12/1998 |

(Continued)

OTHER PUBLICATIONS

Adamo, Andrea et al., "Microfluidics-Based Assessment of Cell Deformability," Analytical Chemistry (Aug. 7, 2012), vol. 84, No. 15, pp. 6438-6443.

(Continued)

*Primary Examiner* — Channing S Mahatan
(74) *Attorney, Agent, or Firm* — Wolf, Greenfield & Sacks, P.C.

(57) ABSTRACT

A microfluidic system for causing perturbations in a cell membrane includes (a) a microfluidic channel defining a lumen and configured such that a cell suspended in a buffer can pass there through, and (b) source or emitter of an energy field. The microfluidic channel may include a cell-deforming constriction. A diameter of the constriction may be a function of the diameter of the cell. Related apparatus, systems, techniques, and articles are also described.

31 Claims, 25 Drawing Sheets

(56) References Cited

U.S. PATENT DOCUMENTS

| | | |
|---|---|---|
| 2013/0023051 A1 | 1/2013 | Bundock et al. |
| 2013/0045211 A1 | 2/2013 | Nowinski et al. |
| 2013/0065314 A1 | 3/2013 | Macmillan |
| 2014/0011226 A1 | 1/2014 | Bernick et al. |
| 2014/0273229 A1 | 9/2014 | Meacham et al. |
| 2014/0287509 A1 | 9/2014 | Sharei et al. |
| 2015/0184127 A1 | 7/2015 | White et al. |
| 2015/0196913 A1 | 7/2015 | Liu et al. |
| 2016/0017340 A1 | 1/2016 | Wu et al. |
| 2016/0193605 A1 | 7/2016 | Sharei et al. |
| 2016/0199837 A1 | 7/2016 | Breinlinger et al. |
| 2017/0020926 A1 | 1/2017 | Mata-Fink et al. |
| 2017/0326213 A1 | 11/2017 | Jajosky et al. |
| 2018/0003696 A1 | 1/2018 | Sharei et al. |
| 2018/0085402 A1 | 3/2018 | Kahvejian et al. |
| 2018/0142198 A1 | 5/2018 | Sharei et al. |
| 2018/0201889 A1 | 7/2018 | Sharei et al. |
| 2018/0245089 A1 | 8/2018 | Sharei et al. |

FOREIGN PATENT DOCUMENTS

| | | |
|---|---|---|
| EP | 1 225 228 A2 | 7/2002 |
| EP | 2 169 070 A1 | 3/2010 |
| JP | H01-196566 A | 8/1989 |
| JP | H01195655 A | 8/1989 |
| JP | H03257366 A | 11/1991 |
| JP | 2010-025852 A | 2/2010 |
| JP | 2011-163830 A | 8/2011 |
| JP | 6235085 B2 | 11/2017 |
| KR | 2014-0115560 A | 10/2014 |
| WO | WO 85/00748 A1 | 2/1985 |
| WO | WO 97/20570 A1 | 6/1997 |
| WO | WO 00/07630 A1 | 2/2000 |
| WO | WO 02/067863 A2 | 9/2002 |
| WO | WO 03/020039 A1 | 3/2003 |
| WO | WO 2004/001424 A1 | 12/2003 |
| WO | WO 2006/010521 A1 | 2/2006 |
| WO | WO 2006/095330 A2 | 9/2006 |
| WO | WO 2006/0105251 A2 | 10/2006 |
| WO | WO 2007/067032 A1 | 6/2007 |
| WO | WO 2007/097934 A2 | 8/2007 |
| WO | WO 2008/021465 A2 | 2/2008 |
| WO | WO 2009/056332 A1 | 5/2009 |
| WO | WO 2010/016800 A1 | 2/2010 |
| WO | WO 2010/077290 A1 | 7/2010 |
| WO | WO 2010/105135 A1 | 9/2010 |
| WO | WO 2010/129671 A2 | 11/2010 |
| WO | WO 2010/145849 A2 | 12/2010 |
| WO | WO 2011/051346 A1 | 5/2011 |
| WO | WO 2011/119492 A2 | 9/2011 |
| WO | WO 2012/097450 A1 | 7/2012 |
| WO | WO 2012/106536 A2 | 8/2012 |
| WO | WO 2012/118799 A2 | 9/2012 |
| WO | WO 2012/162779 A1 | 12/2012 |
| WO | WO 2013/059343 A1 | 4/2013 |
| WO | WO 2013/185032 A1 | 12/2013 |
| WO | WO 2014/106629 A1 | 7/2014 |
| WO | WO 2014/106631 A1 | 7/2014 |
| WO | WO 2014/120956 A1 | 8/2014 |
| WO | WO 2014/165707 A2 | 10/2014 |
| WO | WO 2015/023982 A1 | 2/2015 |
| WO | WO 2015/061458 A1 | 4/2015 |
| WO | WO 2015/153102 A1 | 10/2015 |
| WO | WO 2015/161276 A2 | 10/2015 |
| WO | WO 2016/003485 A1 | 1/2016 |
| WO | WO 2016/070136 A1 | 5/2016 |
| WO | WO 2016/077761 A1 | 5/2016 |
| WO | WO 2016/109864 A1 | 7/2016 |
| WO | WO 2016/115179 A1 | 7/2016 |
| WO | WO 2016/183482 A1 | 11/2016 |
| WO | WO 2017/005700 A1 | 1/2017 |
| WO | WO 2017/008063 A1 | 1/2017 |
| WO | WO 2017/041050 A1 | 3/2017 |
| WO | WO 2017/041051 A1 | 3/2017 |
| WO | WO 2017/106899 A2 | 6/2017 |
| WO | WO 2017/123644 A1 | 7/2017 |
| WO | WO 2017/123646 A1 | 7/2017 |
| WO | WO 2017/123663 A1 | 7/2017 |
| WO | WO 2017/192785 A1 | 11/2017 |
| WO | WO 2017/192786 A1 | 11/2017 |
| WO | WO 2018/089497 A1 | 5/2018 |

OTHER PUBLICATIONS

Augustsson et al. ""Microfluidic, Label-Free Enrichment of Prostate Cancer Cells in Blood Based on Acoustophoresis,"" Analytical Chemistry, Aug. 28, 2012 (Aug. 28, 2012), vol. 84, No. 18, pp. 7954-7962.

BD Bioscience FITC-labeled anti-CD45 antibody, 2 pages.

BD Bioscience PE-labeled anti-EpCAM antibody, 2 pages.

Boohaker, et al., "The Use of Therapeutic Peptides to Target and to Kill Cancer Cells," Curr. Med. Chem., 19(22), 26 pages, 2012.

Cancer Facts & Figures 2012. Published by the American Cancer Society in Atlanta, 68 pages.

Cross et al., "Nanomechanical analysis of cells from cancer patients," Nature Nanotechnology (Dec. 2007), vol. 2, pp. 780-783.

Downs, C. A. et al. (May 14, 2011). "Cell Culture Models Using Rat Primary Alveolar type 1 Cells", Pulmonary Pharm. & Therapeutics 24(5)577-586.

European Search Opinion dated Apr. 30, 2015 from European Application No. 12 841 329, 2 pp.

Extended European Search Report for EP 14836593.5, dated Feb. 23, 2017, 9 pages.

Gasteiger, et al., "Protein Identification and Analysis Tools on the ExPASy Server," The Proteomics Handbook, Chapter 52, pp. 571-607, 2005.

Griesbeck et al., "Sex Differences in Plasmacytoid Dendritic Cell Levels of IRF5 Drive higher IFN-alpha production in Women," The Journal of Immunology (Dec. 2015), vol. 195(11):5327-5336.

Hallow et al., "Shear-Induced Intracellular Loading of Cells With Molecules by Controlled Microfluidics," Biotechnology and Bioengineering (2008), vol. 99(4):846-854.

Han, X. et al., "CRISPR-Cas9 delivery to hard-to-transfect cells via membrane deformation," Sci. Adv., Aug. 14, 2015, e1500454, 8 pp.

Hillerdal, V. et al., "Systemic treatment with CAR-engineered T cells against PSCA delays subcutaneous tumor growth and prolongs survival of mice," BMC Cancer, vol. 14, No. 30, pp. 1-9 (Jan. 18, 2014).

Hoskin, et al., "Studies on anticancer activitied of antimicrobial peptides," Biochimica et Biophysica Acta, v.1778, pp. 357-375, 2008.

Hosokawa, et al., "Size-Selective Microacvity Array for Rapid and Efficient Detection of Circulation Tumor Cells," Anal. Chem, 85:6629-6635, 2010.

Howarth, M. et al. (May 2008). "Monovalent, Reduced-Size Quantum Dots for Imaging Receptors on Living Cells," Nature Methods 5(5):397-399.

Kim, D., et al., "Microengineered Platforms for Cell Mechanobiology," Annual Review of Biomedical Engineering, 2009, vol. 11, pp. 203-233.

Lee et al., "Nonendocytic delivery of functional engineered nanoparticles into the cytoplasm of live cells using a novel, high-throughput microfluidic device," Nano Letters (2012), vol. 12, pp. 6322-6327.

Lin et al., "Highly selective biomechanical separation of cancer cells from leukocytes using microfluidic ratchets and hydrodynamic concentrator," Biomicrofluidics (Jun. 26, 2013), vol. 7, No. 3, pp. 34114-1-11.

Liu et al., "Molecular imaging in tracking tumor-specific cytotoxic T lymphocytes (CTLs)," Theranostics (Jul. 28, 2014), vol. 4, No. 10, pp. 990-1001.

Liu et al., "Spatially selective reagent delivery into cancer cells using a two-layer microfluidic culture system," Analytica Chimica Acta (Sep. 1, 2012), vol. 743, pp. 125-130.

Liu, W. et al. (Jan. 20, 2010). "Compact Biocompatible Quantum Dots Via RAFT-Mediated Synthesis of Imidazole-Based Random Copolymer Ligand," JACS 132(2):472-483.

(56) References Cited

OTHER PUBLICATIONS

ATCC Thawing, Propagating, and Cryopreserving Protocol, NCI-PBCF-HTB81 (DU 145), Prostate Carcinoma (ATCC®htb-81), Version 1.6, 2012, 23 pages.
Certificate of Grant dated Jan. 11, 2018 for Chinese Application No. 201280060689.6.
Eixarch, H. et al. "Tolerance induction in experimental autoimmune encephalomyelitis using non-myeloablative hematopoietic gene therapy with autoantigen." Molecular Therapy 17.5 (2009): 897-905.
Esposito et al., "Intraerythrocytic administration of a synthetic Plasmodium antigen elicits antibody response in mice, without carrier molecules or adjuvants," International Journal of Parasitology, vol. 20, No. 8, pp. 1109-1111 (1990).
Examination Report No. 1 dated Dec. 1, 2016 from Australian Application No. 2012326203, 10 pages.
Examination Report No. 2 dated Jul. 26, 2017 from Australian Application No. 2012326203, 6 pages.
Hoeppener et al., "Immunomagnetic Separation Technologies," In: Ignatiadis M., Soritiou C., Pantel K. (eds.), Minimal Residual Disease and Circulating Tumor Cells in Breast Cancer. Recent Results in Cancer Research, vol. 195, pp. 43-58 (2012).
International Preliminary Report on Patentability dated Feb. 16, 2016 from International Application No. PCT/US2014/051343.
International Preliminary Report on Patentability, PCT/US2012/060646, dated Apr. 22, 2014, 7 pages.
International Preliminary Report on Pattentability, PCT/US2015/058489, dated May 2, 2017, 12 pages.
International Preliminary Report on Pattentability, PCT/US2015/060689, dated May 16, 2017, 10 pages.
International Search Report and Written Opinion dated Jan. 3, 2017 from International Application No. PCT/US2016/050287, 13 pages.
International Search Report and Written Opinion dated Jan. 12, 2016 from International Application No. PCT/US2016/050288, 14 pages.
International Search Report and Written Opinion dated Feb. 1, 2016 from International Application No. PCT/US15/60689.
International Search Report and Written Opinion dated Feb. 25, 2013 from International Application No. PCT/US12/060646.
International Search Report and Written Opinion dated Mar. 11, 2016 from International Application No. PCT/US15/584489.
International Search Report and Written Opinion dated Mar. 21, 2016 from International Application No. PCT/US2016/013113.
International Search Report and Written Opinion dated Jul. 21, 2017 from International Application No. PCT/US2017/030933, 20 pages.
International Search Report and Written Opinion dated Sep. 19, 2017 from International Application No. PCT/US2017/030932, 18 pages.
Janeway CA Jr, et al., "The structure of a typical antibody molecule," Immunobiology: The Immune System in Heath and Disease, 5th edition (2001), 5 pages.
Mattews, B.D., et al., "Cellular adaptation to mechanical stress: role of integrins, Rho, cytoskeletal tension and mechanosensitive ion channels," Journal of Cell Science, vol. 119, pp. 508-518, 2006.
Milo, R. "What is the total number of protein molecules per cell volume? A call to rethink some published values." Bioessays 35.12 (2013): 1050-1055.
Murphy, J. S. et al. (Sep. 1, 1956, e-pub May 2004). "Measurement of Wall Shearing Stress in the Boundary Layer by Means of an Evaporating Liquid Film," Journal of Applied Physics 27(9):1097-1103.
Notice of Grant dated Jan. 11, 2018 for Chinese Patent Application No. 201280060689.6.
Office Action dated Dec. 1, 2016 from Chinese Application No. 201280060689.6, 4 pages.
Office Action dated Dec. 17, 2014 from Chinese Office Action No. 201280060689.6, 9 pages.
Office Action dated Jul. 7, 2016 from Japanese Application No. 2014-537184, 14 pages.
Office Action dated Jun. 14, 2016 from European Application No. 12 841 329, 4 pages.
Office Action dated Jun. 23, 2017 from Chinese Application No. 201280060689.6, 4 pages.
Office Action dated May 13, 2016 from Chinese Application No. 201280060689.6, 4 pages.
Office Action dated Oct. 11, 2017 from European Application No. 12 841 329, 4 pages.
Office Action dated Sep. 6, 2015 from Chinese Office Action No. 201280060689.6, 8 pages.
Office Action dated Aug. 15, 2017 from U.S. Appl. No. 14/912,001, 32 pages.
Office Action dated Feb. 24, 2017 from U.S. Appl. No. 14/352,354, 11 pages.
Office Action dated Jul. 27, 2016 from U.S. Appl. No. 14/352,354, 9 pages.
Office Action dated Jul. 5, 2017 from Chinese Application No. 201480056295.2, 13 pages.
Office Action dated Mar. 16, 2017 from U.S. Appl. No. 14/912,001, 29 pages.
Office Action dated Mar. 23, 2017 from Russian Application No. 2014119926/10(031699), 10 pages.
Office Action dated May 1, 2017 from Japanese Application No. 2014-537184, 13 pages.
Office Action dated Oct. 26, 2016 from Russian Application No. 2014119926/10(031699), 10 pages.
Polvani et al., "Murine Red Blood Cells as Efficient Carriers of Three Bacterial Antigens for the Production of Specific and Neutralizing Antibodies," Biotechnology and Applied Biochemistry, vol. 14, pp. 347-356 (1991).
Ravilla et al., "Erythrocytes as Carrier for Drugs, Enzymes and Peptides," Journal of Applied Pharmaceutical Science, vol. 2, No. 2, pp. 166-176 (2012).
Rutella et al., "Tolerogenic dendritic cells: cytokine modulation comes of age," Blood, vol. 108, No. 5, pp. 1435-1440 (2006).
Sharei et al, "Ex vivo Cytosolic Delivery of Functional Macromolecules to Immune Cells," (Apr. 13, 2015), PLoS One, vol. 10, No. 4, 12 pp. e0118803.
Sharei et al., "A vector-free microfluidic platform for intracellular delivery," Proc. Natl. Acad. Sci. USA (Feb. 5, 2013), vol. 110, No. 6, pp. 2082-2087.
Sharei et al., "Cell Squeezing as a Robust, Microfluidic Intracellular Delivery Platform," Journal of Visualized Experiments (Nov. 7, 2013), No. 81, 7 pages.
Sharei et al., "Microfluidic Cell Deformation As a Robust, Vector-Free Method for Cystosolic Delivery of Macromolecules 2012 Annual Meeting," (Jan. 1, 2012), 3 pages.
Sharei et al., "Plasma membrane recovery kinetics of a microfluidic intracellular delivery platform," Integrative Biology (2014), vol. 6, pp. 470-475.
Shelby et al., "A microfluidic model for single-cell capillary obstruction by Plasmodium falciparum infected erythrocytes," (Dec. 9, 2003), Proc. Nat. Acad. Sci., vol. 100, No. 25, pp. 14618-14622.
Steinman et al., "Tolerogenic dendritic cells," Annual Review of Immunology, vol. 21, pp. 685-711 (2003).
Stewart et al., "In vitro and ex vivo strategies for intracellular delivery," Nature, vol. 538, No. 7624, pp. 183-192 (2016).
Supplementary European Search Report dated Apr. 21, 2015 from European Application No. 12 841 329, 3 pp.
Swaminathan, et al., "Mechanical Stiffness Grades Metastatic Potential in Patient Tumor Cells and in Cancer Cell Lines," Cancer Research, 71(15):5075-5080, 2011.
Szeto et al., "Microfluidic squeezing for intracellular antigen loading in polyclonal B-cells as cellular vaccines," Scientific Reports, vol. 5, 10276 (May 2015), 13 pages.
Third-Party Submission dated Oct. 23, 2015 from U.S. Appl. No. 14/352,354, 21 pages.
Williams, A.R. et al. (Nov. 5, 1999). "Filtroporation: A Simple, Reliable Technique for Transfection and Macromolecular Loading of Cells", Biotechnology and Bioengineering 65(3)341-346.
Zarnitsyn et al., "Electrosonic ejector microarray for drug and gene delivery," Biomed Microdevices (2008) 10:299-308.
Extended European Search Report for EP App. No. 16822078.8 dated Jan. 30, 2019.

(56) References Cited

OTHER PUBLICATIONS

International Search Report and Written Opinion for PCT/US2016/041653 dated Oct. 4, 2016.
International Preliminary Report on Patentability (Chapter I) for PCT/US2016/041653 dated Jan. 18, 2018.
Extended European Search Report for EP App. No. 16737769.6 dated May 3, 2018.
International Preliminary Report on Patentability (Chapter I) for PCT/US2016/013113 dated Jul. 27, 2017.
Partial Supplementary European Search Report for EP App. No. 15859824.3 dated Jun. 11, 2018.
Extended European Search Report for EP App. No. 15859824.3 dated Sep. 11, 2018.
Partial Supplementary European Search Report for EP App. No. 15855640.7 dated May 30, 2018.
Extended European Search Report for EP App. No. 15855640.7 dated Sep. 5, 2018.
International Search Report and Written Opinion for PCT/US2014/051343 dated Dec. 18, 2014.
Banz, A. et al., "Tumor Growth Control Using Red Blood Cells as the Antigen Delivery System and Poly(I:C)," J Immunother 2012, 35(5), pp. 409-417.
Chaw et al. Multi-step microfluidic device for studying cancer metastasis. Lab on a Chip (2007), v7, p. 1041-1047.
Cremel, L. et al., "Innovative approach in Pompe disease therapy: Induction of immune tolerance by antigen-encapsulated red blood cells," Int J Pharm. Aug. 1, 2015;491(1-2), pp. 69-77.
Cremel, L. et al., "Red blood cells as innovative antigen carrier to induce specific immune tolerance," Int J Pharm. Feb. 25, 2013;443(1-2), pp. 39-49.
Ding, X. et al., "High-throughput nuclear delivery and rapid expression of DNA via mechanical and electrical cell-membrane disruption," Nature Biomedical Engineering (2017), vol. 1, No. 3, 7 pages.
Ditommaso et al., Cell engineering with microfluidic squeezing preserves functionality of primary immune cells in vivo. PNAS. Oct. 2018;115(46):E10907-14.
Favretto, M. E. et al., "Human erythrocytes as drug carriers: Loading efficiency and side effects of hypotonic dialysis, chlorpromazine treatment and fusion with liposomes," Journal of Controlled Release 2013; 170: 343-351.
Gossett et al., Hydrodynamic stretching of single cells for large population mechanical phenotyping. PNAS. May 2012;109(20):7630-5.
Grimm, A. J. et al., "Memory of tolerance and induction of regulatory T cells by erythrocyte-targeted antigens," Sci Rep. Oct. 29, 2015;5:15907, 11 pages.
Kiani et al., Cas9 gRNA engineering for genome editing, activation and repression. Nature Methods. 2015;12:1051-4.
Li, J. et al., "Microfluidic-Enabled Intracellular Delivery of Membrane Impermeable Inhibitors to Study Target Engagement in Human Primary Cells," ACS Chemical Biology 2017, vol. 12, No. 12, pp. 2970-2974.
Lorentz, K. M. et al., "Engineered binding to erythrocytes induces immunological tolerance to E. coli asparaginase," Sci Adv. Jul. 17, 2015;1(6):e1500112, 10 pages.
Mali, P. et al., "RNA-guided human Genome Engineering via Cas9," Science (2013), vol. 339, No. 6121, pp. 823-826.
Maratou et al., Glucose transporter expression on the plasma membrane of resting and activated while blood cells. European Journal of Clinical Investigation. 2007;37:282-90.
Nic An Tsaoir et al., Scalable Antibody Production from CHO Cell Line of Choice Using Flow Electroporation. MaxCyte. Jun. 2016. 1 page.
Rossi, L. et al., "Erythrocyte-mediated delivery of phenylalanine ammonia lyase for the treatment of phenylketonuria in BTBR-Pah.sup.enu2 mice," Journal of Controlled Release 194; 37-44 (2014).
Rughetti, A. et al., "Transfected human dendritic cells to induce antitumor immunity," Gene Therapy, vol. 7, pp. 1458-1466 (2000).
Stevenson, D. J. et al., "Single cell optical transfection," J. R. Soc. Interface, vol. 7, 863-871 (2010).
Tlaxca, J. L. et al., "Analysis of in vitro Transfection by Sonoporation Using Cationic and Neutral Microbubbles," Ultrasound in Medicine and Biology, vol. 36, No. 11, 1907-1918 (2010).
Weaver et al., A brief overview of electroporation pulse strength-duration space: A region where additional intracellular effects are expected. Bioelectrochemistry. Oct. 2012;87:236-43.
Wright et al., Rational design of a split-Cas9 enzyme complex. PNAS. Mar. 2015;112(10):2984-9.
Yin et al., "Delivery technologies for genome editing," Nature Reviews (2017), vol. 16, No. 6, pp. 387-399.
Zdobnova et al., Self-Assembling Complexes of Quantum Dots and scFv Antibodies for Cancer Cell Targeting and Imaging. PLoS One. 2012;7(10):e48248. 8 pages.

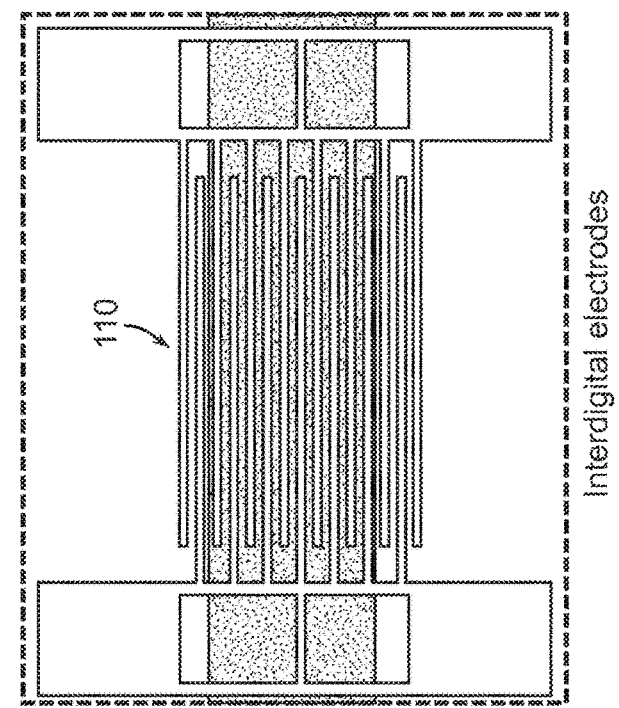
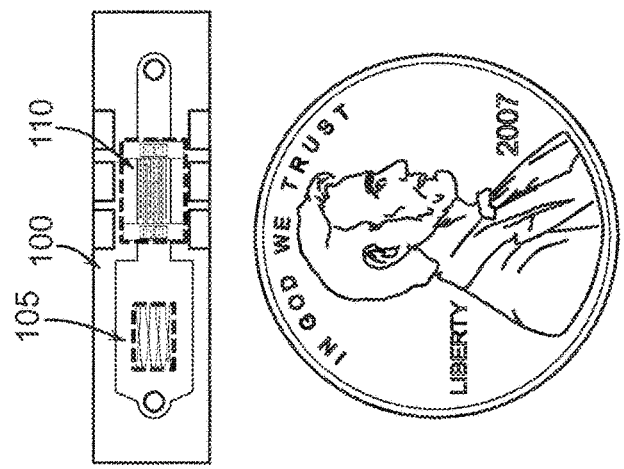
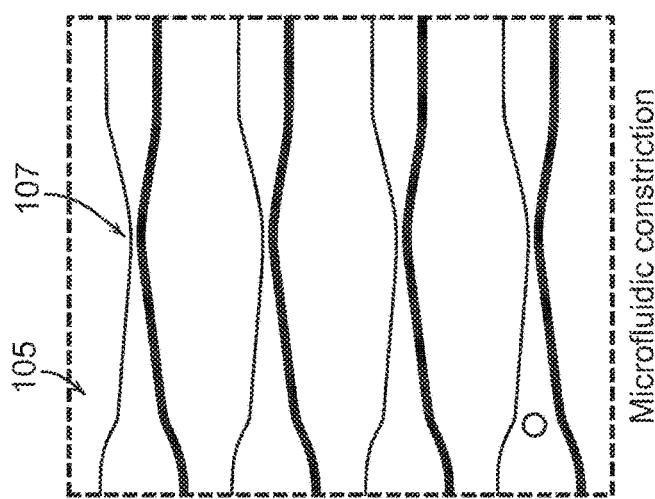
FIG. 1

DNA Diffusion=3 um2/s in water. mobility in free solution : 3-10e-8 m^2s/v.

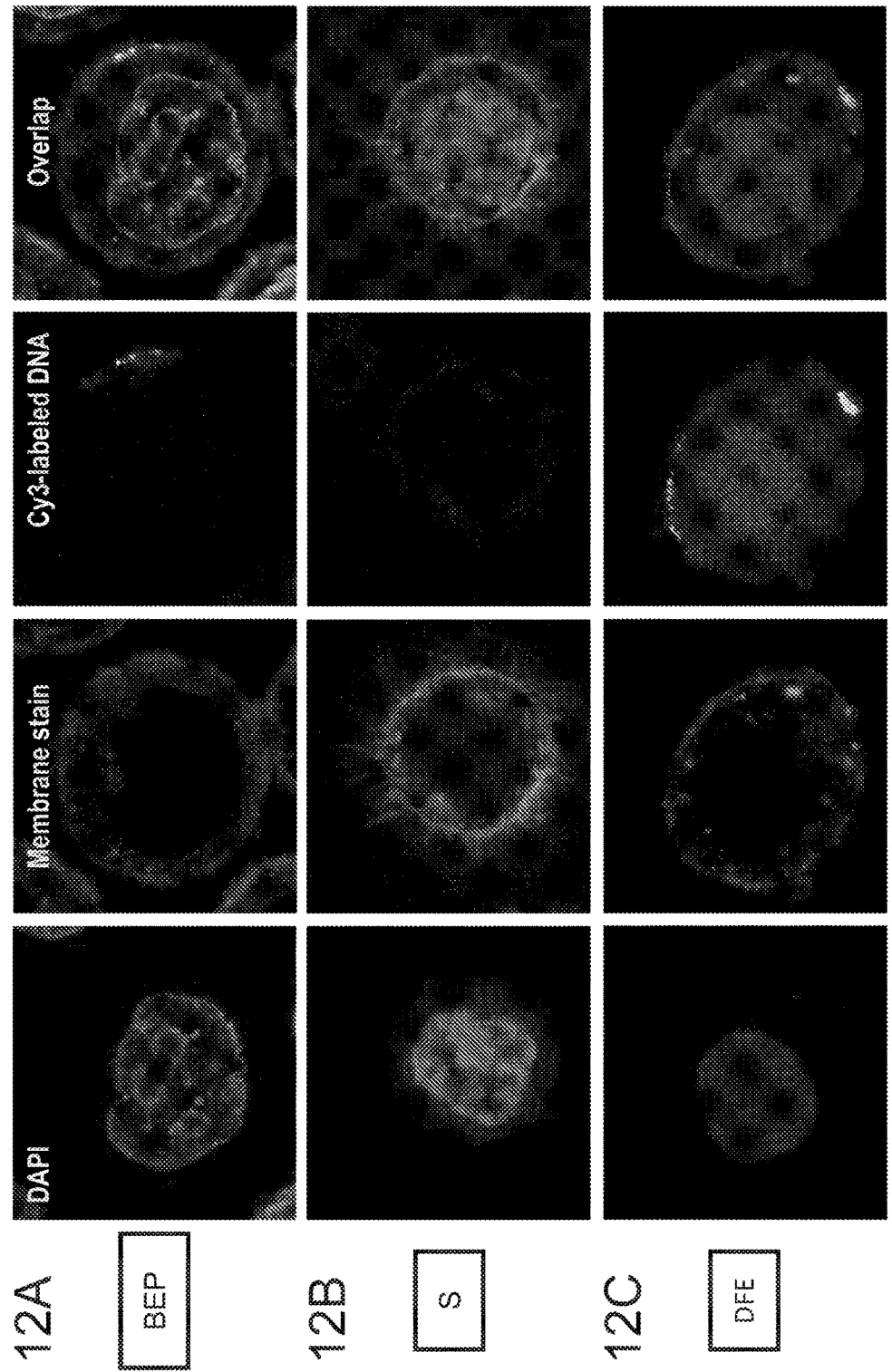

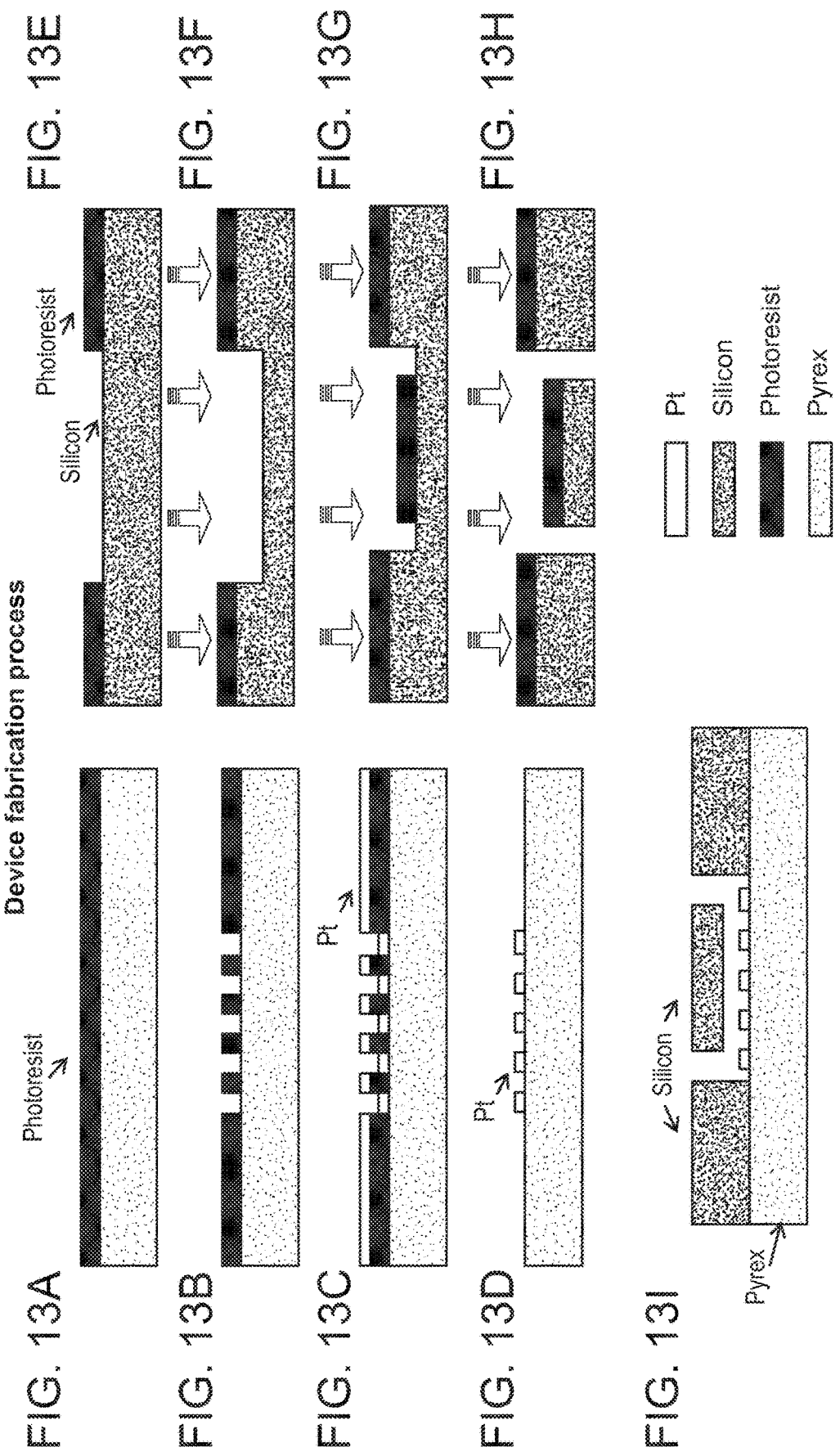

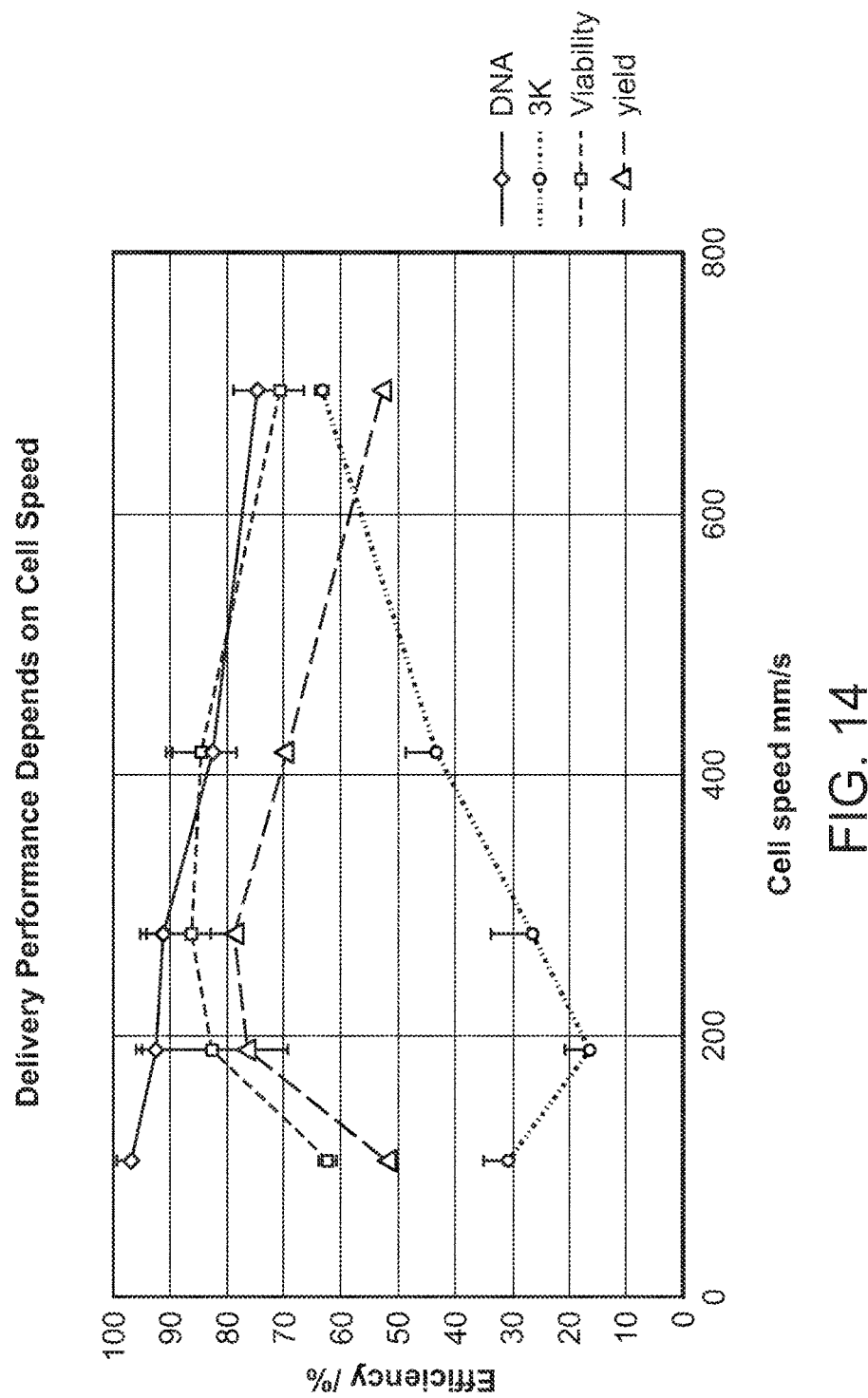

DISRUPTION AND FIELD ENABLED DELIVERY OF COMPOUNDS AND COMPOSITIONS INTO CELLS

RELATED APPLICATIONS

This application claims a priority benefit to PCT Application No. PCT/US2015/060689, filed Nov. 13 2015, which claims the benefit of priority under 35 U.S.C. § 119(e) to U.S. Provisional Application No: 62/239,241, filed Oct. 8, 2015, and U.S. Provisional Application No: 62/080,201, filed Nov. 14, 2014, which are incorporated herein by reference in their entireties.

STATEMENT AS TO FEDERALLY-SPONSORED RESEARCH

This invention was made with Government support under Grant No. R01 GM101420 awarded by the National Institutes of Health. The Government has certain rights in the invention.

FIELD OF THE INVENTION

The subject matter described herein relates to intracellular delivery of compounds or compositions.

BACKGROUND

Many pharmaceuticals largely focus on development of small-molecule drugs. These drugs are so-called due to their relatively small size that enables them to diffuse freely throughout the body to reach their target. These molecules are also capable of slipping across the otherwise impermeable cell membrane largely unhindered. The next generation of protein, DNA or RNA based therapies, however, cannot readily cross the cellular membrane and thus require cellular modification to facilitate delivery. Established methods use chemical or physical means to breach the membrane and deliver the material into the cytoplasm. Proper intracellular delivery is an important step in the research, development and implementation of the next generation of therapeutics.

In the electroporation process to deliver materials to a cell, DNA molecules accumulate and interact with the electropermeabilized plasma membrane during the electric pulse. Afterwards, those DNA aggregates are internalized into the cytoplasm and subsequently lead to gene expression (Golzio, M. et al., *Proc. Natl. Acad. Sci.* 99, 1292-1297 (2002); Paganin-Gioanni, A. et al. *Proc. Natl. Acad. Sci. U.S.A.* 108, 10443-7 (2011); Rosazza, C. et al., *Mol. Ther.* 21, 2217-2226 (2013); Boukany, P. E. et al. *Nat. Nanotechnol.* 6, 747-54 (2011); Teissie, J. et al., *Biochim. Biophys. Acta* 1724, 270-80 (2005); Yannush, M. L. et al., *Annu. Rev. Biomed. Eng.* 16, 295-320 (2014); Geng, T. & Lu, C., *Lab Chip* 13, 3803-21 (2013)). It is unlikely that DNA plasmids could navigate through the viscous and crowded cytoplasm to reach the nucleus simply by diffusion (Lechardeur, D. et al., *Adv. Drug Deliv. Rev.* 57, 755-767 (2005); Dowty, M. E. et al., *Proc. Natl. Acad. Sci. U.S.A.* 92, 4572-4576 (1995)). Some work has shown that the transportation of DNA from plasma membrane to nucleus is an active biological process through cytoskeletal transport such as via microtubule and actin networks (Rosazza, C. et al., *Mol. Ther.* 21, 2217-2226 (2013)). It has been found that microtubule and actin networks play an important role in DNA transportation within the cytoplasm, and the time-scale of such processes can be hours long depending on the cell type. The unclear mechanism and complex nature of DNA transfer between the plasma membrane and nucleus hinders the enhancement of electroporation performance in hard-to-transfect cells. Moreover, the strong fields used in current electroporation techniques can lead to significant damage or death (Yarmush, M. L. et al., *Annu. Rev. Biomed. Eng.* 16, 295-320 (2014); Geng, T. & Lu, C., *Lab Chip* 13, 3803-21 (2013)). Technologies that can directly send payloads into cells and cell organelles are needed.

SUMMARY OF THE INVENTION

The invention provides a solution to problems and drawbacks associated with earlier methods of delivering compounds and/or mixtures of compounds to the cytosol and sub-cellular organelles, such as the nucleus of a cell. Aspects of the present invention provide a microfluidic system for causing perturbations in a cell membrane that includes a microfluidic channel defining a lumen and configured such that a cell suspended in a buffer can pass through the lumen. The systems and methods are useful to deliver cargo such as macromolecules, such as DNA, RNA, proteins, peptides, sugar polymers, nanomaterials, as well as small molecules through the cell membrane and into the cell, e.g., a eukaryotic or prokaryotic cell. The microfluidic channel includes a cell-deforming constriction. A diameter of the constriction may be a function of the diameter of the cell and is no greater than the diameter of the cell. Downstream of the constriction, the microfluidic channel comprises a source or emitter of an energy field. In various embodiments, the microfluidic system includes an electrode(s) to generate an electric field, a magnet or electromagnet to generate a magnetic field, a source of sound to generate an acoustic field, and/or a source of light. In some embodiments, the energy source comprises interdigital electrodes. The combination of cell-deforming constriction and subsequent exposure of a cell to an energy field such as those described above leads to a synergistic effect in the delivery of cargo molecules into the cells and/or translocation of cargo molecules inside the cell to subcellular structures such as the nucleus or mitochondria. The exposure of a cell to at least two dissimilar forces, e.g., a physical constrictive force and an electrical force, leads to surprising advantages in efficiency of delivery and activity of delivered cargo, e.g., expression of encoded proteins by delivered nucleic acids.

In some embodiments, at least one electrode, magnet, acoustic device, or light source is in proximity to the cell-deforming constriction, e.g., in series, and generates a field. For example, one or more electrodes, magnets, acoustic devices, or light sources are positioned upstream, downstream or to deliver an electrical, magnetic, or acoustic signal simultaneously to a cell relative to a position of a constriction. For example, cells are exposed to an electric, magnetic, acoustic, or optical field after a cell-deforming constriction event.

In certain embodiments, the field or field emitter/source and the microfluidic channel are part of a single device of a system. Alternatively, the microfluidic system may have a first device and a second device, where the microfluidic channel is part of the first device and the emitter/source is within the second device of a system. The field exposure occurs when a cell is inside the first device or outside the original (first) device. In some embodiments, the microfluidic system may have a first device and a second device, where the microfluidic channel is part of the one device (a first device) and the source/emitter is within another device (a second, third, or additional device) such that the energy field is emitted from the device with the source/emitter through the device having the microfluidic channel.

In certain embodiments, a magnet (such as an electromagnet), acoustic device, or light source/emitter and a microfluidic channel are part of a single device of a system. For example, the magnet or acoustic device may be downstream of the cell-deforming constriction in the microfluidic channel. In other embodiments in which the microfluidic system has a first device and a second device, the microfluidic channel is part of the first device and the magnet, acoustic device, or light source/emitter is within the second device of a system. The field exposure occurs when a cell is inside the first device or outside the original (first) device. In some embodiments, the microfluidic system may have a first device and a second device, where the microfluidic channel is part of the one device (a first device) and the magnet, acoustic device of the light source/emitter is within another device (a second, third, or additional device) such that the energy field is emitted from the device with the electrode(s) through the device having the microfluidic channel.

In certain embodiments, the electrode or electrodes and the microfluidic channel are part of a single device of a system. Alternatively, the microfluidic system may have a first device and a second device, where the microfluidic channel is part of the first device and the electrode(s) is within the second device of a system. The field exposure occurs when a cell is inside the first device or outside the original (first) device of the system. In some embodiments, the microfluidic system may have a first device and a second device, where the microfluidic channel is part of the one device (a first device) and the electrode(s) is within another device (a second, third, or additional device) such that the electric field is emitted from the device with the electrode(s) through the device having the microfluidic channel.

In some embodiments in which the at least one electrode, magnet, acoustic device, or light and the microfluidic channel are part of a single device, the at least one electrode, magnet, acoustic device, or light may be downstream of the cell-deforming constriction.

In various implementations of the invention, the diameter of the constriction is selected to induce temporary perturbations of the cell membrane large enough for a payload to pass through, and the cell passes through the constriction to a field (i.e., an electric, magnetic, acoustic, or optical field) in a continuous flow. After passing through the constriction, the cell may contact or pass through a portion of the field whose strength is sufficient to drive a payload though a temporary perturbation. In other embodiments, the cell enters into and remains within a zone or chamber of the device that is downstream of the constriction after passing through the constriction. Cells within this zone or chamber are then contacted with the field.

Aspects of the invention also relate to methods for delivering a compound or composition into a cell. Methods may, e.g., include providing a cell in a payload containing solution, passing the solution through a microfluidic channel that includes a cell-deforming constriction, passing the cell through the constriction such that a pressure is applied to the cell causing perturbations of the cell membrane large enough for a payload to pass through, and passing a cell through or contacting the cell with an electric field, a magnetic field, an acoustic field, or an optical field that further drives the payload into the cell and/or translocates the payload from a first location, e.g., the cell membrane to another or second location, e.g., the nucleus or other subcellular organelle or structure (such as a mitochondrion), within the cell. For example, the first location comprises a cytosolic location or an area at or near the cytosol/plasma membrane interface and the second location comprises a mitochondrial or nuclear location. In some embodiments, the cells are processed in accordance with a temporal sequence: the cells are first disrupted (e.g., squeezed, deformed, or compressed), followed by exposure to an applied energy field, e.g., an electric, magnetic, or acoustic field.

In some embodiments, the payload may be added to a cell-containing solution after the cell is disrupted and before or while the cell is contacted with or passes through a portion of a field (such as an electric, magnetic, or acoustic field) that further drives the payload into the cell and/or translocates the payload from a first location, e.g., the cell membrane to another or second location, e.g., the nucleus or other subcellular organelle or structure (such as a mitochondrion), within the cell.

In certain embodiments relating to a polypeptide payload, the polypeptide may include a localization signal. In some embodiments, the polypeptide payload is a fusion-protein that comprises a localization signal. For example, the polypeptide may comprise an endoplasmic reticulum-retention signal, a nuclear localization signal, a nucleolar localization signal, a mitochondrial targeting signal, or a peroxisome targeting signal. Such signals are known in the art, and non-limiting examples are described in Kalderon et al., (1984) *Cell* 39 (3 Pt 2): 499-509; Makkerh et al., (1996) *Curr Biol.* 6 (8): 1025-7; Dingwall et al., (1991) *Trends in Biochemical Sciences* 16 (12): 478-81; Scott et al., (2011) *BMC Bioinformatics* 12:317 (7 pages); Omura T (1998) *J Biochem.* 123(6):1010-6; Rapaport D (2003) *EMBO Rep.* 4(10):948-52; and Brocard & Hartig (2006) *Biochimica et Biophysica Acta (BBA)—Molecular Cell Research* 1763 (12):1565-1573, the contents of each of which are hereby incorporated herein by reference.

In embodiments relating to an electric field, the electric field may be generated by at least one electrode or a set of two electrodes on either side of a microfluidic channel or zone/chamber. In embodiments relating to a magnetic field, the magnetic field may be generated by at least one magnet. Non-limiting examples of magnets useful in various embodiments relating to magnetic fields are temporary magnets, permanent magnets, and electromagnets. In embodiments relating to an acoustic field, the acoustic field may be generated by at least one acoustic device. A non-limiting example of an acoustic device is a speaker. In embodiments relating to an optical field, the optical field may be generated by any light-emitting device or ambient light may be used. Non-limiting examples of light-emitting devices include light-emitting diodes (LEDs), lasers, incandescent lightbulbs, or other sources of visible electromagnetic radiation.

In various implementations of the invention, a cell is passed through a microfluidic channel in a first device and then removed from the first device and contacted with the electric field, the magnetic field, or the acoustic field in a second device. In other implementations, the microfluidic channel and the electric field, the magnetic field, and the acoustic field are within one device. For example, the cell may pass through a constriction to the field in a continuous flow, and after passing through said constriction the cell contacts or passes through a portion of the field whose strength is sufficient to drive a payload though a temporary perturbation. Alternatively, after passing through the constriction, the cell may flow into and remain within a zone of the device where the cell is contacted with the field.

The microfluidic system may include a plurality of microfluidic channels. Each of the microfluidic channels of the plurality defines a lumen and is configured such that a cell suspended in a buffer can pass through the lumen. Additionally, each microfluidic channel includes one or more cell-deforming constrictions. In some embodiments, the diameter of the constriction is a function of the diameter of the cell. Thus, there may be many microfluidic channels within a microfluidic system of the invention. For example, the microfluidic system may include a plurality of the microfluidic channels arranged in parallel, e.g., 2, 5, 10, 20, 40, 45, 50, 75, 100, 500, 1,000 or more.

Microfluidic systems having a plurality of parallel microfluidic channels allow for the high-throughput delivery of payloads to cells. Many cells can be passed through each parallel channel one after the other. The cells may be exposed to an electric, magnetic or acoustic field either during or after passing through the microfluidic channels. With multiple cells passing through each of the microfluidic channels, a large number of cells can be treated in a short amount of time. It will be understood that, depending on context, a reference to a "cell" herein may refer to more than one cell. In preferred embodiments, the electric, magnetic or acoustic field is applied to cells downstream of the cell-deforming constriction, i.e., cells pass through the constriction thereby deforming/destabilizing the cell membrane and allowing payload to enter the cells. Subsequent to that event, the cells are subjected to an electric, magnetic, or acoustic field. The electric, magnetic, or acoustic field mediates translocation of payload inside the cell (such payload having entered the cell cytoplasm as a result of the previous constricting step) to subcellular structures inside the cell, e.g., the nucleus.

In preferred aspects of the invention, the diameter of the constriction is selected to induce temporary perturbations of the cell membrane large enough for a payload to pass through. It will be understood that the diameter of the constriction may be adjusted based on the cell-type and payload used.

Multiple variations regarding the placement of electrodes, magnets or acoustic devices are possible. In preferred embodiments, the electrodes are placed on only one end of the cell-deforming constriction. In other embodiments, the electrodes are placed on both ends, e.g., at the cellular entrance and the exit ends of the cell-deforming constriction. The that microfluidic systems may include two or more electrodes that generate an electric field to drive or push nucleic acids into the cell suspended in the buffer, or into the nucleus of the cell. For example, the electric field destabilizes the membrane of the nucleus or other sub-cellular organelle, e.g., a mitochondrion, thereby facilitating entry of the cargo into the sub-cellular structure.

In some embodiments, the strength of the electric field is less than would be required to electroporate the cell, e.g., introduce nucleic acids across the plasma membrane of the cell. For example, a lower strength electric field may be used in DFE to obtain the same level of delivery for a given payload for a particular cell type. Unlike electroporation, which requires a field of sufficient strength to disrupt the cell membrane and drive materials towards the cytosol, this manifestation provides membrane disruption by mechanical deformation and utilizes the driving force of the field to enhance translocation of material into the cell cytosol and subcellular compartments. By eliminating the use of electrical energy as the sole source for disruption of the cell membrane and/or embedding of material into the plasma membrane by field driven forces, DFE allows for the use of lower field strengths capable of directly delivering material into the cytosol and subcellular compartments across a mechanically compromised membrane. In the same and other embodiments, the combination of the constriction and the electric field increases the efficiency of nucleic acid delivery to the nucleus of the cell. In some embodiments, the electric field may enhance the permeability of membranes. For example, the electric field may enhance permeability of subcellular membranes that may not be directly disrupted by the mechanical component. Without being bound by theory, mechanical disruption of the outer membrane may expose internal membranes to field effects due to the absence of an uncompromised outer membrane. In preferred aspects of the invention, the viability of cells that pass through the microfluidic system and receive the payload is higher than corresponding cells that are treated with electroporation. For example, substantially or about 1-50%, 1-10%, or about 5, 10, 15, 20, 25, 30, 35, 40, 40, 50, 60, 70, or 80% more of the cells that pass through the microfluidic system are viable compared to a population of corresponding cells that are treated with standard electroporation conditions alone.

The microfluidic system may comprise a plurality of electrode pairs in which electrode size varies between electrode pairs (FIG. 2). In a non-limiting example, the plurality of electrode pairs is configured into at least a first and a second array of electrode pairs, and the first array of electrode pairs is offset from the second array of electrode pairs. In some embodiments, the microfluidic system comprises a plurality of electrodes that are configured into at least a first and a second array of electrodes. The first array of electrodes may be offset from the second array of electrodes. It will be understood that there are a variety of ways (e.g., by various degrees oriented on the X, Y, and/or Z planes) that different arrays of electrodes or electrode pairs may be offset from each other. For example, the first array may be offset at an angle of substantially or about 1°, 50°, 10°, 15°, 20°, 25°, 30°, 35°, 40°, 45°, 50°, 60°, 70°, 80°, 90°, 1-10°, 1-20°, 1-30°, 1-45°, or 1-90° in a horizontal, vertical, or diagonal plane from the second array.

Many different exposure times of the cell to the electric field are possible. For example, and in preferred embodiments, the exposure time is substantially or about 10-50 ms, 50-100 ms or 10-100 ms. Aspects of the present invention include electric fields that are substantially constant between two or more electrodes. In some embodiments, the electric field is a constant or pulsed direct electric current. Preferably, the electric field is pulsed. In some embodiments, the electric field is pulsed at about 50-200 µs. The strength of the electric field may also vary. In some embodiments, the strength or the pulse strength of the electric field may be substantially or about 1-3 kV/cm or 0.1 to 0.5, 0.1 to 1, 0.1 to 1.5, 0.1 to 2, 0.1 to 2.5, or 0.1 to 3 kV/cm. In some embodiments, the strength or the pulse strength of the electric field may be substantially or about 0.1, 0.2, 0.3, 0.4, 0.5, 0.6, 0.7, 0.8, 0.9, 1, 1.5, 2, or 2.5 kV/cm. The field strength can be in the range of 0.1-10 kV/cm or even wider depending on the specific case. For example, the strength or the pulse strength of the electric field is substantially or about 0.1-20 kV/cm, or less than 1 kV/cm. In various embodiments, the strength or the pulse strength of the electric field is substantially or about 10-20 kV/cm, or less than 1 kV/cm. In some implementations of the invention, the electric field is pulsed at a duration of substantially or about 0.1, 0.1-2, or 0.1-2000 ms, at a period of 1-20, 0.1-2000, or 1-200 ms. In some instances, strength or pulse strength of the electric field may be less than the strength necessary to electroporate the cell. For example, the strength or pulse strength of the electric field may be substantially or about 50, 1-50, 50-99, or 1-99% less than the strength necessary to electroporate the cell.

In some embodiments, the electric field is generated using a direct current. In other embodiments, the electric field is generated using an alternating current. The alternating current may oscillate evenly, or may have asymmetric oscillation such that there is a net direct for the force of the electric field. Asymmetric oscillation may be achieved, for example, by applying an alternating current having a non-zero bias.

In some implementations, the current subject matter combines the advantages of viral vector-free delivery by rapid mechanical cell deformation that causes temporary perturbations with electrical fields that help deliver payloads such as DNA through the perturbations and into the cell with high-efficiency. In some implementations, the current subject matter utilizes electric fields at lower intensities than some traditional electroporation techniques yet higher intensities than some sensing applications, which, for example, may sense cell resistivity. An exemplary sensing approach is described in U.S. Patent Application Publication No. 2009/0280518, published Nov. 12, 2009 (Adamo et al.). Thus, for a fixed delivery efficiency, some embodiments use a lower electric field intensity electroporation. Delivery and expression of nucleic acids may also be achieved faster. The faster delivery and expression of nucleic acids provides important advantages for DNA expression compared to electroporation alone or cell squeeze without a field. There are also profound advantages to delivering other charged payloads (such as RNA) using DFE. For example, more RNA may be delivered into a given cell using the DFE technique compared to electroporation or cell squeeze without a field.

Electric and magnetic fields are particularly useful for driving charged payloads into cells and subcellular compartments (such as into organelles). Payloads may be modified to optionally increase the charge thereof resulting in improved delivery by DFE. In some embodiments, a payload with a low or no charge is modified to increase its delivery using an electric or magnetic field. For example, a protein may be conjugated to a charged compound, preferably using a covalent bond. The conjugation may be, e.g., at the N- or C-terminal end (e.g., via a peptide bond) or at an amino acid sidechain (e.g., via a disulfide bond with a cysteine or a bond with a selenocysteine). This approach is not limited to proteins, and may be applied to various payloads disclosed herein.

In some embodiments, the conjugation is via a disulfide bond or another bond that is readily cleaved in cells. Examples of charged compounds that may be conjugated to a payload include single charged amino acids (i.e., an amino acid monomer having a charge) and/or stretches of multiple charged amino acids. In some embodiments, a stretch of charged amino acids comprises a mixture of different amino acids having a positive charge. In other embodiments, a stretch of charged amino acids comprises a mixture of different amino acids having a negative charge. Alternatively, the stretch of charged amino acids has a repeat of the same amino acid. The amino acids may be natural, non-natural, or a combination thereof. The length of the stretch may vary depending on the size of the payload to be modified and the desired charge to be added to the payload. In various embodiments, the stretch of amino acids comprises about 1, 2, 3, 4, 5, 6, 7, 8, 9, 10, 15, 20, 25, 30, 35, 40, 45, 50, or 1-50, amino acids.

Examples of naturally occurring positively charged amino acids include arginine, histidine, and lysine. Examples of naturally occurring negatively charged amino acids include aspartic acid and glutamic acid. Examples of non-naturally occurring amino acids include those with a positive charge such as D stereoisomers of arginine, histidine, and lysine, and those with a negative charge such as D stereoisomers of aspartic acid and glutamic acid. Thus, a payload may be modified to have increased positive charge using, e.g., one or more or any combination of naturally occurring amino acids such as arginine, histidine, and lysine and/or non-naturally amino acids such as D stereoisomers of arginine, histidine, and lysine. Alternatively, a payload may be modified to have increased negative charge using, e.g., one or more or any combination of naturally occurring amino acids such as aspartic acid and glutamic acid and/or non-naturally occurring amino acids such as D stereoisomers of aspartic acid and glutamic acid.

In some embodiments, the pH of a buffer or solution is adjusted to increase the charge of a payload. For example, the pH may be below or above the isoelectric point (pH(I)) of the payload. The payload will have a net positive chart at a pH below a payload's pH(I) and a net negative charge at a pH above its pH(I).

Implementations of the invention may also provide one or more of the following features. Deforming the cell includes deforming the cell for substantially or about 1 µs to 10 ms, e.g., 10 µs, 50 µs, 100 µs, 500 µs, and 750 µs. Incubating occurs for 0.0001 seconds to 20 minutes, e.g., substantially or about 1 second, 30 seconds, 90 seconds, 270 seconds, and 900 seconds.

The pressure and speeds at which a cell is passed through a microfluidic channel may also vary. In some embodiments, a pressure of substantially or about 10-35 psi is used to pass the solution containing a cell through a microfluidic channel. The speed may be adjusted for a variety of reasons, including to improve viability of the treated cells while maintaining high payload delivery. In preferred embodiments, the cell passes through the microfluidic channel at a speed of substantially or about 300 mm/s, 100-300 mm/s, 200-700 mm/s, 250-400 mm/s, 1-1000 mm/s, 1 m/s, 2 m/s, 3 m/s, 4 m/s, 5 m/s, 6 m/s, 7 m/s, 8 m/s, 9 m/s, 10 m/s, 0.01-5 m/s, 5-10 m/s, or 0.01-10 m/s. In some embodiments, the cell passes through the electric field at a speed of substantially or about 100, 170, 300, 100-300, 200-700, 250-400, 100-1000 mm/s, or 1-1000 mm/s. Where the cell is a plurality of cells, substantially or about 80, 85, 90, 91, 92, 93, 94, 95, 96, 97, 98, 99, 90-95, or 80-100% of the cells may be viable after passing through the constriction and the electric field.

In some embodiments, the cell is contacted with the electric field at a speed of 0 m/s. For example, the field may pass through a zone, area, or reservoir of a device where the cell is contacted with the electric field. The field may be on for an amount of time before switching off. In such cases, cells are not passing through the field, but the field exposure is still temporary.

The size and duration of temporary perturbations in cell membranes can be modified by adjusting various factors, such as the diameter of cell-deforming constrictions and the speed at which cells pass through the constrictions. Disclosures regarding the size and duration of perturbations provided herein should not be interpreted as limiting. Non-limiting descriptions of perturbations and recovery are provided in Sharei et al., (2014) *Integr. Biol.*, 6, 470-475, the entire content of which is incorporated herein by reference. In some embodiments, the perturbations of the cell membrane may be characterized by a maximum diameter of substantially or about 1-20, 1-600, 4, 5, 6, 7, 8, 9, 10, 12, 14, 16, 18, 20, 25, 50, 75, 100, 150, 200, 250, 300, 350, 400, 450, 500, or 600 nm. In various embodiments, perturbations of the cell membrane having a maximum diameter of substantially or about 1-20, 1-600, 4, 5, 6, 7, 8, 9, 10, 12, 14, 16, 18, 20, 25, 50, 75, 100, 150, 200, 250, 300, 350, 400, 450, 500, or 600 nm persist on the cell membrane for at least substantially or about 1, 2, 3, 4, 5, 6, 7, 8, 9, 10, or 1-10 minutes or more (11, 13, 15, 18, 20 minutes or more).

In some embodiments, the cell may be primarily compressed by the fluid flow. In some embodiments, the diameter is less than the diameter of the cell. For example, the diameter of the constriction may be substantially or about 20, 25, 30, 35, 40, 45, 50, 55, 60, 65, 70, 75, 80, 85, 90, 95, or 20-99% of the diameter of the cell. Non-limiting examples of the diameter of the constriction include substantially or about 4, 5, 6, 7, 8, 9, 10, 15, 20 4-10 µm, or 10-20 µm. Different lengths of the constriction are also possible. Non-limiting examples of constriction lengths include substantially or about 10, 15, 20, 24, 30, 40, 50, 60, 10-40, 10-50, 10-60, or 10-40 µm.

Many cells are between 5-20 µm in diameter, e.g. naïve T cells are 7-8 µm in diameter. For example, the diameter of the constriction portion is 4.5, 5, 5.5, 6, or 6.5 µm for processing of single cells. In another example, the size/diameter of the constricted portion for processing of a human egg is between 60 µm and 80 µm, although larger and smaller constrictions are possible (diameter of a human ovum is approximately 100 µm). In yet another example, embryos (e.g., clusters of 2-3 cells) are processed using a constriction diameter of between 12 µm and 17 µm. In a non-limiting example relating to naïve T and B cells, the device comprises a constriction having a length of about 10, 15, 20, 25, 30, or 10-30 µm, a width of about 3, 3.5, 4, or 3-4 µm, a depth of about 15, 20, 25, or 15-25 µm, and/or an about 5, 6, 7, 8, 9, 10, 11, 12, 13, 14, 15, or 5-15 degree angle. Examples of microfluidic devices useful for delivering payloads into immune cells are described in PCT International Patent Application No. PCT/US2015/058489, Delivery of Biomolecules to Immune Cells, filed Oct. 30, 2015, the entire contents of which are incorporated herein by reference.

The device and methods are useful in vaccine development and production using professional antigen presenting cells such as dendritic cells. For example, a method of stimulating antigen presentation is carried out by subjecting a dendritic cell to a controlled injury such as transitory constriction or pulse of high shear and contacting the dendritic cell with a solution comprising a target antigen. The method yields highly activated antigen presenting cells compared to previous methods of stimulation. Vaccine production is carried out by propelling dendritic cells or other antigen presenting cells through the constriction-containing device (thereby subjecting the cells to a rapid stretching event) and then incubating the cells in a solution containing the payload, e.g., antigen. The cells are bathed in a cell culture medium containing one or more antigens (or a nucleic acid encoding one or more antigens) after rapid deformation of the cells, but the cells may be contacted with the antigen prior to, during, and/or after the rapid deformation event/process. In some embodiments, DFE is used to deliver a nucleic acid, such as an mRNA or a DNA, which encodes an antigen or other gene product such that the gene product is produced in the cell. DFE may also be used to deliver DNA into cells for the generation of CAR-T cells.

For example, a construct encoding a chimeric antigen receptor (CAR) may be delivered to a T cell using DFE. In some embodiments, the CAR is a fusion of an extracellular recognition domain (e.g., an antigen-binding domain), a transmembrane domain, and one or more intracellular signaling domains.

In some embodiments, the compound is a nucleic acid encoding for a MHC complex. In some embodiments, the compound is a nucleic acid encoding for a MHC class I or MI-IC class II complex. In some embodiments, the nucleic acid encodes for a chimeric antigen receptor, such as a chimeric T cell receptor. In some embodiments, the nucleic acid encodes for a recombinant T cell receptor. For example, nucleic acids encoding chimeric antigen receptors are introduced into a T cell in a virus-free way, i.e., by cell squeezing, to maintain expression of CAR-T. For example, introduction of DNA is accomplished without the use of a viral particle. Nucleic acid constructs, e.g., a plasmid, may however include viral genome elements, which may help the integration or be maintained as an extrachromosomal nucleic acid.

In some embodiments relating to the delivery of DNA to a cell, the DNA may comprise a construct having integrating elements that facilitate the insertion of a sequence of nucleic acids into the genome of the cell.

Exemplary nucleic acids include, without limitation, recombinant nucleic acids, DNA, recombinant DNA, cDNA, genomic DNA, RNA, siRNA, mRNA, saRNA, miRNA, lncRNA, tRNA, and shRNA. In some embodiments, the nucleic acid is homologous to a nucleic acid in the cell. In some embodiments, the nucleic acid is heterologous to a nucleic acid in the cell. In some embodiments, the nucleic acid is in the form of a plasmid. In some embodiments, the nucleic acid is a therapeutic nucleic acid. In some embodiments, the nucleic acid encodes a therapeutic polypeptide.

In some embodiments the nucleic acid encodes a reporter or a selectable marker. Exemplary reporter markers include, without limitation, green fluorescent protein (GFP), red fluorescent protein (RFP), auquorin, beta-galactosidase, Uroporphyrinogen (urogen) III methyltransferase (UMT), and luciferase. Exemplary selectable markers include, without limitation, Blasticidin, G418/Geneticin, Hygromycin B, Puromycin, Zeocin, Adenine Phosphoribosyltransferase, and thymidine kinase.

Surfactants (e.g., 0.1-10% w/w) are optionally used (e.g., poloxamer, animal derived serum, albumin protein) in the flow buffer. Delivery of molecules into cells is not affected by the presence of surfactants; however, surfactants are optionally used to reduce clogging of the device during operation.

In some aspects, the device is made from silicon, metal (e.g., stainless steel), plastic (e.g., polystyrene), ceramics, or any other material suitable for forming one or more appropriately sized channels or conduits. In some aspects, the device is formed of materials suitable for etching micron scaled features and includes one or more channels or conduits through which cells pass. Silicon is particularly well suited, because micro patterning methods are well established with this material, thus it is easier to fabricate new devices, change designs, etc. Additionally, the stiffness of silicon can provide advantages over more flexible substrates like Polydimethylsiloxane (PDMS), e.g., higher delivery rates. For example, the device includes 2, 10, 20, 25, 45, 50 75, 100 or more channels. The device is microfabricated by etching the silicon. Cells are moved, e.g., pushed, through the channels or conduits by application of pressure. A cell driver can apply the pressure. A cell driver can include, for example, a pressure pump, a gas cylinder, a compressor, a vacuum pump, a syringe, a syringe pump, a peristaltic pump, a manual syringe, a pipette, a piston, a capillary actor, and gravity. As an alternative to channels, the cells may be passed through a constriction in the form of a net or closely-placed plates. In either case, the width of the constriction through which the cells traverse is 20-99% of the width or diameter of the cell to be treated in its unconstricted, i.e., suspended, state. Temperature can affect the uptake of compositions and affect viability. The methods are carried out at room temperature (e.g., 20° C.), physiological temperature (e.g., 39° C.), higher than physiological temperature, or reduced temperature (e.g., 0.1° C.), or temperatures between these exemplary temperatures (e.g., 0.1 to 40° C.).

In some embodiments, following controlled injury to the cell by constriction, stretching, and/or a pulse of high shear rate, the cells are incubated in a delivery solution that contains the compound or molecule that one wishes to introduce into the cell. The cells may be contacted with a field when in a solution containing the compound or molecule. Controlled injury may be characterized as small, e.g., 200 nm in diameter, defect in the cell membrane. The recovery period for the cells is on the order of a few minutes to close the injury caused by passing through the constriction. The delivery period comprises 1-10 minutes or longer, e.g., 15, 20, 30, 60 minutes or more, with 2-5 minutes being optimal when operated at room temperature.

Various implementations of the invention may provide one or more of the following capabilities. Greater precision and scalability of delivery can be achieved when compared with prior techniques. Delivery of a material to a cell can be automated. Material such as proteins, RNA, siRNA, peptides, DNA, and impermeable dye can be implanted into a cell, such as embryonic stem cells or induced pluripotent stem cells (iPSCs), primary cells or immortalized cell lines. The device and methods are amenable to any cell type, and the size of the constricted portion is tailored to the type of the cell to be treated. The devices and methods can provide significant advantages. For example, experimental noise in current systems can be reduced when compared with prior techniques. Delivery quantities of a material can be consistent across the cell population. Cells can be individually handled rather than being handled as a batch. The invention has also demonstrated a fairly unique opportunity to deliver a variety of nanoparticles and proteins to the cytosol. Existing methods are fairly unreliable or inefficient at performing such functions.

Methods and devices of the present invention deliver nucleic acids to cells, as well as subcellular structures (e.g., the nucleus and mitochondria) more quickly and efficiently than other methods. Electroporation results in DNA accumulation and interaction with the electropenneabilized plasma membrane during the electric pulse leading to DNA aggregates being internalized into the cytoplasm and accumulating adjacent to the cell membrane inside the cell (FIG. 12 and FIG. 21). DNA cannot easily navigate through the viscous and complicated cytoplasm to reach the nucleus simply by diffusion. Delivery of nucleic acids to the cytosol and nucleus (as well as mitochondria) by DFE using an electric field is rapid and efficient while maintaining cell viability, thereby overcoming the longstanding drawbacks of electroporation alone.

Various implementations of the invention may also provide one or more of the following capabilities. DNA can be delivered into hard-to-deliver cells such as stem cells, primary cells, immune cells. Delivery of very large plasmids (even entire chromosomes) can be accomplished. Quantitative delivery into cells of known amount of a gene construct to study the expression level of a gene of interest and its sensitivity to concentration can also readily be accomplished. Delivery of known amounts of DNA sequences together with known amount of enzymes that enhance DNA recombination in order to achieve easier/more efficient stable delivery, homologous recombination, and site-specific mutagenesis can be accomplished. The methods and devices described herein can also be useful for quantitative delivery of RNA for more efficient/conclusive RNA studies. Delivery of small interfering RNA (siRNA) into the cytoplasm of a cell is also readily accomplished.

Various implementations of the invention may also provide one or more of the following capabilities. RNA can be delivered into a cell for RNA silencing without the need for liposomes. Known amounts of RNA molecules together with known amounts of dicer molecules can be delivered to achieve standardized, efficient, RNA across multiple cell lines in different conditions. mRNA can be delivered into cells to study aspects of gene expression regulations at the posttranscriptional level. The method are also useful to deliver amounts of label of RNA to study the half-life of RNAs as well as using RNA based interference with mitochondrial DNA, e.g., miRNA and lncRNA. Universal protein delivery can be achieved. Known amounts of label proteins can be delivered to study their half-life in cells. Delivery of labelled proteins to study protein localization can be accomplished. Known amounts of tagged proteins can be delivered to study protein-protein interactions in the cellular environment. Delivery of labeled antibodies into living cells for immunostaining and fluorescence-based Western blotting can be achieved.

Various implementations of the invention may also provide one or more of the following clinical and research capabilities. Quantitative delivery of drugs to cell models for improved screening and dosage studies can be achieved. The method could be deployed as a high throughput method of screening protein activity in the cytosol to help identify protein therapeutics or understand disease mechanisms. Such applications are presently severely limited by current protein delivery methods due to their inefficiencies. The devices and techniques are useful for intracellular delivery of drugs to a specific subset of circulating blood cells (e.g. lymphocytes), high throughput delivery of sugars into cells to improve cryopreservation of cells, especially oocytes, targeted cell differentiation by introducing proteins, mRNA, DNA and/or growth factors, delivery of genetic or protein material to induce cell reprogramming to produce iPS cells, delivery of DNA and/or recombination enzymes into embryonic stem cells for the development of transgenic stem cell lines, delivery of DNA and/or recombination enzymes into zygotes for the development of transgenic organisms, DC cell activation, iPSC generation, and stem cell differentiation, nano particle delivery for diagnostics and/or mechanic studies as well as introduction of quantum dots. Skin cells used in connection with plastic surgery are also modified using the devices and method described herein.

Methods and devices relating to the use of an electric field for DFE are especially useful for the delivery of nucleic acids and other charged compounds. DFE is significantly more efficient at delivering charged materials than cell squeeze alone. See, for example, FIGS. 12B and 12C.

In some embodiments of the device and methods described herein, passage of stem cells or progenitor cells such as induced pluripotent stem cells (iPSCs) through a constriction channel does not induce differentiation, but does reliably induce uptake of compositions into the cell. For example, differentiation factors are introduced into such cells. After uptake of introduced factors, the cells proceed on a differentiation pathway dictated by the introduced factor without complications associated with the method by which the factor(s) was introduced into the cell.

In addition to single cells, even very large cells, e.g., eggs; approximately 200 μm in diameter, clusters of cells, e.g., 2-5 cell clusters such as an embryo comprising 2-3 cells, are treated to take up target compositions. The size of the aperture is adjusted accordingly, i.e., such that the width of the constriction is just below the size of the cluster. For example, the width of the channel is 20-99% of the width of the cell cluster.

Cells or cell clusters are purified/isolated or enriched for the desired cell type. Dendritic cells or other cells, e.g., immune cells such as macrophages, B cells, T cells, or stem cells such as embryonic stem cells or iPS, used in the methods may be purified or enriched. For example, cells are isolated or enriched by virtue of their expression of cell surface markers or other identifying characteristics. Dendritic cells are identified and isolated by virtue of their expression of the β-intergrin, CD11c or other identifying cell surface markers. With regard to cells, the term "isolated" means that the cell is substantially free of other cell types or cellular material with which it naturally occurs. For example, a sample of cells of a particular tissue type or phenotype is "substantially pure" when it is at least 60% of the cell population. Preferably, the preparation is at least 75%, more preferably at least 90%, and most preferably at least 99% or 100%, of the cell population. Purity is measured by any appropriate standard method, for example, by fluorescence-activated cell sorting (FACS).

Payload compositions such as polynucleotides, polypeptides, or other agents may be purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. Examples of a an isolated or purified nucleic acid molecule include: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones.

Although purity is desired for some applications, in other applications delivery using methods and devices of the invention uses heterogeneous mixtures of compounds. In some embodiments, high purity is not required for efficient delivery.

A suspension solution is any physiologic or cell-compatible (e.g., a buffer or solution in which a cell may survive in while undergoing DFE or in which a cell proliferates) buffer or solution. For example, a suspension solution is cell culture media or phosphate-buffered saline. One non-limiting example of a suitable buffer for, e.g., HeLa cells, is 25 mM KCl, 0.3 mM $KH_2PO_4$, 0.85 mM $K_2HPO_4$, 36 mM myo-inositol, pH 7.2, osmolality is about 90 mOsm/L, and/or conductivity of about 0.1-5 mS/cm, 0.1-4 mS/cm, e.g., about 3.5 mS/cm at 25° C. This buffer may be changed or modified while maintaining its payload delivery performance. For example, the myo-inositol may be replaced with glucose at the same concentration, but still providing similar performance. The buffer or solution may be adjusted based on many factors and considerations such as the type and strength of field, the cell-type, and the constriction being used. Osmolarity and conductivity, as well as the presence or absence of ions such as potassium and calcium may be adjusted. In certain embodiments, the solution or buffer has a conductivity of substantially or about 1 mS-10 mS or 0.5 mS-15 mS, and/or osmolality of 1-310 or 10-300 mOsm/L. In some embodiments, the pH of the buffer is substantially or about 4-10, 5-9, 6-8, 6.5-7.5, or 7. In some embodiments, the buffer is one that is suitable for electroporation of the cell-type being treated. Electroporation-suitable buffers may be used in embodiments regardless of whether the electric field strength is sufficient for electroporation.

The diameter of the constriction may be selected to induce temporary perturbations of the cell membrane large enough for a payload to pass through when the payload is driven through the perturbations by an electric field. Non-limiting examples of payloads that may be delivered using a microfluidic system of the invention include: protein (such as antibodies and fragments thereof); small molecules; carbohydrates; sugars; polymers of biological, synthetic, organic, or inorganic molecules; Deoxyribonucleic acid (DNA); Ribonucleic acid (RNA) (such as short interfering RNA, hairpin RNA, repeat-associated short interfering RNA, micro-RNA, self-amplifying RNA and mRNA molecules); DNA or RNA comprising modified nucleotides that increase the stability or half-life of the DNA or RNA in vivo or in vitro; peptide nucleic acid (PNA); methylated DNA; a naturally occurring chromosome or a portion thereof; and/or an expression vector such as a plasmid. In some embodiments, the payload comprises a mixture of different compounds, e.g., a mixture of one or more of a protein, a small molecule, a carbohydrate, a sugar, a polymer, a DNA, a RNA, a modified or methylated DNA or RNA, a PNA, a naturally occurring chromosome or a portion thereof, and/or an expression vector such as a plasmid. In some embodiments, a DNA molecule is single stranded, double stranded, circular, linear, or supercoiled. In embodiments involving double stranded linear DNA, the DNA may have, e.g., blunt ends or a 5' or 3' overhang of one or more nucleic acids. The small molecule may be, e.g., an organic compound less than 1 kDa in size. In some embodiments the payload is charged and in others the payload is uncharged. Without wishing to be bound by any scientific theory, uncharged as well as charged molecules may be delivered using methods and systems provided herein due to fluidic flow caused by an electric field as salts interact with the field.

In embodiments in which a payload is delivered to a eukaryotic cell, the payload may be driven into the cytoplasm, an organelle (such as a mitochondrium), and/or the nucleus of the cell. For example, the payload is driven into the nucleus of the cell while the cell passes through the electric field, or less than substantially or about 0.1, 0.5, 1, 1.5, 2, 2.5, 3, 3.5, or 4 hours after the cell passes through the electric field. In embodiments involving the delivery of a payload to a plurality of cells, at least substantially or about 10, 20, 25, 30, 35, 40, 45, 50, 55, 60, 65, 70, 75, 80, 85, 90, 95, 99, 100, 0-65, or 10-100% of the plurality of cells express the DNA within substantially or about 0.1, 0.5, 1, 1.5, 2, 2.5, 3, 3.5, 4, 0.1-4, or 0.1-48 hours after the plurality of cells passes through the electric field.

In some embodiments, the cell is a prokaryotic cell. Non-limiting examples of prokaryotic cells include bacterial cells (e.g., gram-positive, gram-negative, pathogenic, non-pathogenic, commensal, cocci, *bacillus*, and/or spiral-shaped bacterial cells) and archaea cells. In other embodiments, the cell is a eukaryotic cell. Non-limiting examples of eukaryotic cells include protozoan, algal, fungi, yeast, plant, animal, vertebrate, invertebrate, arthropod, mammalian, rodent, primate, and human cells. The cell may be a cell, e.g., of a unicellular organism or a multicellular organism. The cell may be, e.g., a primary eukaryotic cell or an immortalized eukaryotic cell. In some embodiments, the cell is a cancer cell. In certain embodiments, the cell is other than a human cell. In various embodiments, a cell may be in a mixture of two or more cell types or a plurality of cells may be a mixture of two or more cell types. A mixture of cell types may be a co-culture of multiple cell types (such as two or more of those disclosed herein) or a mixture of cell types that naturally occur together, such as in whole blood.

In some embodiments, the cell is a peripheral blood mononuclear cell. In various embodiments, the cell suspension comprises a purified cell population. In certain embodiments, the cell is a primary cell or a cell line cell.

In some embodiments, the cell is a blood cell. In some embodiments, the blood cell is an immune cell. In some embodiments, the immune cell is a lymphocyte. In some embodiments, the immune cell is a T cell, B cell, natural killer (NK) cell, dendritic cell (DC), NKT cell, mast cell, monocyte, macrophage, basophil, eosinophil, or neutrophil. In some embodiments, the immune cell is an adaptive immune cell such as a T cell and B cell. In some embodiments, the immune cell is an innate immune cell. Exemplary innate immune cells include innate lymphoid cells (ILC1, ILC2, ILC3), basophils, eosinophils, mast cells, NK cells, neutrophils, and monocytes. In some embodiments, the immune cell is a memory cell. In some embodiments, the immune cell is a primary human T cell. In some embodiments, the cell is a mouse, dog, cat, horse, rat, goat, monkey, or rabbit cell. In some embodiments, the cell is a human cell. In some embodiments, the cell suspension comprises non-mammalian cell. In some embodiments, the cell is a chicken, frog, insect, or nematode cell. Aspects of the present invention relating to a cell also apply to a platelet. Therefore, references to a "cell" herein may also apply to a platelet.

In some embodiments, the microfluidic channel has a single cell-deforming constriction (i.e., no more than one). In other embodiments, the microfluidic channel has multiple cell-deforming constrictions in series.

In various embodiments, the cell is contacted with the electric field substantially or about 0.0001, 0.001, 0.002, 0.003, 0.004, 0.005, 1, 2, 3, 4, 5, 6, 7, 8, 9, 10, 0.001-0.005, 0.0001-10, 0.0001-20, 0.0001-30 seconds or more (e.g., about 0.5, 1, 2, 3, 4, 5, 6, 7, 8, 9, 10, 0.1-10, 1-15, or 1-15 minutes or more) after exiting the cell-deforming constriction, or about 0.0001, 0.001, 0.002, 0.003, 0.004, 0.005, 1, 2, 3, 4, 5, 6, 7, 8, 9, 10, 0.001-0.005, 0.0001-10, 0.0001-20, 0.0001-30 seconds or within about 0.5, 1, 2, 3, 4, 5, 6, 7, 8, 9, 10, 0.1-10, 1-15, or 1-15 minutes after exiting the cell-deforming constriction. It will be understood that the distance between electrodes and a constriction can be varied depending on factors such as the speed at which the cell is traveling.

In some embodiments, the cell-deforming constriction event induces temporary perturbations of the cell membrane large enough for a payload to pass through. In some aspects, at least one electrode is in proximity to the cell-deforming constriction such that the cell is exposed to an electric field while there are temporary perturbations on the cell's membrane. Non-limiting examples of distances "in proximity" to a cell-deforming constriction are substantially or about 0.1, 0.5, 1, 2, 3, 4, 5, 0.1-5 cm, 1-10, 1-100, or 1-1000 cm.

Any of the methods described above are carried out in vitro, ex vivo, or in vivo. For in vivo applications, the device may be implanted in a vascular lumen, e.g., an in-line stent. These and other capabilities of the invention, along with the invention itself, will be more fully understood after a review of the following figures, detailed description, and claims.

Aspects of the present invention provide a method for delivering an expression vector encoding a transgene into a cell. In preferred embodiments, the method includes passing a solution comprising the cell and the expression vector through a cell-deforming constriction such that a pressure is applied to the cell causing perturbations of the cell membrane large enough for the expression vector to pass through. The cell may be contacted with an electric field a magnetic field, or an acoustic field before, during, and/or after it exits the cell-deforming constriction.

In some embodiments, the transgene is expressed in the cell sooner than in a corresponding cell that was contacted with an electric field, magnetic field, or acoustic field without passing through a cell-deforming constriction. For example, the transgene may be expressed in the cell 0.1, 1.5, 1, 1.5, 2, 2.5, 3, 3.5, 4, or 0.1-4 hours sooner than in a corresponding cell that was contacted with an electric field, magnetic field, or acoustic field without passing through a cell-deforming constriction.

In various embodiments, the maximum transgene expression in the cell is achieved at a faster rate compared to maximum transgene expression in a corresponding cell that was contacted with an electric field, magnetic field, or acoustic field without passing through a cell-deforming constriction. For example, the maximum transgene expression in the cell may be achieved 0.1, 1.5, 1, 1.5, 2, 2.5, 3, 3.5, 4, or 0.1-4 hours sooner than the maximum transgene expression in a corresponding cell that was contacted with an electric field, magnetic field, or acoustic field without passing through a cell-deforming constriction.

In certain embodiments, the transgene is expressed in the cell to a greater extent compared to expression of the transgene in a corresponding cell that was contacted with an electric field, a magnetic field, or an acoustic field without passing through a cell-deforming constriction. For example, the transgene expression in the cell may be at least substantially or about 5, 10, 15, 20, 25, 30, 35, 40, 45, 50, 55, 60, 65, 70, 75, 80, 85, 90, 95, or 100% greater, or 2-fold, 5-fold, 8-fold, 10-fold, 20-fold or more greater than the expression of the transgene in a corresponding cell that was contacted with an electric field, a magnetic field, or an acoustic field without passing through a cell-deforming constriction.

Aspects of the present invention also relate to a method for delivering an expression vector encoding a transgene into a population of cells. In preferred embodiments, the method includes passing a solution comprising the cells and the expression vector through a cell-deforming constriction such that a pressure is applied to the cells causing perturbations of the cells large enough for the expression vector to pass through. The cells may be contacted with an electric field, a magnetic field, or an acoustic field, before, during, or after exiting the cell-deforming constriction.

In some embodiments, the proportion of cells expressing the transgene in the population is greater than the proportion of cells expressing the transgene in a population of corresponding cells that were contacted with an electric field, magnetic field, or acoustic field without passing through a cell-deforming constriction. For example, the proportion of cells expressing the transgene in the population may be at least substantially or about 5, 10, 15, 20, 25, 30, 35, 40, 45, 50, 55, 60, 65, 70, 75, 80, 85, 90, 95, or 100% greater, or 2-fold, 5-fold, 8-fold, 10-fold, 20-fold or more greater than the proportion of cells expressing the transgene in a population of corresponding cells that were contacted with an electric field, magnetic field, or acoustic field without passing through a cell-deforming constriction.

In some embodiments, transgene expression in the cell is at least substantially or about 5, 10, 15, 20, 25, 30, 35, 40, 45, 50, 55, 60, 65, 70, 75, 80, 85, 90, 95, or 100% greater, or 2-fold, 5-fold, 8-fold, 10-fold, 20-fold or more greater than the expression of the transgene in a corresponding cell that was contacted with an electric field, a magnetic field, or an acoustic field without passing through a cell-deforming constriction within substantially or about 0.1, 1.5, 1, 1.5, 2, 2.5, 3, 3.5, 4, or 0.1-4 hours after the cell passes through a constriction.

In certain embodiments, the proportion of cells expressing the transgene at a high level in the population is greater than the proportion of cells expressing the transgene at a high level in a corresponding population of cells that were contacted with an electric field, magnetic field, or acoustic field without passing through a cell-deforming constriction. For example, the proportion of cells expressing the transgene at a high level in the population may be at least substantially or about 5, 10, 15, 20, 25, 30, 35, 40, 45, 50, 55, 60, 65, 70, 75, 80, 85, 90, 95, or 100% greater, or 2-fold, 5-fold, 8-fold, 10-fold, 20-fold or more greater than the proportion of cells expressing the transgene in a population of corresponding cells that were contacted with an electric field, magnetic field, or acoustic field without passing through a cell-deforming constriction. In some embodiments, a "high level" of transgene expression is a level of expression in a cell which is 50% higher than the average level of transgene expression in a cell that was passed through an electric field, magnetic field, or acoustic field without passing through a cell-deforming constriction. Non-limiting examples of methods for determining the level of transgene expression include quantitative polymerase chain reaction (qPCR) assays, Northern Blot, Western Blot, and microarray-based assays.

Each embodiment disclosed herein is contemplated as being applicable to each of the other disclosed embodiments. Thus, all combinations of the various elements described herein are within the scope of the invention.

Related apparatus, systems, techniques, and articles are also described.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIG. 1 is a picture of an example implementation of a microfluidic device for delivering a payload, such as DNA or RNA, to a cell for genetic engineering.

FIG. 2 is an alternative implementation of the electrodes illustrated in FIG. 1. The offset in the electrodes promotes the exposure of cells to the electric field regardless of where they are in the channel as they flow through.

(FIG. 9A) Schematic illustrating the working mechanism: the mechanical disruption of a cell, as it passes through the constriction, generate holes on the plasma membrane. The following electric pulse drives DNA into cytoplasm and nucleus through the holes. (FIG. 9B) A set of identical parallel microfluidic constriction are etched onto a silicon wafer, and a set of electrodes are deposited on a Pyrex wafer. (FIG. 9C) An optical image of a finished device bonded by silicon wafer and Pyrex layer. More details of device fabrication can be found in FIG. 13.

As shown in FIG. 10A, greater DNA expression was achieved at each field strength compared to electrophoresis, showing that a lower energy level is required for electric field DFE compared to electrophoresis. All data points were collected in triplicate and error bars represent 2 SDs. The X-Axis units are volts per 60 um. 1V/60 um is equivalent to about 0.1667 kV/cm.

(FIG. 11A) GFP expression efficiency as a function of time post treatment. Efficiency is defined as the GFP expressing cells over total live cells after treatment. 10-7 chip is used for squeeze and Disruption and Field Enabled Delivery (DFE). As used herein, device dimensions are denoted by a series of numbers indicating length, and width (e.g., 10-7 denotes a device with a single constriction of 10 µm length and 7 µm width). A pulse of 0.1 ms/10 v at a frequency of 200 Hz is used for EP and ME (microfluidic (without constriction)+electric field), and a single pulse of 15 ms/15000 v is used in BEP. (FIG. 11B) The dynamics of DNA expression is analyzed by measuring differential GFP expression at different time points after treatment. More than 80% of transfected cells expressed GFP within 1 h after treatment in microinjection and DFE. In contrast, most of transfected cells in ME (60%), BEP (70%) and LP2000 (95%) express GFP 4 to 48 h after treatment. The number of Hela cells in every treatment for each method is shown as well, indicating the throughput of each technique (FIG. 11C). Each data point was run in triplicate, and error bars represents 2 SDs.

FIG. 12A-C are pictures showing the visualization of the delivery of fluorescence labeled plasmid DNA (LDNA) to HeLa cells. After nucleus and plasma membrane staining, Cells were mixed with Cy3 labeled plasmid DNA before transfection. After treatment, cells were washed with OPTI MEM, fixed with cell fixation kit, and ready for confocal imaging. (FIG. 12A) in BEP, electric pulse of 0.1 ms (200 Hz) was applied at 10 V when the cells flow through the chip at the speed of 500 mm/s (when cell passes through the constriction). DNA accumulation was found on the plasma membrane. (FIG. 12B) by just cell squeeze, little or no LDNA signal was found in the cell, 10-7 chip was used at cell speed of 500 mm/s. (FIG. 12C) in DFE, a significant Cy3 fluorescence was observed filling cytoplasm and nucleus. 10-7 chip was used at cell speed of 500 mm/s with applied electric pulse of 0.1 ms (200 Hz) at 10 V.

FIG. 13 is an illustration of an exemplary device fabrication process. (FIGS. 13*a-d*) Fabrication of the electrodes on a Pyrex layer includes a metal deposition process and a following lift-off process. (FIGS. 13*e-h*) Fabrication of microchannels on silicon wafer using twice lithography and DRIE process. (i) The bonding between the silicon substrate and the Pyrex layer.

FIG. 14 is a line graph illustrating delivery performance that depends on cell speed. Delivery efficiency of 3 K Da dextran, DNA transfection efficiency, and cell viability were measured 24 hours after treatment. 10-8 chip was used and the electric pulse of 0.1 ms (200 Hz) at 10 V. The yield of DNA transfection is maximum near the cell speed of 300 mm/s.

(FIG. 15A) Comparison of the expression of GFP plasmid DNA by DFE, BEP, and LP2000. Fluorescence microscopy images of cells shows that GFP expression occurred much fast in DFE than BEP and LP2000.

As shown in FIG. 12A and depicted in FIG. 21A, DNA delivered by electroporation accumulates on the plasma membrane. FIG. 12B (illustrated in FIG. 21B) shows low or no DNA delivery with cell squeeze alone. However, FIG. 12C (depicted in FIG. 22C) demonstrates a rapid and dramatic increase in DNA delivery throughout the cell using DFE.

Like reference symbols in the various drawings indicate like elements.

DETAILED DESCRIPTION OF THE INVENTION

Figure 2:
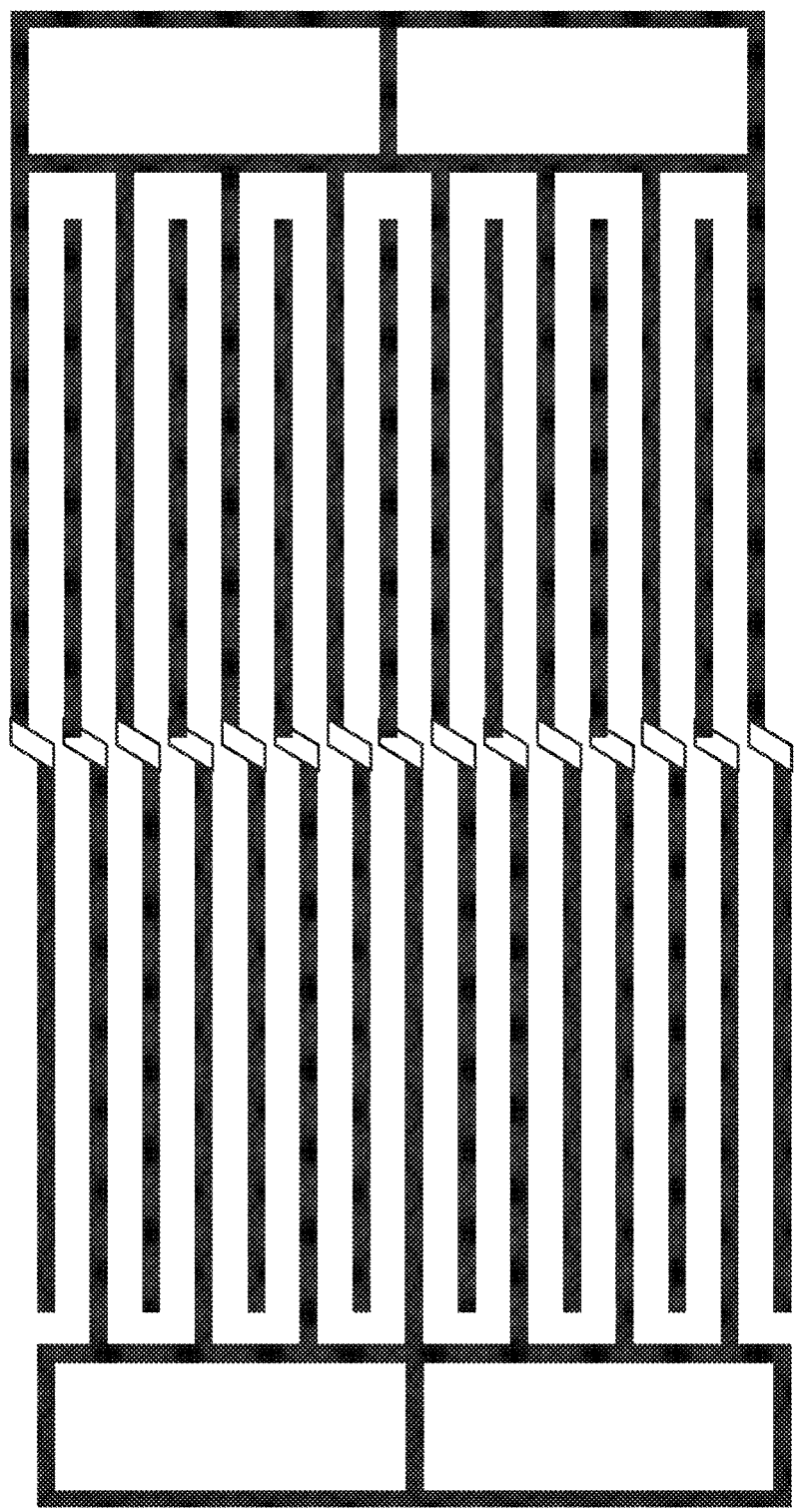

Intracellular delivery of macromolecules, such as DNA and RNA, is a critical step in many therapeutic and research applications. Gene delivery can be achieved by virus-mediated, chemical, electrical, and mechanical transfections. Viral vector based methods can be efficient for certain applications, but they often risk chromosomal integration and have safety risks for in vivo use. Chemical modification of target molecules can also facilitate membrane poration or endocytotic delivery, but these approaches are often limited by the structure of target molecule and target cell type. Microinjection suffers from low throughput. Electroporation has demonstrated its efficacy in DNA and RNA delivery applications for previously difficult-to-transfect cells. However, this method may cause cell death and damages sensitive materials such as quantum dots due to high intensity electric field. A constriction microfluidic platform can produce transient cell membrane disruption that facilitates passive diffusion of most materials into the cytoplasm of almost any cell type. The delivery platform has the advantage of high throughput, independence from exogenous materials or fields, and high cell viability. An example membrane disruptive delivery platform is described in U.S. Patent Publication Number 2014/0287509, published Sep. 25, 2014, the entire contents of which are hereby expressly incorporated by reference herein. Coupled to an electric field, however, enables inducement of gene expression in response to delivery of plasmid DNA. The present subject matter includes an intracellular delivery technique and platform that can deliver any functional target molecule into any cell type.

The current subject matter includes a high-throughput, vector-free microfluidic device for intracellular delivery of DNA using mechanically transient cell membrane disruption and an electric field.

FIG. 1 is a picture of an example implementation of a microfluidic device 100 for delivering a payload, such as DNA or RNA, to a cell for genetic engineering. The microfluidic device 100 includes one or more constriction channels 105 and at least one electrode 110 for generating an electric field. The at least one electrode 110 can include pairs of electrodes with different sizes. The constriction channels 105 are shown left, and are sized to constrict a cell as it passes through the channel 105 at a constriction point 107. When a cell passes through a constriction point 107 with a minimum dimension smaller than the cell diameter, the cell undergoes rapid mechanical deformation, which produces transient membrane disruptions of holes.

Molecules from the surrounding medium can then diffuse into the cell cytosol through these holes. After passing through the constriction point 107, the cell enters an electric field produced by the electrodes 110 that is positioned downstream of the constriction point 107, where a payload, such as DNA, is driven into the cell by electrophoretic effects produced by the electric field. If the payload is charged, the payload can be directly driven and if the payload is not charged, the payload can be indirectly driven, for example, by suspending the payload in a buffer with charged components, for example, salts, that may server to drive the payload when under electrophoretic effects produced by the electric field. The electrodes 110 are illustrated on the right side of FIG. 1.

FIG. 2 is an alternative implementation of the electrodes 110 illustrated in FIG. 1. The width of electrodes and spacing between electrodes are both 50 μm. The length of electrodes are 8 mm. In an implementation, the range of such dimension can be 100 nm to 10 cm depending on the specific design and application. The shift design of the electrodes in FIG. 2 aid each cell passing through the channel to be exposed to the electric field, resulting a higher DNA transfection efficacy. In its current implementation, the gold electrodes are in plane, on the glass side (top). The electrodes could however be implemented on the silicon layer (bottom) or on both layers (top and bottom). The current electrode configuration (FIG. 2) consists of a series of straight electrodes that alter position halfway through the channel to ensure any cell passing in the fluidic channels below are exposed to a field, i.e. if a cell was travelling directly under an electrode, after the shift it will now be positioned between two electrodes and hence exposed to the fields. This consideration is important in that it ensures that most (at least 20, 50, 75, 80, 85, 90, 95, 99% or more) or all cells are exposed to an electric field. The shift angle can range from 1-90 degrees can be at any point along the length of the electrode, e.g., at the halfway point (as shown in FIG. 2) or at a point that is 5, 10, 20, 25, 35, 50, 60, 75, 80, 85, 90, 95% or more of the distance between the electrodes. One could also implement electrodes perpendicular to cell flow or at a diagonal angle (ranging from 1-90 degrees).

The microfluidic platform can be made by etching microfluidic channels into a silicon wafer using deep reactive ion etching. Electrodes can be deposited on top of a Pyrex wafer using photolithography and lift-off. Then those two wafers can be bonded together to seal the microfluidic channels, e.g., through anodic or another means of bonding. In some examples, the electrodes are located on the top (e.g., glass) plate/wafer (i.e., absent from the bottom (silicon wafer); alternatively, the electrodes are located on the bottom plate (are absent from the top plate/wafer). In some embodiments, electrodes are located on both sides of the device, e.g., on or in the top and the bottom plate or wafer. The horizontal lines in FIG. 2 depict electrodes connected to either a negative pad or a positive pad (rectangles in the figure). In this configuration, cells flow from left to right underneath the electrodes located in the glass wafer. To ensure that each cell is exposed to an electrical field, the electrodes are offset at a point (e.g., grey portion of electrode) in the electrode configuration. For example, the offset is at an angle of about 1-90°, e.g., 20-80°, e.g., about 45° as shown in FIG. 2. In this manner, a cell flowing through the microfluidic device in a straight line is will encounter an electric field during at least a portion of its traverse over the length the microfluidic channel.

Figure 3:
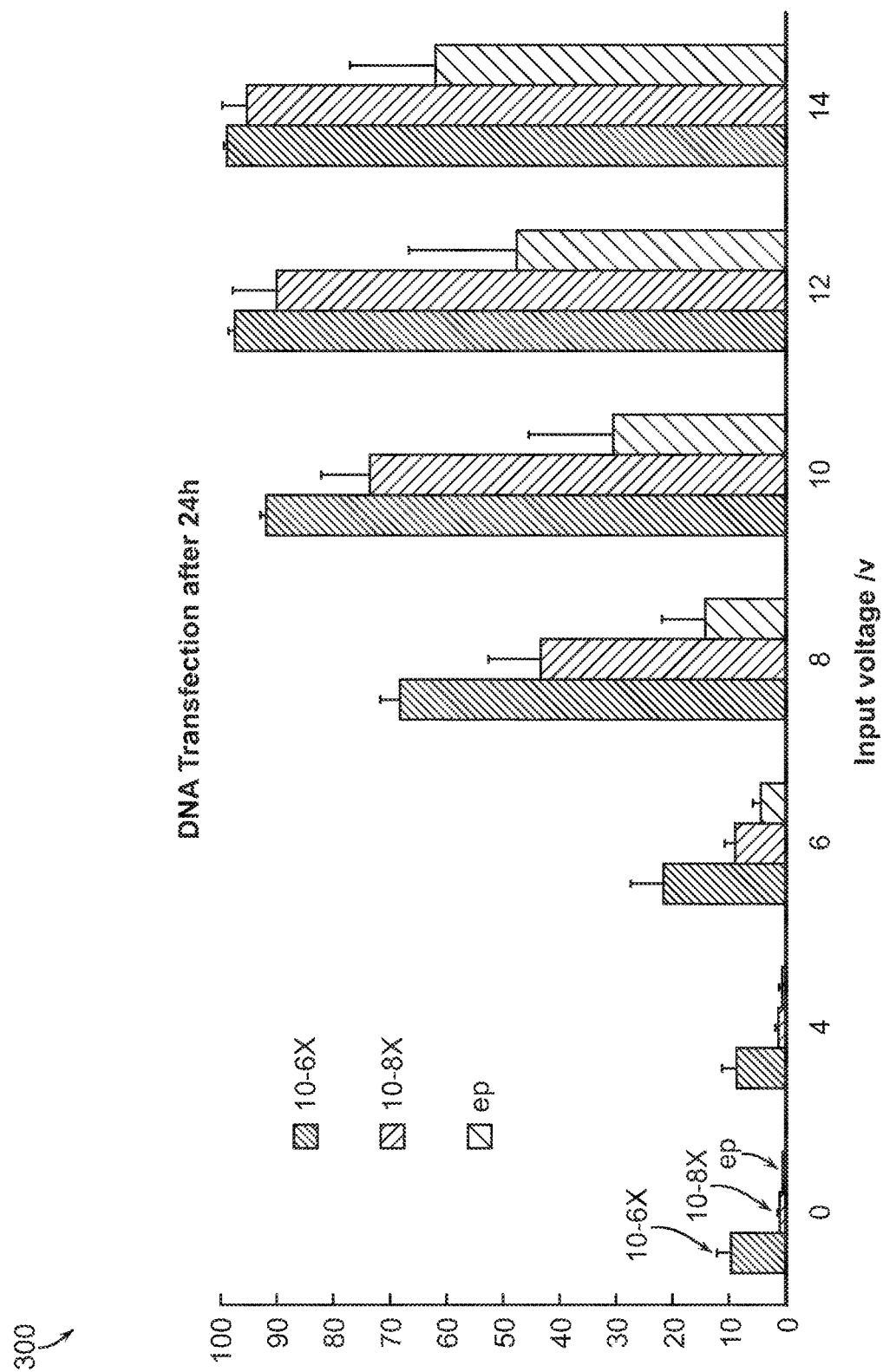
FIG. 3 is a bar graph illustrating DNA transfection rates for example cells driven through the microfluidic system to deliver a payload DNA. DFE 10-6 denotes the constriction dimensions of DFE device, the first number corresponds to constriction length while the second to width (in microns).

The electric field can be, e.g., 0.1 kV/m-2000 kV/m, 10-2000 kV/m or 0.1 kV/m-100 MV/m, preferably at 50-500 kV/m. In addition, cells can be exposed to the electric field for a known time. Pulse width 1 ns-1 s and period 100 ns-10 s is an example. Preferably at 0.05-0.5 ms pulse width and 1-20 ms period. The intensity of the electric field required for delivery may be lower than traditional electroporation. As a result, for a fixed delivery efficiency, the current subject matter can require a lower electric field intensity than electroporation. As shown in FIG. 3, DNA transfection efficiency using a method of the invention is better than electroporation at different field strengths, showing that lower field strengths can be used to obtain the same similar or greater transfection efficiency compared to electroporation alone.

Electroporation involves the combination of pulse strength and pulse width. For example, in the Neon® Transfection System, the pulse is usually 0.3-1 kV·cm with a pulse width of 5 ms-50 ms. In some embodiments comprising an electric field, the electric field strength is similar to that used for electroporation, but the pulse width is much lower than for electroporation. The use of a lower pulse width results in a lower exposure of the cells to energy, and higher viability. Additionally, and despite the lower energy exposure, DNA is delivered to the nucleus (and other areas of the cell) and expressed more quickly compared to electroporation alone.

In an example operation, cells can be driven through the constriction channels 105 at constant pressure (5 psi-100 psi). The cells are then contacted with a pulsed electric field driven by a function generator. In one example, an integrated circuit is used to provide an electrical signal to drive the electrodes. Delivery efficiency of Cascade Blue labelled 3-kDa dextran molecules and expression of Green Fluorescent Protein (GFP)-expressing plasmid DNA are characterized by flow cytometry to evaluate performance. The results show a delivery efficiency of 70% for 3 K dextran and 63% for DNA transfection while cell viability is maintained at 90%. Such simultaneous delivery of both small molecule and large molecule is challenging for other technologies.

The subject matter described herein can provide many advantages. For example, gene expression can be greatly increased. In an implementation, gene expression in a constriction only device is less than 5% and can be increased to 63% by inclusion of the electrical field. In some embodiments, gene expression in a constriction only device is less than about 1, 2, 3, 4, or 5% and can be increased to about 60-100 or 65, 70, 75, 80, 85, 90, 95, or 100% by exposure of squeezed cells to an electrical field. A device that includes both a cell-deforming constriction and an electrode is advantageous for different types of payload delivery. For example, such as device effectively delivers both relatively large and small molecules into a cell in one process or passage through the device by virtue of exposure to a constriction and then to an electrical field. For example, the system is particularly useful to deliver nucleic acids encoding gene products, e.g., plasmid DNA, into the cell and into the nucleus to achieve expression of the delivered gene. For example, exposure of cell to an electrical field after passage through the cell-deforming constriction facilitates nuclear entry of a plasmid. This approach can also enable simultaneous delivery of various materials, such as a protein and a nucleic acid. The cell deforming element would facilitate disruption of the outer membrane to facilitate cytosolic protein delivery while the electric field facilitates potential nuclear disruption and enables electrophoretic flow of material into the cells.

FIG. 3 is a bar graph 300 illustrating DNA transfection rates for example cells driven through the microfluidic system 100 to deliver a payload DNA and after 24 hours of incubation. The time each cell spends on passing through the electric field is 36 mS and pulsed electric signal has duration time of 0.1 mS with period of 5 mS. Cells are suspended in hypoosmolar buffer before treatment, and then injected through microfluidic chip for squeezing and passage through an electric field. Cells are then collected and wait for 3 minutes before adding into culture medium. DNA transfection is analyzed using Fluorescence-activated cell sorting (FACS) after 24 hours incubation. Results illustrated in FIG. 3 shows that cell squeezing significantly enhance the DNA transfection during the passage through an electric field.

Figure 4:
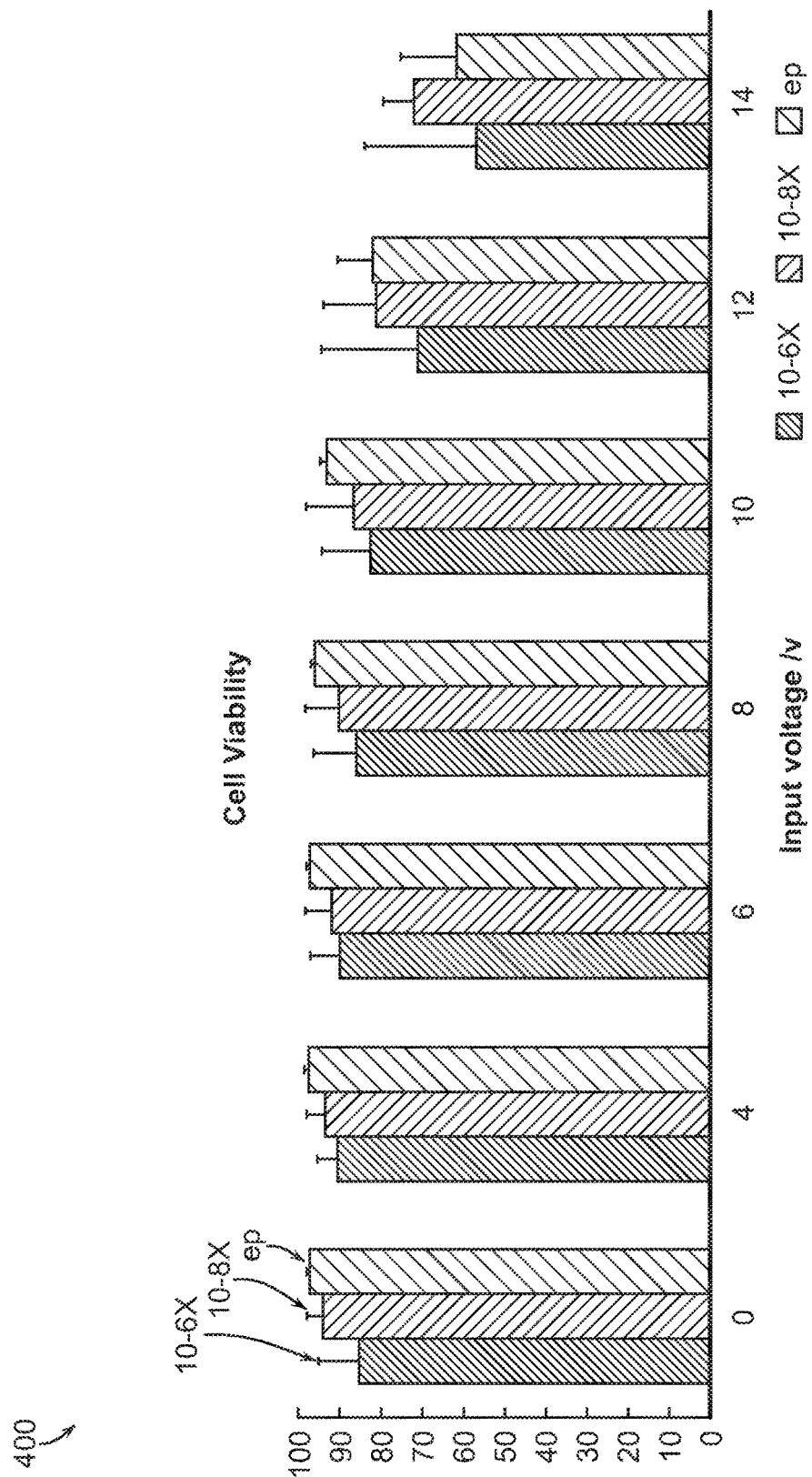
FIG. 4 is a bar graph illustrating cell viability.

FIG. 4 is a bar graph 400 illustrating cell viability. The time each cell spends on passing through the electric field is 36 mS; pulsed electric signal has duration time of 0.1 mS with period of 5 mS; Cells are suspended in hypoosmolar buffer before treatment, and then injected through microfluidic chip for squeezing and passage through an electric field. Cells are then collected and wait for 3 minutes before adding into culture medium. DNA transfection is analyzed using FACS after 24 hours incubation. Results shows that cell squeezing significantly enhance the DNA transfection during the passage through an electric field.

Figure 5:
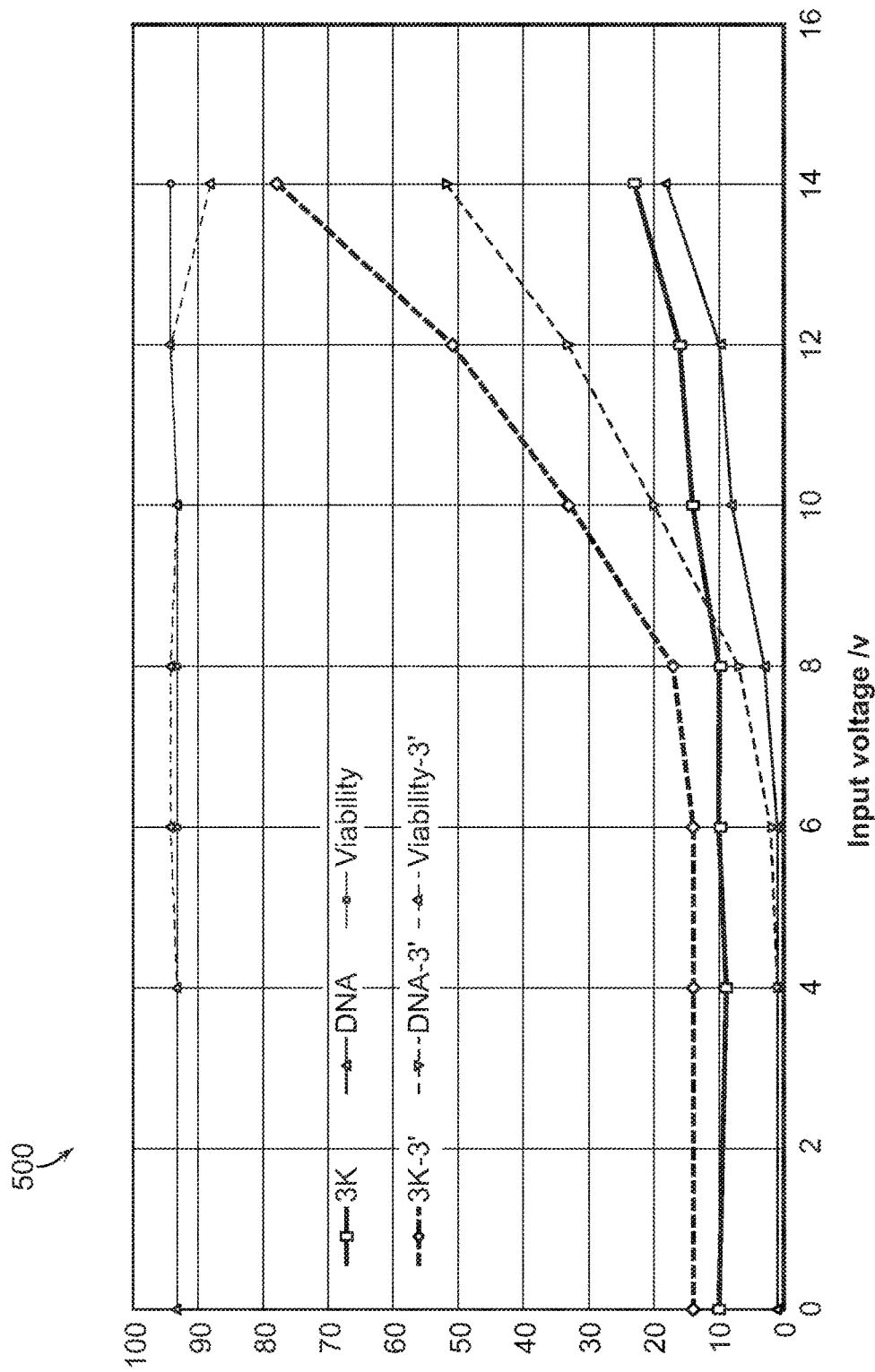
FIG. 5 is a line graph illustrating DNA transfection and viability.

FIG. 5 is a line graph 500 illustrating DNA transfection and viability. The time each cell spends on passing through the electric field is 24 mS; pulsed electric signal has duration time of 0.1 mS with period of 5 mS; 10-8× chip is used. Cells are suspended in hypo-osmolar buffer and mixed with GFP-DNA plasmid and 3 K Da dextran before treatment, and then injected through microfluidic chip for squeezing and passage through an electric field. Cells are then collected and (dashed line) wait for 3 minutes before or directly (solid line) add into culture medium. DNA transfection is analyzed using FACS after 24 hours incubation.

Figure 6:
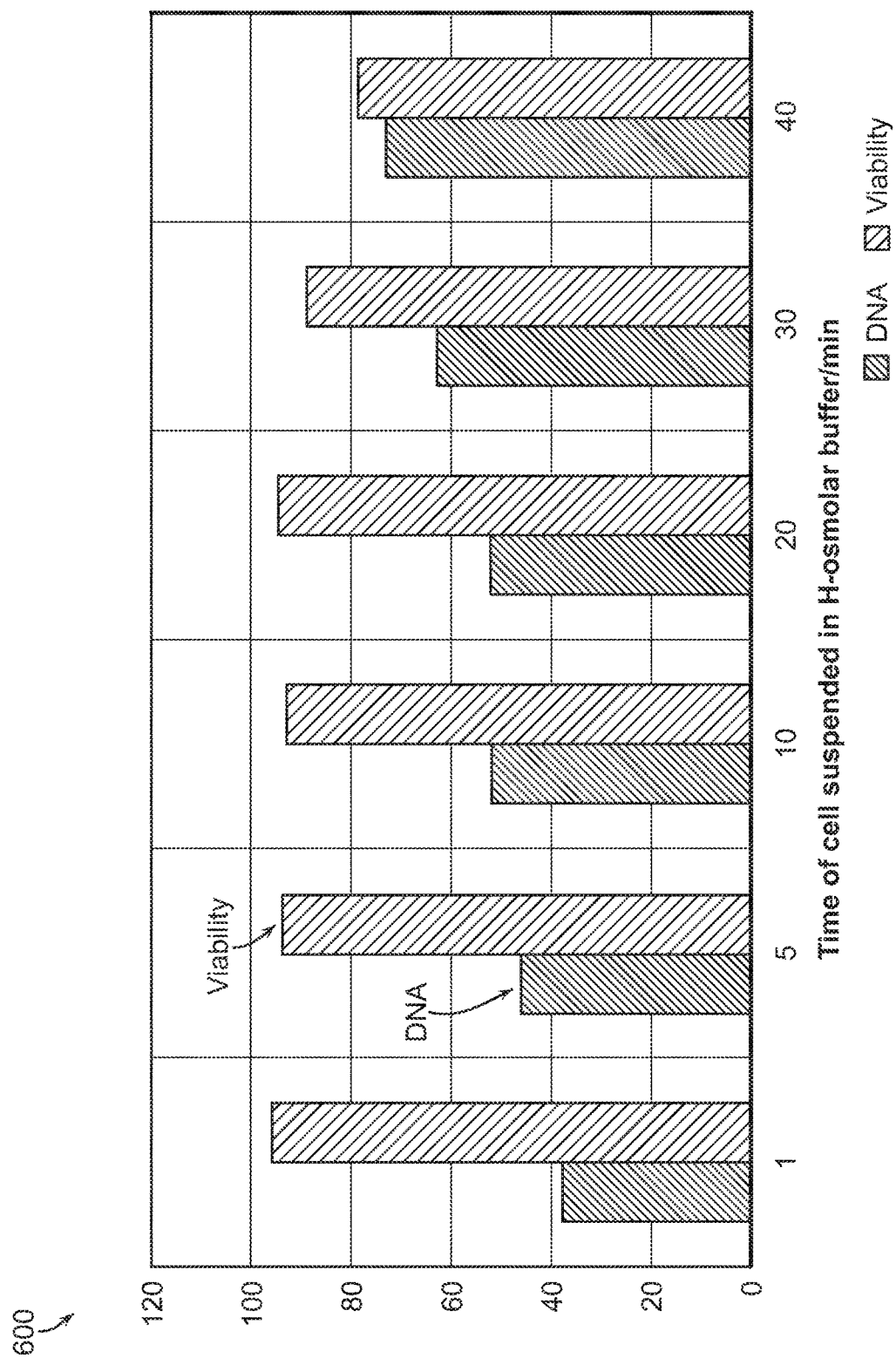
FIG. 6 is a bar graph illustrating how exposure time to such buffer before treatment affect DNA delivery and cell viability.

FIG. 6 is a bar graph 600 illustrating how exposure time to such buffer before treatment affect DNA delivery and cell viability. The time each cell spends on passing through the electric field is 24 mS; pulsed electric signal has duration time of 0.1 mS with period of 5 mS; 10-8× chip is used. Cells are suspended in hypo-osmolar buffer and mixed with gfpDNA plasmid and 3 K Da dextran. An exposure time of up to 40 minutes is explored, as shown in FIG. 6. Cells are then collected and directly (solid line) added into culture medium. DNA transfection is analyzed using FACS after 24 hours incubation.

Figure 7:
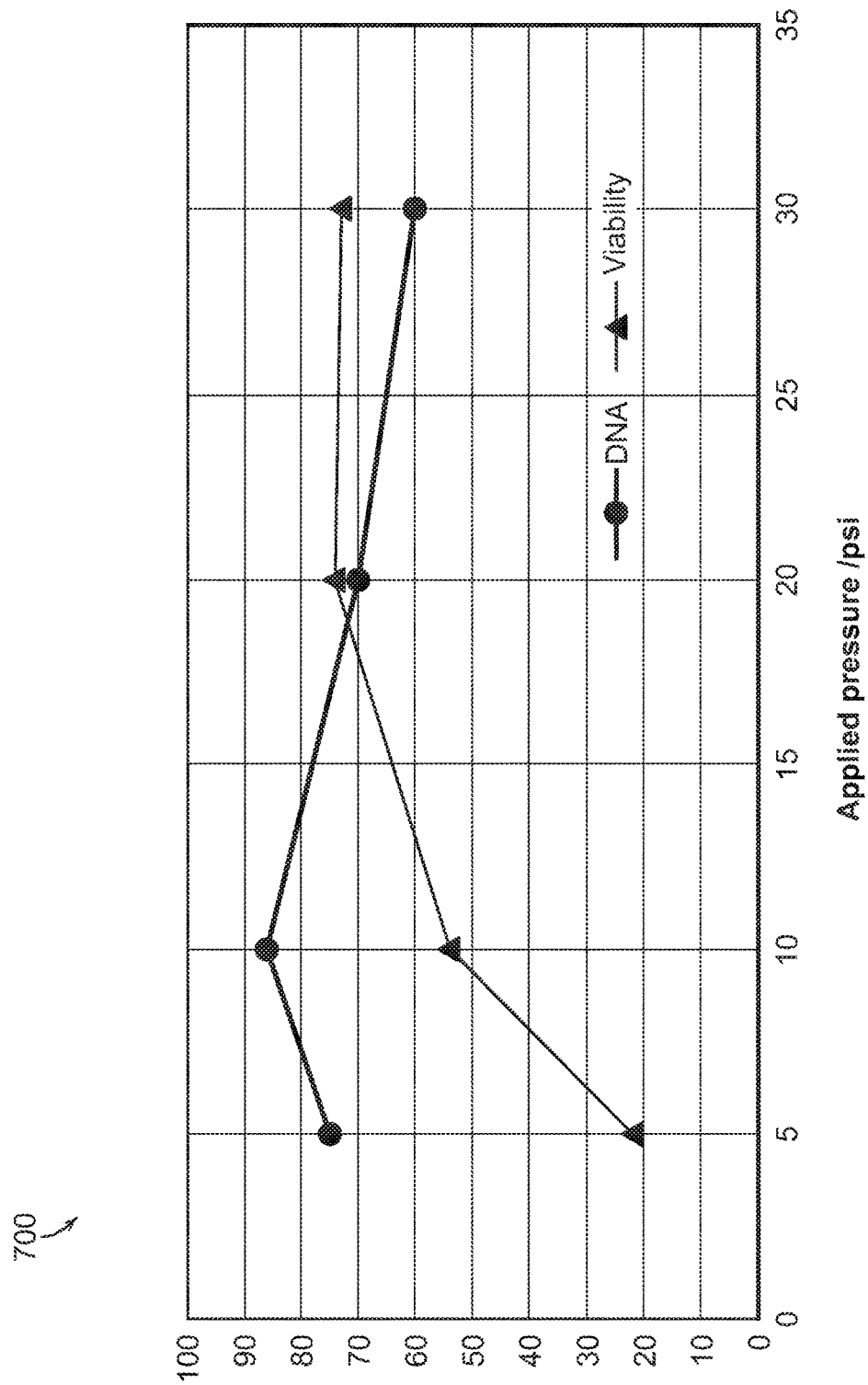
FIG. 7 is a line graph illustrating that when cell speed increase, cell viability also improves.

FIG. 7 is a line graph 700 illustrating that when cell speed increase, cell viability also improves, which means electric field is mainly responsible to decrease in cell viability. The time each cell spends on passing through the electric field is 24 mS; pulsed electric signal has duration time of 0.1 mS with period of 10 mS; 10-7× chip is used. Delivery performance depends on cell speed, which is controlled by the applied pressure. Cells are suspended in hypo-osmolar buffer and mixed with gfpDNA plasmid; after treatment, cells are added directly into culture medium. With higher speeds, disruption of the membrane is more severe but field exposure may be reduced.

Figure 8A:
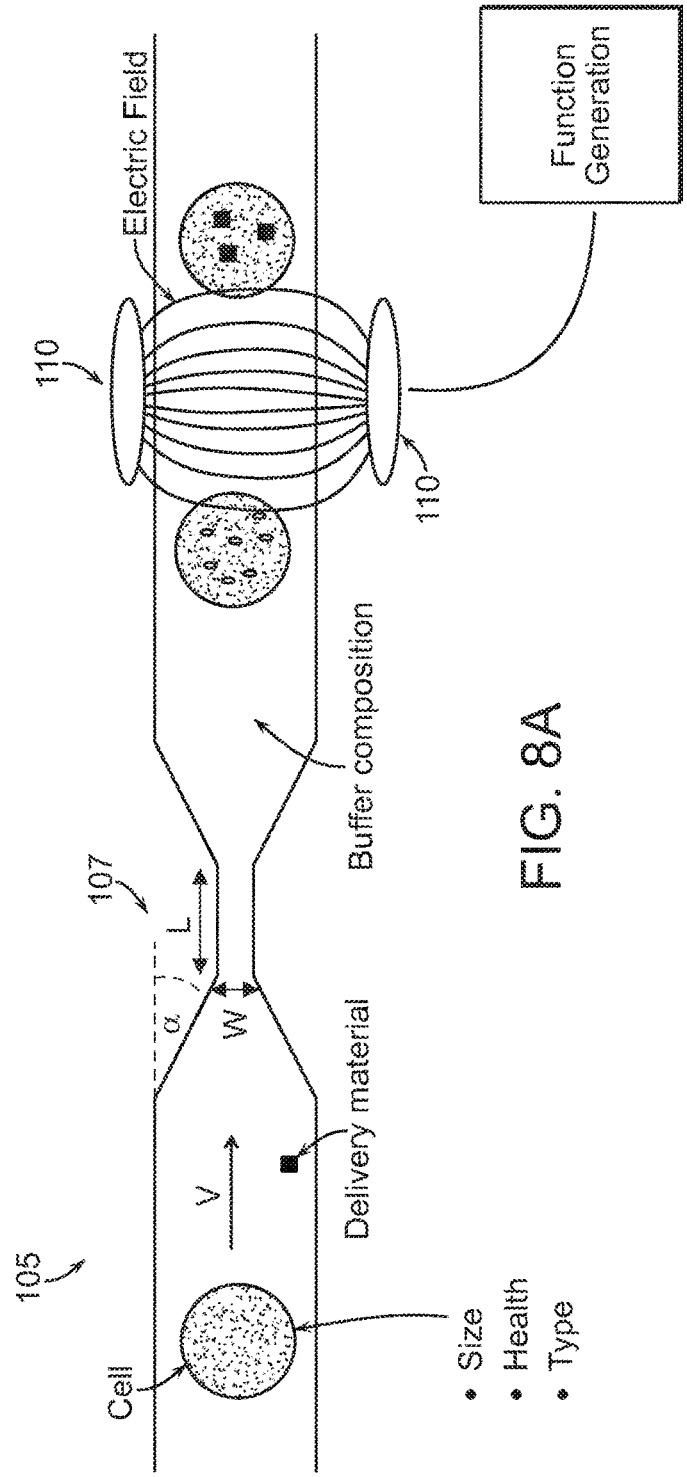
FIG. 8A is a schematic diagram of an embodiment of a microfluidic system illustrating a single constriction channel.
Figure 8B:
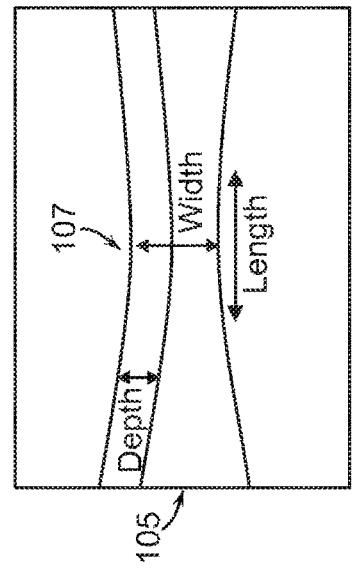
FIG. 8B is an illustration diagram of a single constriction channel of a microfluidic system depicting depth, width, and length.

FIG. 8A is a schematic diagram of an embodiment of a microfluidic system illustrating a single constriction channel 105. FIG. 8B is an illustration diagram of a single constriction channel 105 of a microfluidic system depicting depth, width, and length. A cell passes through the constriction point 107, which introduces transient membrane disruptions (e.g., holes) in the cell membrane. The cell travels through an electric field generated by two electrodes 110 and a payload, such as DNA is delivered to the cell cytoplasm.

General Definitions and General Techniques

Unless specifically defined otherwise, all technical and scientific terms used herein shall be taken to have the same meaning as commonly understood by one of ordinary skill in the art (e.g., in cell culture, molecular genetics, and biochemistry).

Although a few variations have been described in detail above, other modifications or additions are possible. For example, the current subject matter is not limited to DNA and RNA, but can deliver a broad range of material, including, nanoparticles, protein, quantum dots, and DNA, to almost any kind cell type, at high throughput. In certain embodiments, DNA or RNA can incorporate modified nucleotides, such as those with chemical modifications to the 2'-OH group in the ribose sugar backbone, such as 2'-O-methyl (2'OMe), 2'-fluoro (2'F) substitutions, and those containing 2'OMe, or 2'F, or 2'-deoxy, or "locked nucleic acid" (LNA) modifications.

In the descriptions herein and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," herein and in the claims is intended to mean, "based at least in part on," such that an unrecited feature or element is also permissible.

As used herein, the terms "about" and "substantially" in the context of a numerical value or range means±10% of the numerical value or range recited or claimed, unless the context requires a more limited range.

As used herein, a "duty cycle" means the ratio of pulse duration over the period of the pulse.

Taken in its broadest sense, "Disruption and Field Enabled Delivery" or "DFE" means the combination of squeeze and contact with an energy field for delivering a payload into a cell.

The terms "plasma membrane" and "cell membrane" are used interchangeably herein, and refer to the semipermeable membrane that separates the interior of a cell from the environment outside the cell.

As used herein, an "expression vector" is a DNA or RNA vector that is capable of effecting expression of one or more polynucleotides. Preferably, the expression vector is also capable of replicating within the host cell. Expression vectors can be either prokaryotic or eukaryotic, and are typically plasmids. Expression vectors of the present invention include any vectors that function (i.e., direct gene expression) in host cells of the present invention, including in one of the prokaryotic or eukaryotic cells described herein, e.g., gram-positive, gram-negative, pathogenic, non-pathogenic, commensal, cocci, *bacillus*, or spiral-shaped bacterial cells; archaeal cells; or protozoan, algal, fungi, yeast, plant, animal, vertebrate, invertebrate, arthropod, mammalian, rodent, primate, or human cells. Expression vectors of the present invention contain regulatory sequences such as transcription control sequences, translation control sequences, origins of replication, and other regulatory sequences that are compatible with the host cell and that control the expression of a polynucleotide. In particular, expression vectors of the present invention include transcription control sequences. Transcription control sequences are sequences which control the initiation, elongation, and termination of transcription. Particularly important transcription control sequences are those which control transcription initiation such as promoter, enhancer, operator and repressor sequences. Suitable transcription control sequences include any transcription control sequence that can function in at least one of the cells of the present invention. A variety of such transcription control sequences are known to those skilled in the art. In preferred embodiments, the methods do not comprise the use of viral vectors such as adenoviruses to deliver nucleic acid molecules or constructs.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to 5.0 mg.

Embodiments of the invention provide techniques for applying controlled deformation to a cell for a predetermined amount of time in order to cause perturbations in the cell membrane such that materials can be delivered to the inside of the cell. The deformation can be caused by, for example, pressure induced by mechanical strain or shear forces. In one example, a microfluidic system includes a structure that controls and/or manipulates fluids by geometrically confining the fluids on a small scale (eg., sub milliliter volumes such as microlitres, nanoliters, or picoliters). The microfluidic system is capable of intracellularly delivering virtually any payload into a cell. The system consists of one or more microfluidic channels with a constriction that the cells pass through. Preferably, the cells flow through the microfluidic channel suspended in a liquid medium that is pressure driven through the system. When a cell passes through the constriction, its membrane is perturbed causing temporary disruptions in the membrane and resulting in the uptake of the payload that is present in the surrounding media. The constriction is a function of the size of the target cell, but preferably on the same order or smaller than the cell diameter. Multiple constrictions can be placed in parallel and/or series. The perturbation in the cell is a breach in the cell that allows material from outside the cell to move into the cell (e.g., through a hole, tear, cavity, aperture, pore, break, gap, perforation). The perturbations (e.g., gaps or holes) created by the methods described herein are not formed as a result of assembly of protein subunits to form a multimeric pore structure such as that created by complement or bacterial hemolysins. Other embodiments are within the scope of the described subject matter.

Unless otherwise implicitly or explicitly contradicted by the context in which it is used, references to cell "squeeze" "squeezing" "deformation" and the like refer to a process used to deliver macromolecules directly into the cytosol of cells with minimal cytotoxicity. The principle underlying this approach is temporary membrane disruption by rapid mechanical deformation, or squeezing, of the target cell, which permits the uptake by diffusion of macromolecules in the fluid medium and is followed by cell membrane repair (see, e.g., U.S. Patent Application Publication No. 2014/0287509, published Sep. 25, 2014, and PCT International Patent Application No. PCT/US2015/058489, filed Oct. 30, 2015, the entire contents of each of which are incorporated herein by reference).

Mitochondrial Diseases

Mitochondrial diseases result from dysfunctional mitochondria. Mitochondrial diseases may be caused, e.g., by mutations, acquired or inherited, in mitochondrial DNA (mtDNA) or in nuclear genes that code for mitochondrial components. Diseases may also be the result of acquired mitochondrial dysfunction due to adverse effects of drugs, infections, or other environmental causes. Examples of mitochondrial diseases include mitochondrial myopathy; diabetic nephropathy; some forms of diabetes mellitus and deafness (DAD); Leber's hereditary optic neuropathy (LHON); Leigh syndrome; neuropathy, ataxia, retinitis pigmentosa, and ptosis (NARP); myoneurogenic gastrointestinal encephalopathy (MNGIE); Myoclonic Epilepsy with Ragged Red Fibers (MERRF); mitochondrial myopathy, encephalomyopathy, lactic acidosis, stroke-like symptoms (MELAS); and mitochondrial neurogastrointestinal encephalomyopathy (MNGIE).

Delivering compounds to mitochondria is particularly difficult and unpredictable. Mitochondria are present within cells and also have their own outer (and internal) membranes. Treatment options for mitochondrial diseases, as well as tools for altering mitochondrial function or labeling mitochondria in living cells, have been limited (Marriage et al., J Am Diet Assoc (2003) 103 (8): 1029-38; Kolesnikova et al., Hum. Mol. Genet. (2004) 13(20): 2519-2534).

Figure 21A:
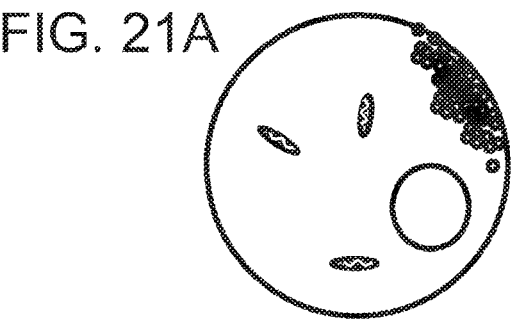
FIG. 21A-C is a cartoon illustrating the distribution of DNA delivered using (A) electroporation, (B) cell squeeze alone, and (C) DFE. See also FIG. 12A-C.
Figure 21B:
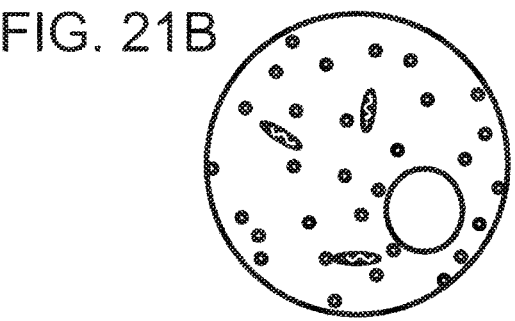
Figure 21C:
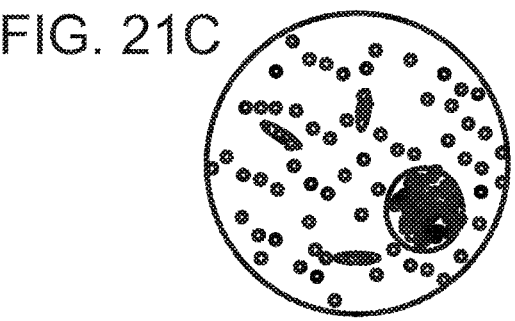

Aspects of the present invention relate methods for preventing or treating a mitochondrial disease involving the delivery of compounds (such as nucleic acids) to mitochondria. In some embodiments, a nucleic acid construct is delivered to a fertilized or unfertilized egg that contains dysfunctional mitochondria using a device and/or method described herein. In other embodiments, a nucleic acid construct is delivered to a circulating cell (such as an immune cell) that has been obtained from the blood of a subject and contains dysfunctional mitochondria. Constructs delivered to cells with dysfunctional mitochondria may, e.g., contain a recombinant gene that expresses a mitochondrial protein that is not produced, produced at a deficient level, or that is defective in the dysfunctional mitochondria. As shown in FIG. 21, nucleic acids delivered using DFE reach both the nucleus and mitochondria. In preferred embodiments, a nucleic acid is delivered directly to dysfunctional mitochondria in a cell.

Aspects of the present invention also relate to the delivery of compounds to for studying mitochondrial disease and/or function. For example, antibodies, organic molecules, or other compounds that modulate mitochondrial function and/or label mitochondria may be delivered to a cell using the devices and methods described herein.

Electric Field

Aspects of the present invention relate to the use of lower electrical field strength, or a shorter exposure to an electric field, compared to standard or previously described electroporation parameters. Electroporation parameters have been reported for numerous cell types. See, for example, information available for the Neon® Transfection System at www.thermofisher.com/us/en/home/life-science/cell-culture/transfection/transfection—selection-misc/neon-transfection-system/neon-protocols-cell-line-data.html. See also Kim et al., (2008) *Biosens Bioelectron*, 23(9): 1353-1360, the entire content of which is incorporated herein by reference. For example, the Neon® Transfection System may use an electric field of 0.3-1 kv/cm with a pulse duration of 5 ms-50 ms. Exemplary electroporation parameters for Neon® Transfection System are also provided in the table below.

Electroporation Parameters for Human Cell Types

| Cell Type | Pulse Voltage (V) | Pulse Width (ms) | Pulse Number | Transfection Efficiency | Viability |
|---|---|---|---|---|---|
| HeLA (cervical carcinoma) | 1,005 | 35 | 2 | 90% | 87% |
| Jiyoye (Lymphoblast) | 1,400 | 30 | 1 | 73% | 65% |
| BJAB (EBV-negative Burkitt's lymphoma) | 1,350 | 40 | 1 | 70% | 80% |
| IM-9 (Lymphoblast) | 1,700 | 20 | 1 | 80% | 80% |
| K-562 (CML-derived B cell-like) | 1,000 | 50 | 1 | 83% | 90% |
| LCL (EBV-transformed B cells) | 1,350 | 30 | 1 | 80% | 80% |
| Dendritic | 1,500 | 30 | 1 | 50% | 70% |
| Macrophage | 1,900 | 30 | 1 | 60% | 60% |
| PMBC (peripheral blood mononuclear cell) | 2,150 | 20 | 1 | 23% | 95% |
| Jurkat (immune, T cell leukemia) | 1,350 | 10 | 3 | 94.2% | 97.7% |
| IMR-90 (Fibroblast) | 1,100 | 30 | 1 | 88% | 88% |
| Saos-2 (Epithelial) | 1,200 | 40 | 1 | 80% | 74% |
| U-2 OS (cartilage; osteosarcoma) | 1,230 | 10 | 4 | 82% | 72% |
| MH7A (rheumatoid synovial cells) | 880 | 35 | 2 | 62% | 85% |
| BJ (Fibroblast) | 1,650 | 20 | 1 | 92% | 90% |
| HT-1080 (bone/cartilage) | 950 | 50 | 1 | 85% | 70% |
| HUVEC (endothelial) | 1,350 | 30 | 1 | 80% | 70% |
| U-87 MG (glioblastoma) | 1,300 | 30 | 1 | 70% | 70% |
| T98G (glioblastoma multiforme) | 1,200 | 30 | 1 | 75% | 70% |
| SH-SY5Y (neural/blastoma) | 1,100 | 50 | 1 | 64% | 70% |
| SW-13 (adenocarcinoma) | 800 | 60 | 1 | 56% | 80% |
| SV40 MES 13 (Myofibroblast-like) | 1,450 | 20 | 2 | 89% | 83% |
| BC-1 (Lymphoblast) | 1,600 | 10 | 3 | 75% | 60% |

Fields for Driving Compounds and Compositions into Cells

DFE leads to more efficient and more rapid delivery (and subsequent function, e.g., expression of encoded gene products) of nucleic acids with increased cell viability compared to standard or previously-disclosed electroporation systems. The present invention provides methods, systems, and devices in which an energy field such as an electrical field drives a payload through perturbations in a cell membrane caused by a cell-deforming constriction or that drives the payload from one location in the cell to another, e.g., from proximity to the cell membrane to one or more organelles. While some example implementations use electric fields, other driving mechanisms are useful. For example, one or more of electric fields, magnetic fields, and acoustic fields may serve as a driving mechanism.

As used herein, electrode refers to any electrical conductor that may be configured to have a charge and create an electric field. Some implementations may include alternative methods and/or structures that generate an electric and/or magnetic field.

In some embodiments of the invention, an electric field is used to drive a payload into a cell. It will be understood that persons skilled in the art of electrical engineering will be familiar with a variety of ways of generating electric fields. Examples of electric fields are provided throughout the summary and description of the invention; however none of these descriptions should be interpreted as limiting. For example the electric field may be produced by electrodes or by means other than electrodes. Electric fields that are constant or pulsed are contemplated for use in embodiments of the invention. An electric field may be a constant or pulsed direct electric current.

In other embodiments of the invention, a magnetic field is used to drive a payload into a cell. A magnetic field can be generated to impart a force on the payload of the cell as it moves through the magnetic field. A magnetic field can be created, for example, by an electromagnet, which can include a coil of insulated wire wrapped around an iron core. A magnetic field can also be created by a permanent magnetic, for example, from ferromagnetic materials.

In magnetofection, a magnetic field may concentrate magnetic particles on the surface of cells to enhance an endocytosis-like process for intracellular delivery. In preferred embodiments, the intensity of the magnetic field is lower than necessary for magnetofection. In some embodiments, involving a magnetic field, the magnetic field strength is 0.01 T to 10 T. The strength of the magnetic field may vary based on a number of factors, including the magnetic properties of a payload. In a non-limiting example, a field gradient can be created of between 1 and 1000 $T/m^{-1}$.

In additional embodiments of the invention, an acoustic field is used to drive a payload into a cell. For example, a cell may be contacted with an acoustic field after exiting a cell-deforming constriction of the invention. An acoustic field can be generated, for example, by a speaker, transducer, or other similar device. Speakers are transducers that convert electromagnetic waves into sound waves. The speakers may receive audio input from a device such as a computer or an audio receiver. This input may be either in analog or digital form. Analog speakers may simply amplify the analog electromagnetic waves into sound waves. Since sound waves are produced in analog form, digital speakers must first convert the digital input to an analog signal, then generate the sound waves. Acoustic waves can be generated at varying frequencies and amplitudes. In some implementations, alternating low-pressure and high-pressure waves in the buffer or other liquid leads to the formation and collapse of small vacuum bubbles, which can be referred to as cavitation. Cavitation causes high speed impinging liquid jets and strong hydrodynamic shear-forces, which may be used to manipulate payloads and cells. In some embodiments, sonication is used to generate an acoustic field.

In some embodiments relating to an acoustic field, the acoustic energy intensity may be, e.g., 1-1000 $J/cm^2$. However, the energy used may be lower or higher than this range depending on factors such as exposure time, cell type, solution or buffer used, cavitation size, etc. Non-limiting examples of frequency include 10 KHz-10 MHz.

In other embodiments of the invention, an optical field is used to drive a payload into a cell. For example, visible electromagnetic radiation may be used to drive material into a cell after the cell exits a cell-deforming constriction of the invention. Examples of sources of visible electromagnetic radiation include light-emitting diodes (LEDs), lasers, and incandescent lightbulbs.

CAR T Cells

By modifying T cells to express a chimeric antigen receptor (CAR) that recognizes cancer-specific antigens, one can prime the cells to recognize and kill tumor cells that would otherwise escape immune detection. The process involves extracting a patient's T cells, transfecting them with a gene for a CAR, then reinfusing the transfected cells into the patient.

These artificial T cell receptors (also known as chimeric T cell receptors, chimeric immunoreceptors, or CARs) are engineered receptors, which graft an arbitrary specificity onto an immune effector cell. Typically, these receptors are used to graft the specificity of a monoclonal antibody onto a T cell. Prior to the invention, transfer of nucleic acid coding sequence was typically facilitated by retroviral vectors. The methods described herein do not utilize or encompass viral vectors. The coding sequence or protein CAR is delivered to the cytosol of an immune cell such as a T cell using cell squeezing with the described device without the need for a viral vector.

For therapeutic applications, a patient's T cells are obtained (and optionally enriched or purified) from peripheral blood and modified to express an artificial (chimeric) receptor specific for a particular cancer-associated antigen. After the modification, the T cells recognize and kill cancer. For example, an exemplary CAR recognizes CD19, an antigen expressed in B-cell—blood malignancies. After the T cells have been modified to express the CAR, the modified T cells are reinfused into the patient. The engineered cells recognize and kill cancerous cells. Such therapy has been used for ALL, non-Hodgkin's lymphoma, and chronic lymphocytic leukemia (CLL), and is appropriate for therapy for any type of cancer, including blood-born cancers such as leukemias, B-cell malignancies (e.g., acute lymphoblastic leukemia (ALL) and chronic lymphocytic leukemia), as well as solid cancers. The cell processing methods described herein represent a superior process for generating CAR T cells.

In some embodiments the patient is a human. In other embodiments, the patient is other than a human.

Exemplary Embodiments

Aspects of the present invention provide a microfluidic system for causing perturbations in a cell membrane, the system comprising: a microfluidic channel defining a lumen and being configured such that a cell suspended in a buffer can pass therethrough, wherein the microfluidic channel includes a cell-deforming constriction, wherein a diameter of the constriction is a function of the diameter of the cell; and (a) an energy field; or (b) a source or emitter of an energy field positioned downstream, upstream, or upstream and downstream of said constriction.

Aspects of the present invention also provide a microfluidic system for delivery of a payload to a cell, the system comprising: a microfluidic channel defining a lumen and being configured such that a cell suspended in a buffer can pass therethrough, wherein the microfluidic channel includes a cell-deforming constriction, wherein a diameter of the constriction is a function of the diameter of the cell; and (a) an energy field; or (b) a source or emitter of an energy field positioned downstream of said constriction.

In some embodiments, said energy field comprises an electrical field and said source emitter comprises an electrode. In certain embodiments, said energy field comprises a magnetic field and said source or emitter comprises a magnet or electromagnet. In various embodiments, said energy field comprises (a) an acoustic field and said source or emitter comprises a speaker, or (b) an optical field and said source or emitter comprises a light-emitting diode (LED), laser, or incandescent lightbulb.

In various embodiments, (a) the diameter of the constriction is selected to induce temporary perturbations of the cell membrane large enough for a payload to pass through, and the cell passes through the constriction to the field in a continuous flow, wherein after passing through said constriction the cell contacts or passes through a portion of the field whose strength is sufficient to drive a payload though a temporary perturbation; or (b) after passing through said constriction the cell enters into and remains within a zone of said device that is downstream of said constriction, wherein cells within the zone are contacted with the field.

In certain embodiments, the microfluidic channel is one of a plurality of parallel microfluidic channels in the microfluidic system, each microfluidic channel of the plurality of parallel microfluidic channels defining a lumen and being configured such that a cell suspended in a buffer can pass therethrough, wherein each microfluidic channel includes a cell-deforming constriction, wherein a diameter of the constriction is a function of the diameter of the cell.

In some embodiments, the plurality of parallel microfluidic channels comprises at least about 2, 5, 10, 20, 25, 30, 40, 45, 50, 75, 100, 500, 1,000, or 2-1,000 microfluidic channels.

In various embodiments, the diameter of the constriction is selected to induce temporary perturbations of the cell membrane large enough for a payload to pass through.

In certain embodiments, the electrode includes two electrodes generating an electric field to drive a payload into the cell suspended in the buffer.

In some embodiments, the payload comprises one or more of (a) Deoxyribonucleic acid (DNA); (b) Ribonucleic acid (RNA); (c) DNA or RNA comprising one or more modified nucleotides that increase the stability or half-life of the DNA or RNA in vivo or in vitro; (d) peptide nucleic acid (PNA); (e) methylated DNA; (f) a naturally occurring chromosome or a portion thereof; (g) an expression vector; (h) a protein; (i) a small molecule; (j) a sugar; (k) polymers of biological, synthetic, organic, or inorganic molecules; (l) a charged molecule or composition comprising a charged molecule; or (m) an uncharged molecule. For example any one of or any mixtures of (a) through (m) may be delivered to a cell. In certain embodiments, the payload is a polypeptide comprising a localization signal.

In various embodiments, a microfluidic system of the invention may further include a plurality of electrode pairs in which electrode size varies between electrode pairs.

In some embodiments, a microfluidic system comprises (a) a plurality of electrodes configured into at least a first and a second array of electrodes, wherein the first array of electrodes is offset from the second array of electrodes, or (b) a plurality of electrode pairs configured into at least a first and a second array of electrode pairs, wherein the first array of electrode pairs is offset from the second array of electrode pairs. In various embodiments, the first array is offset from the second array at an angle of about 1, 5, 10, 15, 20, 25, 30, 35, 40, 45, 50, 55, 60, 70, 80, 90, 1-10, 1-20, 1-30, 1-45, or 1-90° in a horizontal, vertical, or diagonal plane.

In certain embodiments, a microfluidic system of the invention further includes a function generator coupled to the at least one electrode and driving the at least one electrode to generate an electric field for driving a payload into the cell suspended in the buffer after the cell is contracted by the cell-deforming constriction; or a function generator driving the at least one electrode via induction to generate an electric field for driving a payload into the cell suspended in the buffer after the cell is contracted by the cell-deforming constriction.

In some embodiments, the function generator is configured drive the at least one electrode to generate an electric field having an intensity of about 0.1-0.5, 0.1-1, 0.1-1.5, 0.1-2, 0.1-2.5, 0.1-3 kV/cm, 1-3 kV/cm, 0.1-10 kV/cm, 10-200 kV/m, or 10-2000 kV/m.

In various embodiments, a microfluidic system of the invention comprises a cell driver to drive the cell under pressure through the cell-deforming constriction.

In certain embodiments, a fluid flow of the cell suspended in the buffer is channeled into the constriction such that the cell is primarily compressed by the fluid flow.

In some embodiments, the diameter of the constriction is about 20-99% of the diameter of the cell passing therethrough.

In certain embodiments, the diameter of the constriction is about 4, 5, 6, 7, 8, 9, 10, 15, 20 4-10 μm, or 10-20 μm and/or the length of the constriction is about 10, 15, 20, 24, 30, 40, 50, 60, 10-40, 10-50, 10-60, or 10-40 μm.

In various embodiments, said microfluidic channel comprises a single cell-deforming constriction or multiple cell-deforming constrictions in series.

In some embodiments, the cell is contacted with the electric field about 0.0001, 0.001, 0.002, 0.003, 0.004, 0.005, 1, 2, 3, 4, 5, 6, 7, 8, 9, 10, 0.001-0.005, or 0.0001-10 seconds after exiting the cell-deforming constriction, or within about 0.0001, 0.001, 0.002, 0.003, 0.004, 0.005, 0.01, 1, 2, 3, 4, 5, 6, 7, 8, 9, 10, 0.001-0.005, or 0.0001-10 seconds after exiting the cell-deforming constriction.

In certain embodiments, the electric field has an intensity of about 0.1-0.5, 0.1-1, 0.1-1.5, 0.1-2, 0.1-2.5, 0.1-3 kV/cm, 1-3 kV/cm, 0.1-10 kV/cm, 10-200 kV/m, or 10-2000 kV/m.

Aspects of the present invention provide a method for delivering a compound or composition into a cell, the method comprising: providing a cell in a payload-containing solution; passing the solution through a microfluidic channel that includes a cell-deforming constriction; passing the cell through the constriction such that a pressure is applied to the cell causing perturbations of the cell membrane large enough for a payload to pass through the cell membrane and into the cytosol of the cell; contacting the cell with an electric field, a magnetic field, an acoustic field, or an optical field that translocates the payload from a first location in the cell to a second location inside the cell.

Aspects of the present invention also provide a method for delivering a compound or composition into a cell, the method comprising: providing a cell in a payload-containing solution; passing the solution through a microfluidic channel that includes a cell-deforming constriction; passing the cell through the constriction such that said passage leads to perturbations of the cell membrane large enough for a payload to pass through the cell membrane and into the cytosol of the cell; contacting the cell with an electric field, a magnetic field, an acoustic field, or an optical field that translocates the payload from a first location in the cell to a second location inside the cell.

Aspects of the present invention provide a method for delivering a compound or composition into a cell, the method comprising: providing a cell in a payload-containing solution; passing the solution through a microfluidic channel that includes a cell-deforming constriction; passing the cell through the constriction such that a pressure is applied to the cell causing perturbations of the cell membrane large enough for a payload to pass through the cell membrane and into the cytosol of the cell; contacting the cell with an electric field, a magnetic field, an acoustic field, or an optical field that drives the payload into the cell.

In some embodiments, the cell is contacted with a magnetic field, and the magnetic field is generated by at least one electromagnet. In various embodiments, the cell is contacted with an electric field, and the electric field is generated by one or more electrodes.

In certain embodiments, the cell is passed through the microfluidic channel in a first device and then removed from the first device and contacted with the electric field, the magnetic field, or the acoustic field in a second device.

In various embodiments, the microfluidic channel and the electric field, the magnetic field, and the acoustic field are within one device.

In some embodiments, (a) the cell passes through the constriction to the field in a continuous flow, wherein after passing through said constriction, the cell contacts or passes through a portion of the field whose strength is sufficient to drive a payload though a temporary perturbation; or (b) after passing through the constriction the cell flows into and remains within a zone of the device where the cell is contacted with the field.

In certain embodiments, the cell is a plurality of cells, and each cell is passed through one of a plurality of parallel microfluidic channels, wherein each microfluidic channel of the plurality of parallel microfluidic channels includes a cell-deforming constriction, and wherein the plurality of cells is passed through the electric field.

In various embodiments, the diameter of the constriction is selected to induce temporary perturbations of the cell membrane large enough for the payload to pass through when driven by the electric field.

In some embodiments, the payload comprises one or more of (a) Deoxyribonucleic acid (DNA); (b) Ribonucleic acid (RNA); (c) DNA or RNA comprising one or more modified nucleotides that increase the stability or half-life of the DNA or RNA in vivo or in vitro; (d) peptide nucleic acid (PNA); (e) methylated DNA; (f) a naturally occurring chromosome or a portion thereof; (g) an expression vector; (h) a protein; (i) a small molecule; (j) a sugar; (k) polymers of biological, synthetic, organic, or inorganic molecules; (l) a charged molecule or composition comprising a charged molecule; or (m) an uncharged molecule. For example any one of or any mixtures of (a) through (m) may be delivered to a cell. In certain embodiments, the payload is a polypeptide comprising a localization signal.

In certain embodiments, the cell is contacted with an electric field, and the payload is driven into one or more of (a) the nucleus of the cell; (b) a mitochondrion of the cell; or (c) an organelle of the cell other than the nucleus or a mitochondrion of the cell.

In various embodiments, the cell is contacted with an electric field, and the payload is driven into the nucleus of the cell while the cell passes through the electric field, or less than 0.1, 0.5, 1, 1.5, 2, 2.5, 3, 3.5, 4, or 0.1-48 hours after the cell passes through the electric field.

In some embodiments, the cell is a plurality of cells and the payload is DNA that is expressed when in a cell nucleus, and wherein at least about 10, 20, 25, 30, 35, 40, 45, 50, 55, 60, 65, 70, 75, 80, 85, 90, 95, 99, 100, 0-65, or 10-100% of the plurality of cells express the DNA within about 0.1, 0.5, 1, 1.5, 2, 2.5, 3, 3.5, 4, 0.1-4, or 0.1-48 hours after the plurality of cells passes through the electric field.

In certain embodiments, the electric field is generated by two electrodes to drive the payload into the cell suspended in the buffer.

In various embodiments, the electric field is generated by a plurality of electrode pairs in which electrode size varies between electrode pairs.

In some embodiments, at least one electrode is driven by a function generator coupled to the electrode, the function generator driving the electrode to generate the electric field for driving the payload into the cell suspended in the buffer after the cell is contracted by the cell-deforming constriction.

In certain embodiments, a fluid flow of the cell suspended in the buffer is channeled into the constriction such that the cell is primarily compressed by the fluid flow.

In some embodiments, the diameter of the constriction is about 20-99% of the diameter of the cell passing therethrough. In some embodiments, the diameter of the constriction is about 4, 5, 6, 7, 8, 9, 10, 15, 20 4-10 μm, or 10-20 μm. In some embodiments, the length of the constriction is about 10, 15, 20, 24, 30, 40, 50, 60, 10-40, 10-50, 10-60, or 10-40 μm. In some embodiments, the cell is contacted with the electric field about 0.0001, 0.001, 0.002, 0.003, 0.004, 0.005, 1, 2, 3, 4, 5, 6, 7, 8, 9, 10, 0.001-0.005, or 0.0001-10 seconds after exiting the cell-deforming constriction, or within about 0.0001, 0.001, 0.002, 0.003, 0.004, 0.005, 1, 2, 3, 4, 5, 6, 7, 8, 9, 10, 0.001-0.005, or 0.0001-10 seconds after exiting the cell-deforming constriction. In some embodiments, the exposure time of the cell to the electric field is about 10-50 ms, 50-100 ms or 10-100 ms. In some embodiments, the electric field is constant. In some embodiments, the electric field is a constant or pulsed direct electric current. In some embodiments, the electric field is pulsed. In some embodiments, the electric field is pulsed at about 50-200 μs. In some embodiments, the strength or the pulse strength of the electric field is about 1-3 kV/cm or 0.1-10 kV/cm, or 0.1 to 0.5, 0.1 to 1, 0.1 to 1.5, 0.1 to 2, 0.1 to 2.5, or 0.1 to 3 kV/cm. In some embodiments, the strength or pulse strength of the electric field is less than the strength necessary to electroporate the cell. In some embodiments, the pulse width is less than the pulse width necessary to deliver the same amount of payload to a corresponding cell. In some embodiments, the strength or pulse strength of the electric field is about 50, 1-50, 50-99, or 1-99% less than the strength necessary to electroporate the cell. In some embodiments, a pressure of about 10-35 psi is used to pass the solution through the microfluidic channel. In some embodiments, the cell passes through the microfluidic channel at a speed of about 300, 100-300, 200-700, 250-400, 100-1000 mm/s, or 1-1000 mm/s. In some embodiments, said microfluidic channel comprises multiple cell-deforming constrictions in series. In some embodiments, said microfluidic channel comprises a single cell-deforming constriction. In some embodiments, the cell is a plurality of cells, and about 80, 85, 90, 91, 92, 93, 94, 95, 96, 97, 98, 99, 90-95, or 80-100% of the cells are viable after passing through the electric field. In some embodiments, the strength or the pulse strength of the electric field is about 10-2000 kV/m, or less than 100 kV/m; In some embodiments, the electric field is pulsed at a duration of about 0.1, 0.1-2, or 0.1-2000 ms, at a period of 1-20, 0.1-2000, or 1-200 ms. In some embodiments, the cell passes through the electric field at a speed of about 100, 170, 300, 100-300, 200-700, 250-400, 100-1000 mm/s, or 1-1000 mm/s. In some embodiments, the perturbations of the cell membrane include a maximum diameter of about 1-20, 1-600, 4, 5, 6, 7, 8, 9, 10, 12, 14, 16, 18, 20, 25, 50, 75, 100, 150, 200, 250, 300, 350, 400, 450, 500, or 600 nm. In some embodiments, perturbations of the cell membrane having a maximum diameter of about 1-20, 1-600, 4, 5, 6, 7, 8, 9, 10, 12, 14, 16, 18, 20, 25, 50, 75, 100, 150, 200, 250, 300, 350, 400, 450, 500, or 600 nm persist on the cell membrane for at least about 1, 2, 3, 4, 5, 6, 7, 8, 9, 10, or 1-10 minutes.

In various embodiments, the cell is a prokaryotic cell or a eukaryotic cell. In certain embodiments, the cell is a red blood cell, a T cell, a B cell, a neutrophil, a dendritic cell, a macrophage, a monocyte, a NK cell, a ILC, or any combination thereof.

Aspects of the present invention provide a method for delivering an expression vector encoding a transgene into a cell, the method comprising: passing a solution comprising the cell and the expression vector through a cell-deforming constriction such that a pressure is applied to the cell causing perturbations of the cell membrane large enough for the expression vector to pass through; passing the solution through an electric field generated by at least one electrode for driving the expression vector into the cell, wherein the transgene is expressed in the cell at a faster rate compared to expression of the transgene in a cell that was passed through an electric field without passing through a cell-deforming constriction.

In some embodiments, the transgene is expressed in the cell 0.1, 1.5, 1, 1.5, 2, 2.5, 3, 3.5, 4, or 0.1-4 hours sooner than in a corresponding cell that was contacted with an electric field without passing through a cell-deforming constriction.

Aspects of the present invention also provide a method for delivering an expression vector encoding a transgene into a cell, the method comprising: passing a solution comprising the cell and the expression vector through a cell-deforming constriction such that a pressure is applied to the cell causing perturbations of the cell membrane large enough for the expression vector to pass through; passing the solution through an electric field generated by at least one electrode for driving the expression vector into the cell, wherein the maximum expression of the transgene in the cell is achieved or detected at a faster rate compared to said expression in a cell that was passed through an electric field without passing through a cell-deforming constriction.

In some embodiments, expression of the transgene in the cell is achieved about 0.1, 1.5, 1, 1.5, 2, 2.5, 3, 3.5, 4, or 0.1-4 hours sooner than said expression in a corresponding cell that was contacted with an electric field, magnetic field, or acoustic field without passing through a cell-deforming constriction.

Aspects of the present invention also provide a method for delivering an expression vector encoding a transgene into a cell, the method comprising: passing a solution comprising the cell and the expression vector through a cell-deforming constriction such that a pressure is applied to the cell causing perturbations of the cell membrane large enough for the expression vector to pass through; passing the solution through an electric field generated by at least one electrode for driving the expression vector into the cell, wherein the transgene is expressed in the cell to a greater extent compared to expression of the transgene in a cell that was passed through an electric field without passing through a cell-deforming constriction.

In some embodiments, after the cell has passed through the constriction and is contacted by the field, the level of expression of the transgene is greater than in a corresponding cell that was passed through an electric field without passing through a cell-deforming constriction.

In various embodiments, the transgene expression in the cell is at least about 5, 10, 15, 20, 25, 30, 35, 40, 45, 50, 55, 60, 65, 70, 75, 80, 85, 90, 95, or 100% greater, or 2-fold, 5-fold, 8-fold, 10-fold, 20-fold or more greater than the expression of the transgene in a corresponding cell that was contacted with an electric field without passing through a cell-deforming constriction.

In some embodiments, within about 0.1, 1.5, 1, 1.5, 2, 2.5, 3, 3.5, 4, or 0.1-4 hours after the cell passes through the constriction, transgene expression in the cell is at least about 5, 10, 15, 20, 25, 30, 35, 40, 45, 50, 55, 60, 65, 70, 75, 80, 85, 90, 95, or 100% greater, or 2-fold, 5-fold, 8-fold, 10-fold, 20-fold or more greater than the expression of the transgene in a corresponding cell that was contacted with an electric field without passing through a cell-deforming constriction.

Aspects of the present invention provide a method for delivering an expression vector encoding a transgene into a population of cells, the method comprising: passing a solution comprising the cells and the expression vector through a cell-deforming constriction such that a pressure is applied to the cells causing perturbations of the cells large enough for the expression vector to pass through; passing the solution through an electric field generated by at least one electrode for driving the expression vector into the cells, wherein the proportion of cells expressing the transgene in the population is greater than the proportion of cells expressing the transgene in a population of cells that was passed through an electric field without passing through a cell-deforming constriction.

In some embodiments, the proportion of cells expressing the transgene in the population is at least about 5, 10, 15, 20, 25, 30, 35, 40, 45, 50, 55, 60, 65, 70, 75, 80, 85, 90, 95, or 100% greater, or 2-fold, 5-fold, 8-fold, 10-fold, 20-fold or more greater than the proportion of cells expressing the transgene in a population of corresponding cells that were contacted with an electric field without passing through a cell-deforming constriction.

In some embodiments, within about 0.1, 1.5, 1, 1.5, 2, 2.5, 3, 3.5, 4, or 0.1-4 hours after the cell passes through the constriction, the proportion of cells expressing the transgene in the population is at least about 5, 10, 15, 20, 25, 30, 35, 40, 45, 50, 55, 60, 65, 70, 75, 80, 85, 90, 95, or 100% greater, or 2-fold, 5-fold, 8-fold, 10-fold, 20-fold or more greater than the proportion of cells expressing the transgene in a population of corresponding cells that were contacted with an electric field without passing through a cell-deforming constriction.

Aspects of the present invention also provide a method for delivering an expression vector encoding a transgene into a population of cells, the method comprising: passing a solution comprising the cells and the expression vector through a cell-deforming constriction such that a pressure is applied to the cells causing perturbations of the cells large enough for the expression vector to pass through; passing the solution through an electric field generated by at least one electrode for driving the expression vector into the cells, wherein the proportion of cells expressing the transgene at a high level in the population is greater than the proportion of cells expressing the transgene at a high level in a population of cells that was passed through an electric field without passing through a cell-deforming constriction.

In certain embodiments, the proportion of cells expressing the transgene at a high level in the population is at least about 5, 10, 15, 20, 25, 30, 35, 40, 45, 50, 55, 60, 65, 70, 75, 80, 85, 90, 95, or 100% greater, or 2-fold, 5-fold, 8-fold, 10-fold, 20-fold or more greater than the proportion of cells expressing the transgene in a population of corresponding cells that were contacted with an electric field without passing through a cell-deforming constriction.

In some embodiments, within about 0.1, 1.5, 1, 1.5, 2, 2.5, 3, 3.5, 4, or 0.1-4 hours after the cell passes through the constriction, the proportion of cells expressing the transgene at a high level in the population is at least about 5, 10, 15, 20, 25, 30, 35, 40, 45, 50, 55, 60, 65, 70, 75, 80, 85, 90, 95, or 100% greater, or 2-fold, 5-fold, 8-fold, 10-fold, 20-fold or more greater than the proportion of cells expressing the transgene in a population of corresponding cells that were contacted with an electric field without passing through a cell-deforming constriction.

Aspects of the present invention provide a method for delivering an expression vector encoding a transgene into a cell, the method comprising: passing a solution comprising the cell and the expression vector through a cell-deforming constriction such that a pressure is applied to the cell causing perturbations of the cell membrane large enough for the expression vector to pass through; passing the solution through an electric field generated by at least one electrode for driving the expression vector into the cell, wherein the transgene is expressed in the cell sooner than expression of the transgene in a cell that was passed through an electric field without passing through a cell-deforming constriction.

In various embodiments, the transgene is expressed in the cell about 0.1, 1.5, 1, 1.5, 2, 2.5, 3, 3.5, 4, or 0.1-4 hours sooner than in a corresponding cell that was contacted with an electric field without passing through a cell-deforming constriction.

EXAMPLES

Example 1

Microfluidic Platform for DNA Delivery

Many techniques have been developed for DNA transfection. Carrier based methods such as lipofection heavily rely on the interaction between carrier and cell membrane, as well as the intracellular transportation of DNA, a biologically active process. Microinjection has been used to deliver DNA directly into nucleus for transcription, however, it is limited by throughput. Electroporation has been widely used for DNA transfection, however, its mechanism is still controversial and is also limited by its dependence on the active DNA transportation from plasma membrane to nucleus after electric pulse. Here a concept for intracellular delivery named disruption and field enabled delivery (DFE; this term is not limited to the embodiments of this Example) is described. In DFE, perturbations in the plasma membrane are first opened through disruption and then DNA delivery into the cytoplasm and nucleus through those gaps is enabled. This strategy relates to combining mechanical disruption and an electric field, in which cargo molecules or mixtures thereof such as GFP plasmid DNA was directly delivered into nucleus and expressed within 1 hour after treatment, which is more rapid than other methods such as electroporation. This new strategy is useful for intracellular gene delivery for difficult-to-transfect cells, and co-delivery of a wide range of materials.

Cell transfection has been essential to many studies in biology and medicine. A variety of techniques have been developed for cell transfection, including biological, chemical, and physical methods. Biological/chemical methods usually rely on carriers such as virus, vesicles, peptides or nanoparticles (Nayak et al., Gene Ther. 17, 295-304 (2010); Wu et al., Biotechnol. Progr. 18, 617-622 (2002); Schmid et al., Gut 41, 549-556 (1997); Lee et al., Nat. Nanotechnol. 7, 389-393 (2012)). Physical methods primarily use membrane-disruption techniques such as micro-injection, electroporation, laser poration, and particle bombardment for gene delivery (O'Brien & Lummis, Nature Protoc. 1, 977-981 (2006); Wells, D. J. Gene Ther. 11, 1363-1369 (2004); Meacham et al., J. Lab. Autom. 19, 1-18 (2014); Capecchi, Cell 22, 479-488 (1980); Nagy et al., Manipulating the Mouse Embryo: A Laboratory Manual (Cold Spring Laboratory, 2003)). The delivery of naked nucleic acids into cells is likely the safest and most robust approach for cell transfection (Wolff & Budker, Advances in Genetics, 54, 3-20 (2005)). Among the physical methods that can deliver naked genetic materials, electroporation is so far the most popular one due to its simplicity, reasonably good efficiency, and its ability to address certain challenging primary cells (Neumann et al., EMBO J. 1, 841-845 (1982)). Since its first report in the early 1980s, electroporation, also known as electropermeabilization, has been widely used for intracellular delivery of nucleic acids for many different cells in biological and medical applications. Although electroporation has demonstrated its advantages and been widely used for DNA transfection, its underlying mechanism of delivery is not fully understood (Escoffre et al., Mol. Biotechnol. 41, 286-95 (2009); Vasilkoski et al., Phys. Rev. E 74, 021904 (2006); Klenchin et al., Electrically induced DNA uptake by cells is a fast process involving DNA electrophoresis. 60, (1991); Weaver et al., Bioelectrochemistry 87, 236-43 (2012); Jordan et al. (Eds.) (2013) Electroporation and electrofusion in cell biology. Springer Science & Business Media). It is well accepted that in the electroporation process, DNA molecules accumulate and interact with the electropermeabilized plasma membrane during the electric pulse. Afterwards, those DNA aggregates are then internalized into the cytoplasm and subsequently lead to gene expression (Golzio et al., Proc. Natl. Acad. Sci. 99, 1292-1297 (2002); Paganin-Gioanni et al. Proc. Natl. Acad. Sci. U.S.A. 108, 10443-7 (2011); Rosazza et al. Mol. Ther. 21, 2217-2226 (2013); Boukany et al., Nat. Nanotechnol. 6, 747-54 (2011); Teissie et al., Biochim. Biophys. Acta 1724, 270-80 (2005); Yarmush et al., Annu. Rev. Biomed. Eng. 16, 295-320 (2014); Geng & Lu, Lab Chip 13, 3803-21 (2013)). It is unlikely that DNA plasmids could navigate through the viscous and crowded cytoplasm to reaches the nucleus simply by diffusion (Lechardeur et al., Adv. Drug Deliv. Rev. 57, 755-767 (2005); Dowty et al., Proc. Natl. Acad. Sci. U.S.A. 92, 4572-4576(1995)). Some work has shown that the transportation of DNA from plasma membrane to nucleus is an active biological process through cytoskeletal transport such as via microtubule and actin networks (Rosazza et al. Mol. Ther. 21, 2217-2226 (2013)). It has been found that microtubule and actin networks play an important role in DNA transportation within the cytoplasm, and the time-scale of such processes can be hours long depending on the cell type. The unclear mechanism and complex nature of DNA transfer between the plasma membrane and nucleus hinders the further application and improvement of electroporation for hard-to-transfect cells. Moreover, the strong fields used in current electroporation techniques can lead to significant damage or death (Yarmush et al., Annu. Rev. Biomed. Eng. 16, 295-320 (2014); Geng & Lu, Lab Chip 13, 3803-21 (2013)), a problem that is avoided by DFE, described herein. In this regard, there is substantial interest in creating technologies that can directly send naked DNA into the nucleus without relying on ill-defined trafficking pathways. Earlier methods or approaches are often technically complicated, have relatively low throughput and are incompatible with certain primary cells.

High Throughput, Efficient Delivery of DNA into Nucleus

The deployment of a disruption and field enabled delivery (DFE) concept is disclosed herein. In this approach, one first disrupts the cell membrane by a mechanical process before exposing the cell to a field to drive the material into the target cell. A microfluidic device that can directly deliver DNA into the nucleus of cells with high throughput has been developed. One implementation of the DFE concept involves the use of cell squeezing to disrupt the cell membrane temporarily before exposing the cell to an electrical field that drives negatively charged DNA through membrane disruptions, e.g. nuclear membrane or mitochondrial membranes, and into the cell nucleus following delivery of the carto into the cytosol of the cell. The CellSqueeze technique has demonstrated a robust ability to deliver a diversity of materials across cell types but in isolation is ineffective at facilitating nuclear delivery of DNA (Shalek et al., Proc. Natl. Acad. Sci. U.S.A. 107, 1870-5 (2010)). Unlike electroporation where DNA molecules electrophoretically migrate toward and aggregate on the plasma membrane, in a DFE process, DNA molecules migrate into the cell and/or within the cell through the perturbations or gaps in a cell membrane that are generated by mechanical disruption. See, e.g., FIG. 9A. This combination process (DFE) leads to a synergistic effect in delivery of cargo, e.g., charged compounds, e.g., DNA, to the cytosol and subcellular structures. Synergy is demonstrated by measuring function of the delivered cargo, e.g., gene expression by delivered DNA.

This example describes a unique microfluidic device that can directly deliver DNA into nucleus in high throughput by combining mechanical disruption and exposure to an electric field. Cell squeeze technique has been proved to be an efficient technique for mechanically disrupting the plasma membrane. When a cell flows through a constriction channel with minimum dimension smaller than cell diameter, the transient deformation results in the formation of holes in the plasma membrane through which surrounding materials may diffuse directly into the cell cytosol.

Figure 9A:
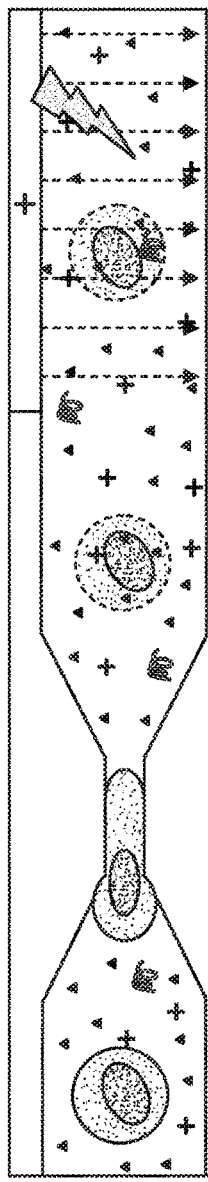
FIG. 9A-C is a depiction of a device structure and working mechanism.
Figure 9B:
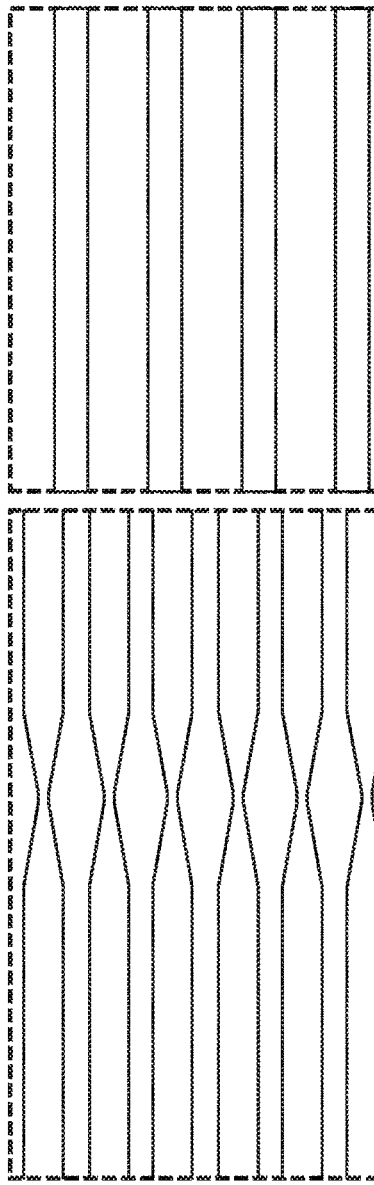
Figure 9C:
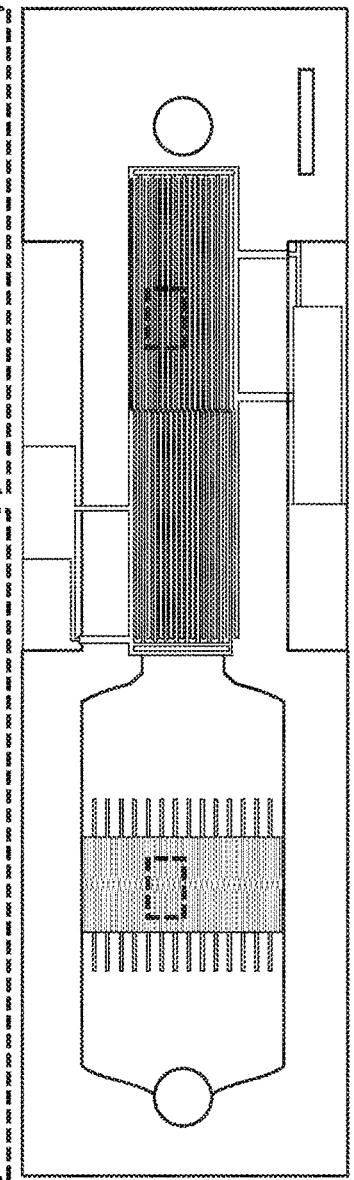

Each device is integrated by a set of parallel, identical constriction channels and a set of electrodes, as shown in FIG. 9A-C. In the experiment described in this example, 75 parallel channels were etched into a silicon wafer using DRIE (deep reactive ionic etching) and sealed by anodic bonding of Pyrex that was patterned with electrodes (see FIG. 13 for more details of fabrication). The width and length of the constriction range from 4-10 um and 10-30 um, respectively. The length, width, and gap space between each electrode is 8 mm, 60 um, and 40 um, respectively. The duration and duty cycle of the electrical pulse applied to the device range from 50-200 us and 1% -5%. Methods of the present invention may operated at a very high throughput. For example, cells may be treated at a throughput of at least about 10,000, 20,000, 30,000, 40,000, 50,000, 100,000, 200,000, 300,000, 400,000, 500,000, 1 million, or 1 to 1 million cells/s. A mixture of cell and desired materials is driven into the inlet by gas pressure, e.g., nitrogen pressure, controlled by a regulator. Electrical pulse is applied to the device when sample is placed into the device so that cells experience an electrical field right after squeeze. The exposure time of the cells in the electrical field typically ranges from 10-50 ms, depending on the flow rate.

Figures 10A, 10B:
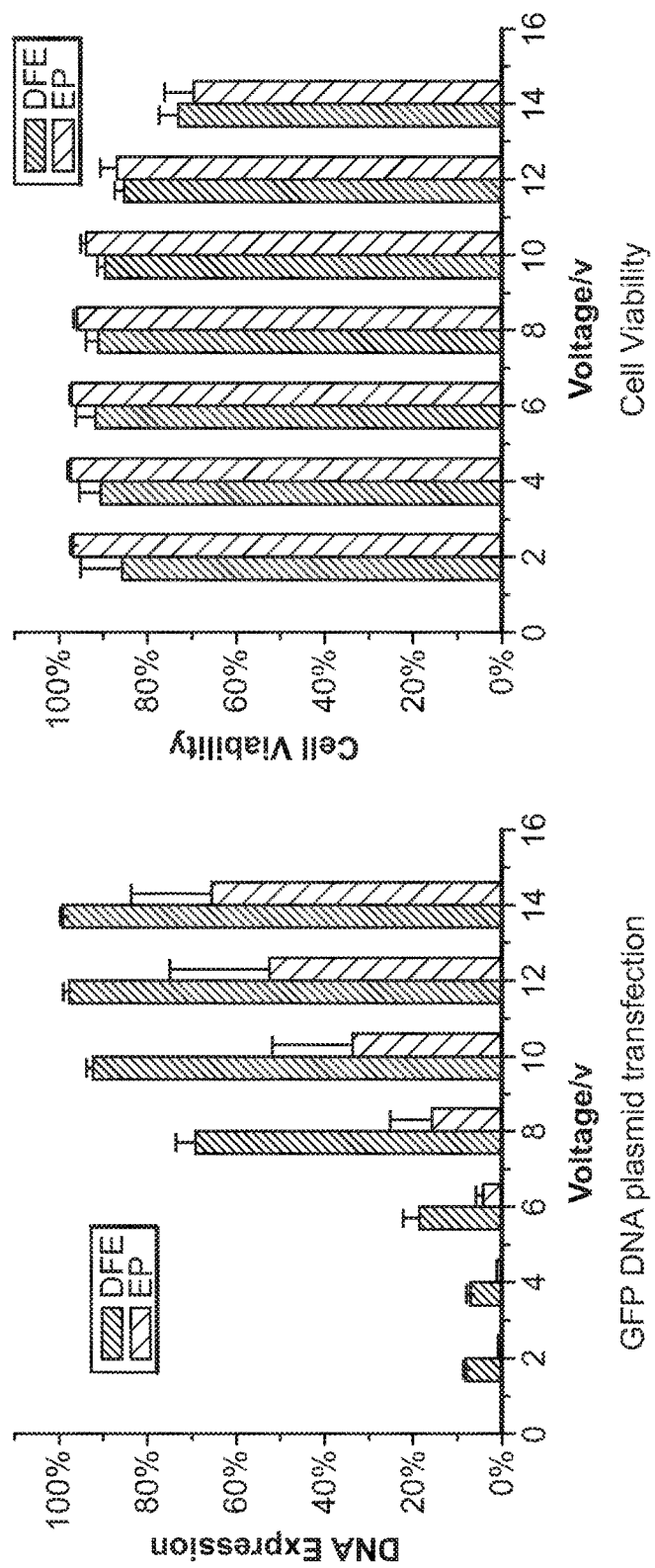
FIGS. 10A and 10B are bar graphs illustrating transfection performance that depends on electric pulse. DNA transfection efficiency (FIG. 10A) and cell viability (FIG. 10B) 24 h after treatment as a function of applied electric amplitude. The introduction of mechanical disruption prior electrotransfection significantly enhance the DNA transfection, while bringing negligible damage to cell viability. GFP plasmid DNA transfection efficiency and cell viability were measured by flow cytometry after propidium iodide staining.

To explore the working mechanism of DNA delivery, a number of experiments were carried out to characterize the performance of this DFE technique using model cells and a model cargo, as shown in FIGS. 10A and 10B. A mixture of HeLa cells and GFP plasmid DNA was treated with the DFE device using different pulse amplitudes. The cells were then incubated at 37 C for 24 hours. DNA expression was characterized by measuring GFP fluorescence using flow cytometry. A DFE 10-6 device was used in this experiment. DFE 10-6 denotes the constriction dimensions of DFE device, the first number corresponds to constriction length while the second to width (in microns). Two governing parameters that influence the performance of mechanical disruption include cell speed, and constriction dimension, and three of the parameters that govern the performance of electrical fields are the electrical pulse profile, strength, and number of pulse (depends on cell speed in the channel). How the pulse strength affects the DNA transfection was investigated first. In the DFE 10-6 treatment, cell transfection reaches above 60% and 90% when the applied amplitude increased to 8V and 10V respectively, as shown by the red columns in FIG. 10A. As a control group, cells were treated using a device with the same electrical field and cell speed but no constriction structure (in this experiment, speed, not pressure was controlled). In such a design where cells experience only an electric field but no mechanical disruption, the DNA transfection efficacy reaches 60% after the applied amplitude increased to 14V. Both cases share the similar cell viability, as shown in FIG. 10B, indicating that mechanical disruption dramatically enhances the DNA delivery at lower field intensities while bringing negligible damage to cells. The mechanical disruption of the plasma membrane facilitates the following electrotransfection process.

The influence of cell speed on the transfection was also investigated. For example, as shown in FIG. 14, under the applied pulse of 10V, the DNA expression decreases when cell speed increases due to the reduced number of pulses the cell receives as it travels through the electric field. A desirable balance between cell viability and DNA expression was achieved at cell speeds near 300 mm/s. These exemplary conditions balance the effect of potentially severe electric damage at low speed and mechanical damage at high speed. The delivery efficiency of membrane-impermeable, Cascade Blue labeled 3-kDa dextran molecules to live HeLa cells first drops and then increases with increasing cell speed indicating the potentially dominant role of delivery for this molecule switches from mechanical disruption, to electrical field and then back to mechanical disruption. The difference in behavior between the 3 kDa dextran and DNA cases further highlight the significance of the electrical field effects for DNA.

Figure 11A:
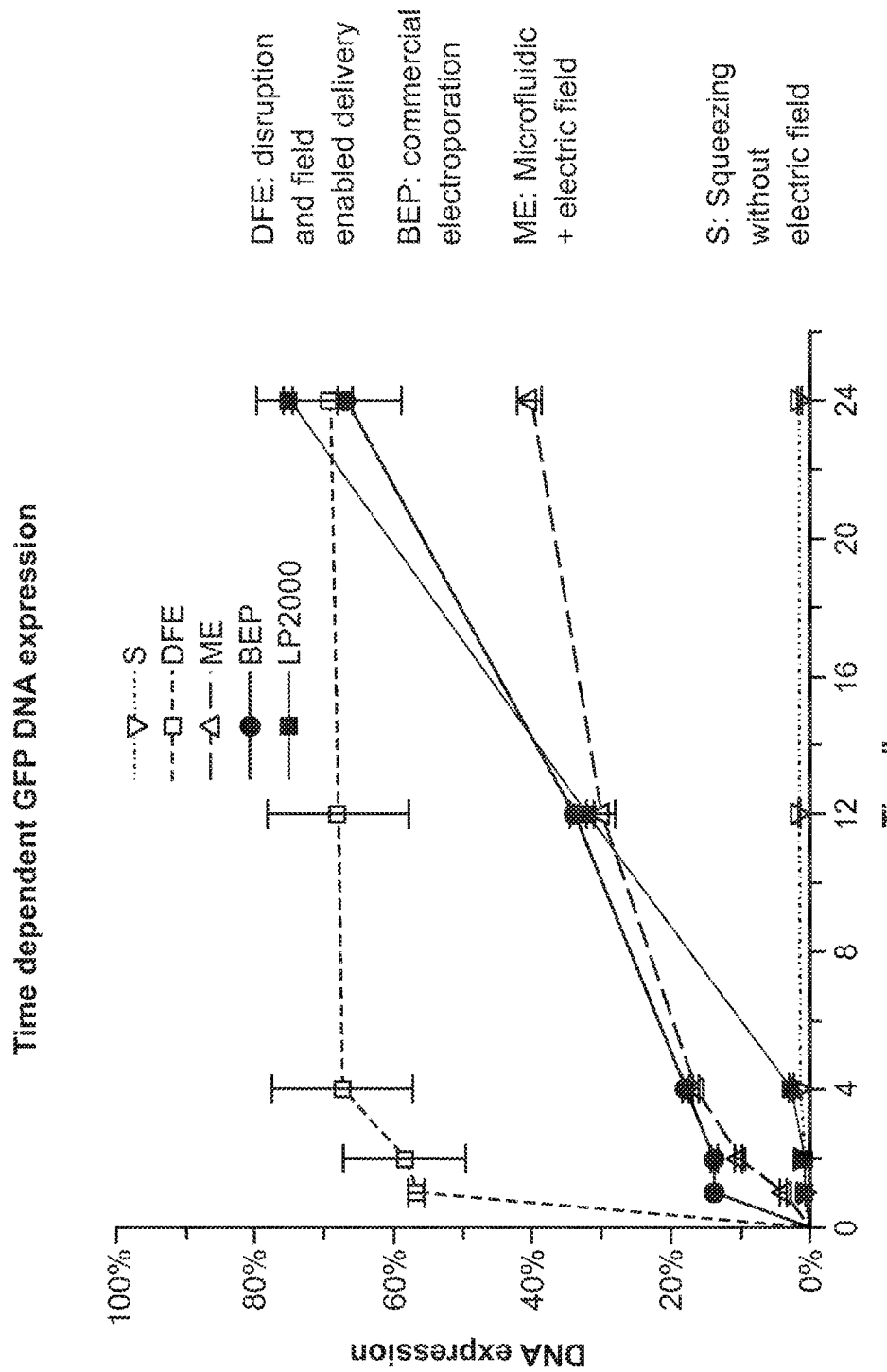
FIG. 11A-C are graphs showing results from a comparison study of Plasmid DNA transfection to HeLa cells using different methods.
Figure 11B:
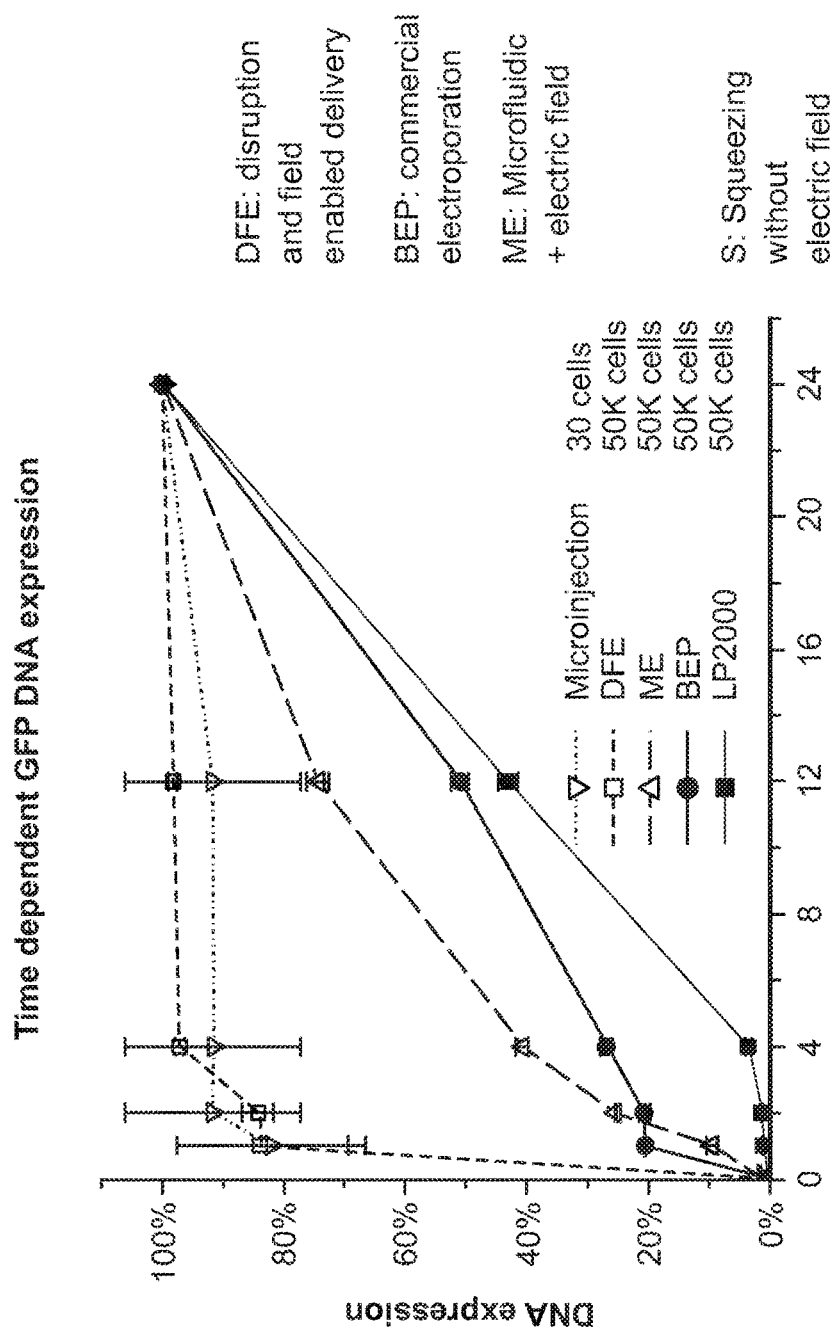
Figure 11C:
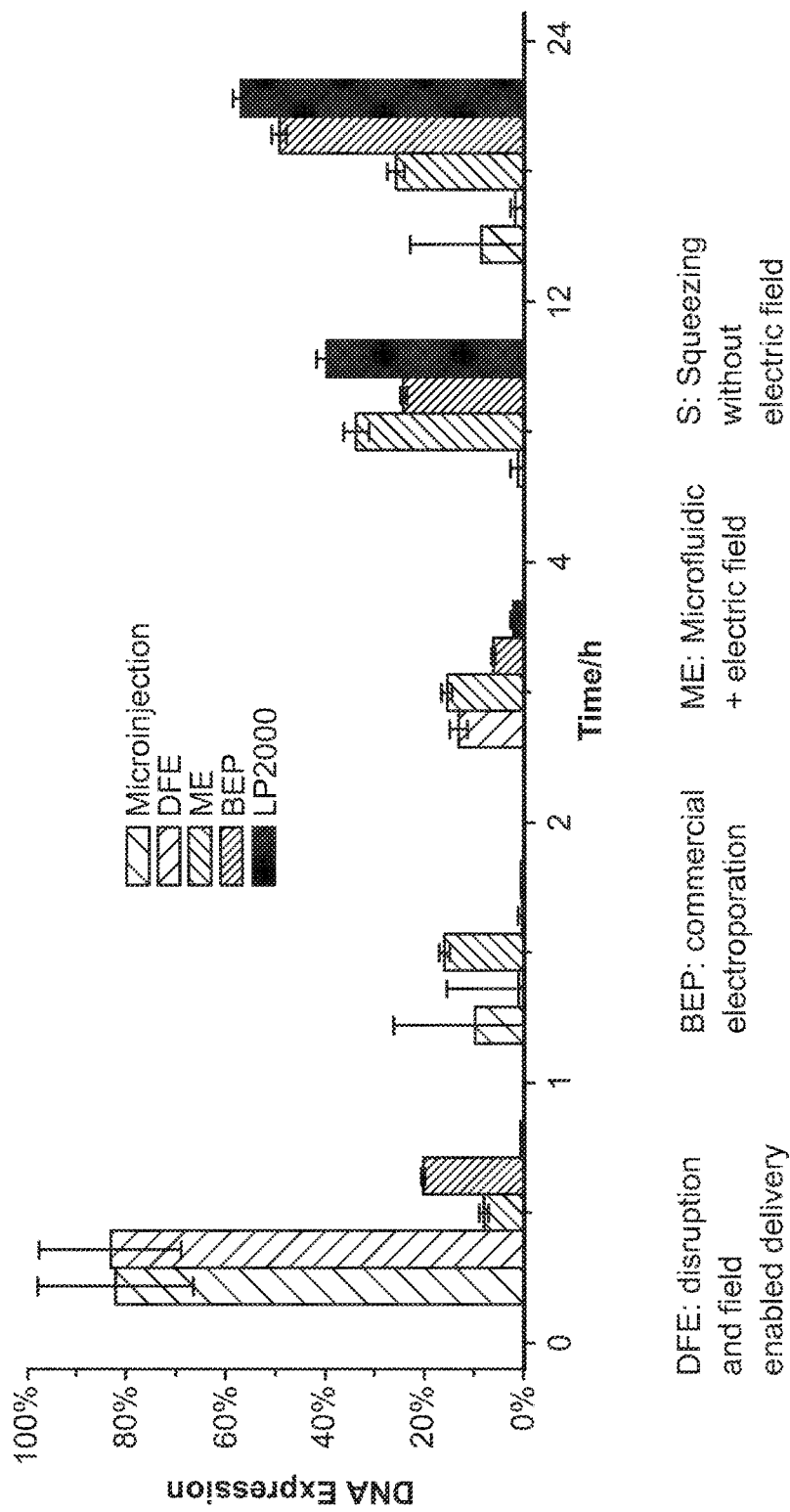
Figure 15A:
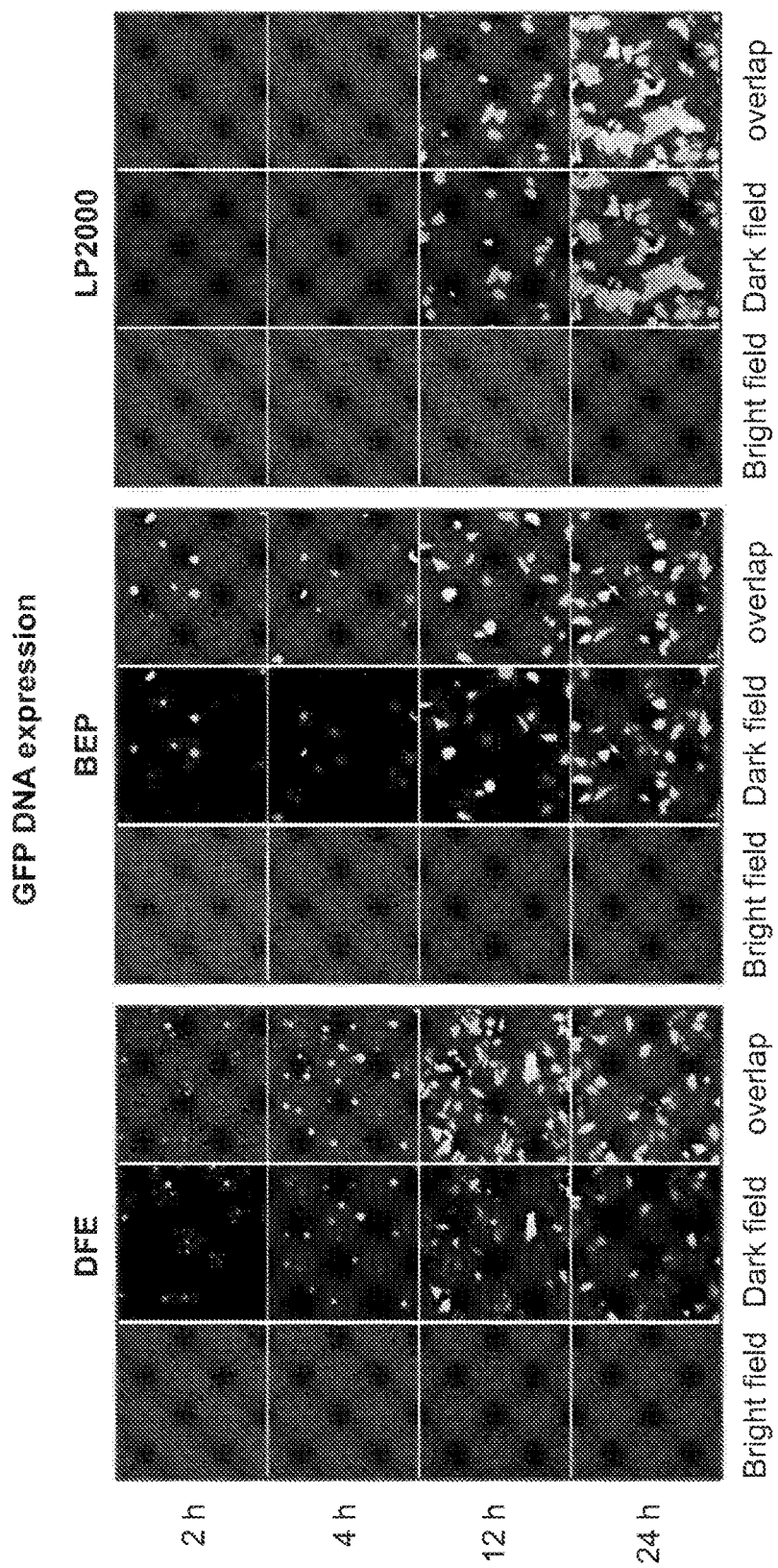
FIGS. 15A and B shows fluorescence images of HeLa cells.
Figure 15B:
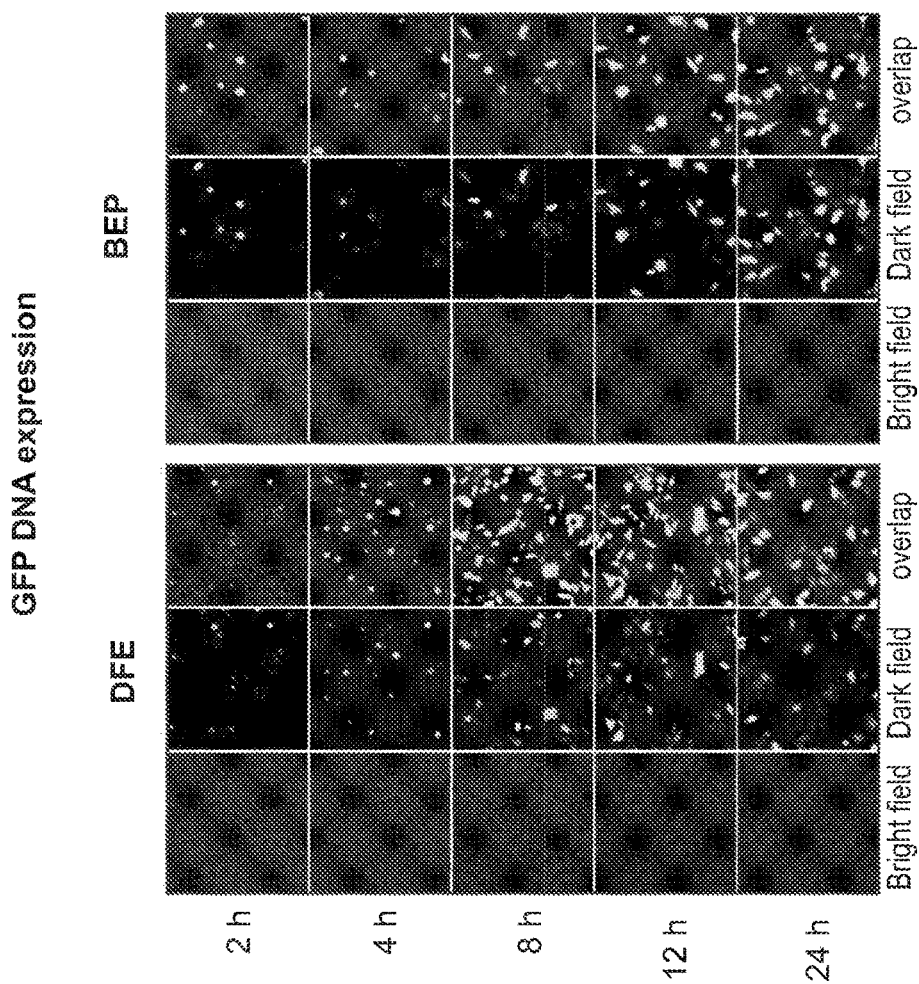
(FIG. 15B) Shows the comparison of DFE and BEP including an 8 hour time point.
Figure 16A:
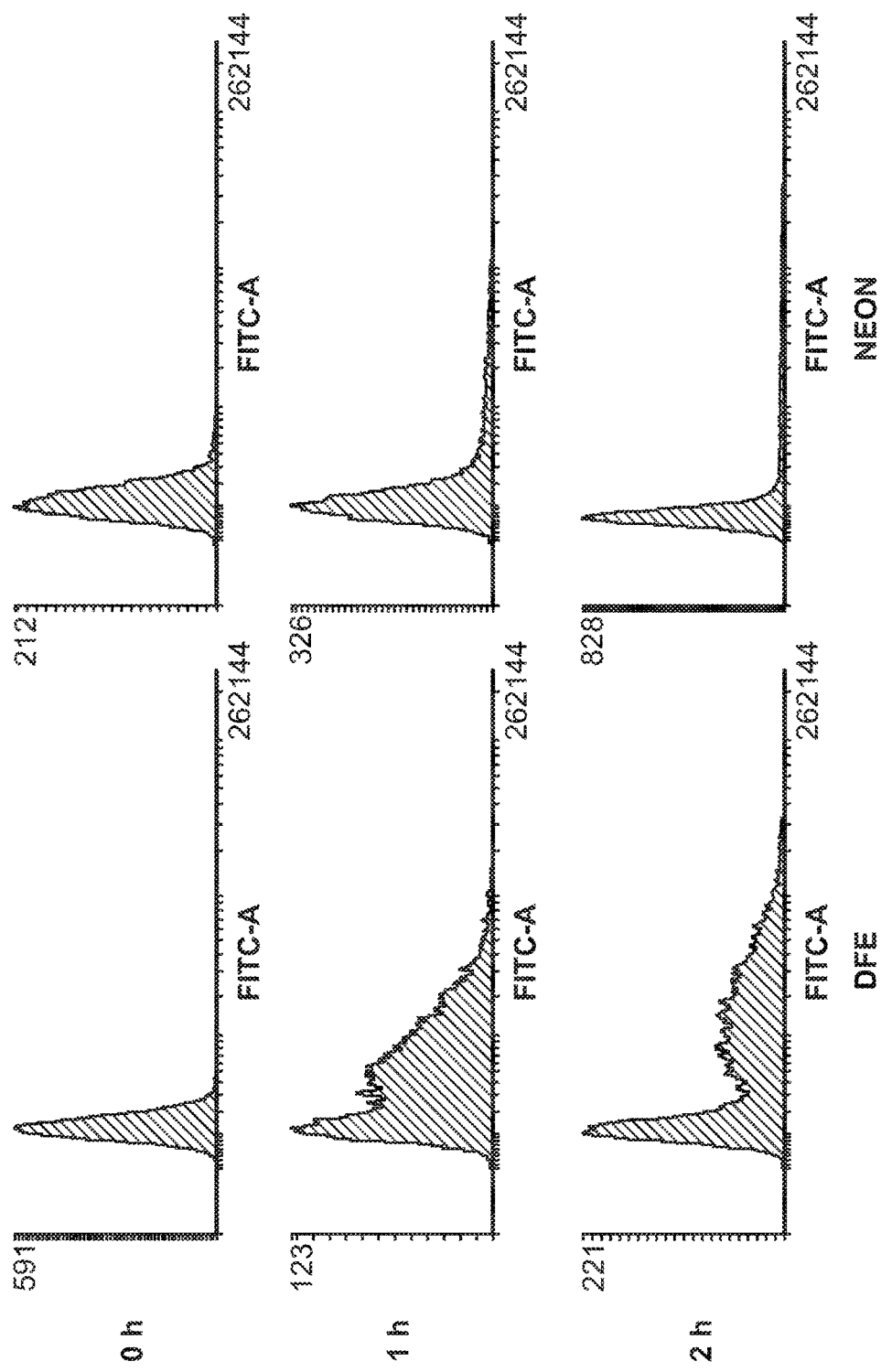
FIGS. 16A-16B are histograms that show the GFP fluorescence intensity distribution at different time post treatment using DFE and NEON (BEP). The GFP fluorescence intensity distribution of HeLa cells was shown in the histogram measured by flow cytometry at different time point post treatment. The results indicate that in DFE DNA transcription occurs instantly after delivery while in BEP the intracellular transportation of DNA requires a few hours. Cells start to express GFP immediately after DFE treatment while in electroporation, it takes more than 4 hours to transcribe DNA after treatment. The mean fluorescence intensity for DFE also appeared to be higher than for BEP. The histogram of expressing cells is shifted more to the right for DFE than for NEON, which indicates higher protein expression even at 24 hours.
Figure 16B:
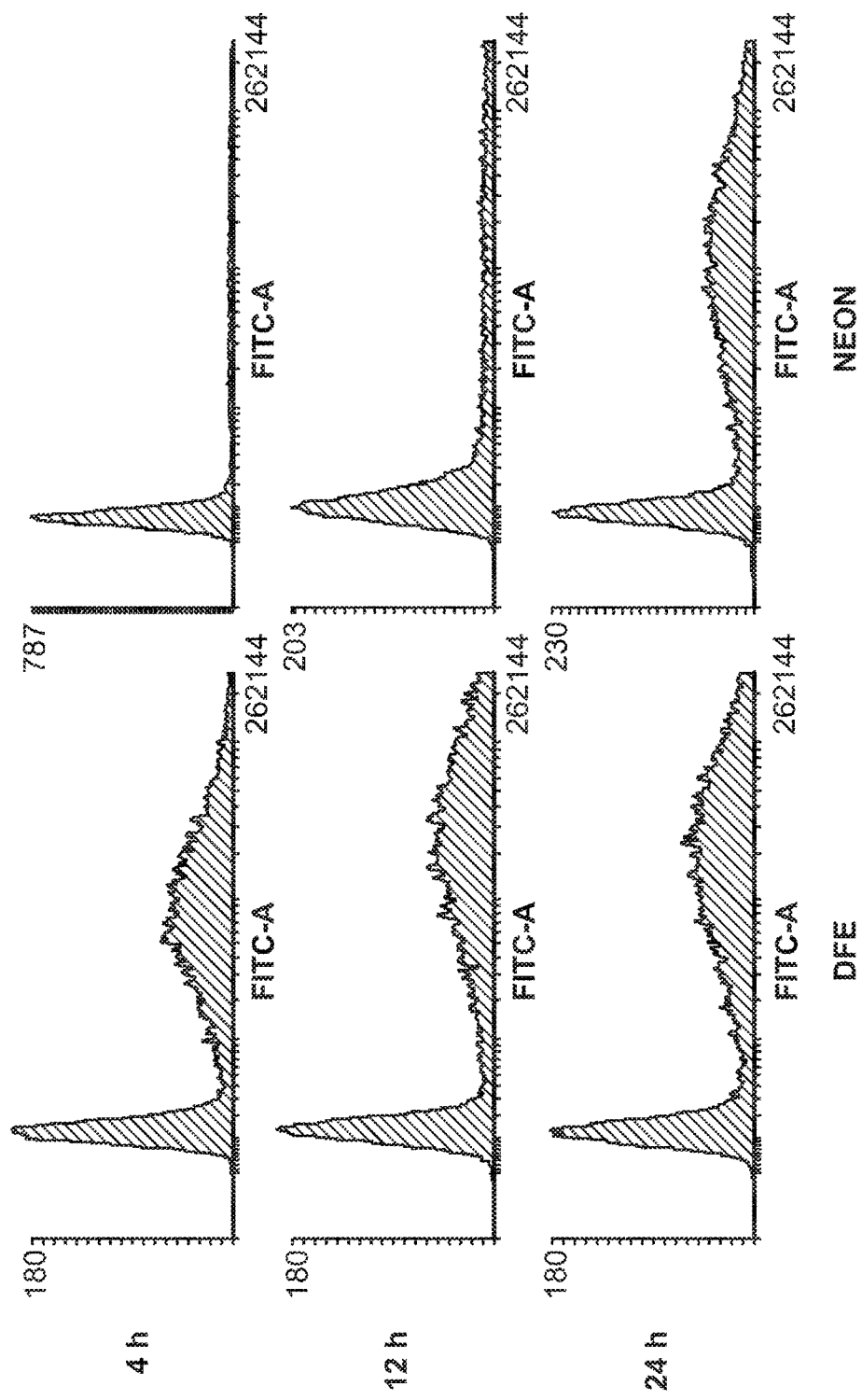
Figure 17:
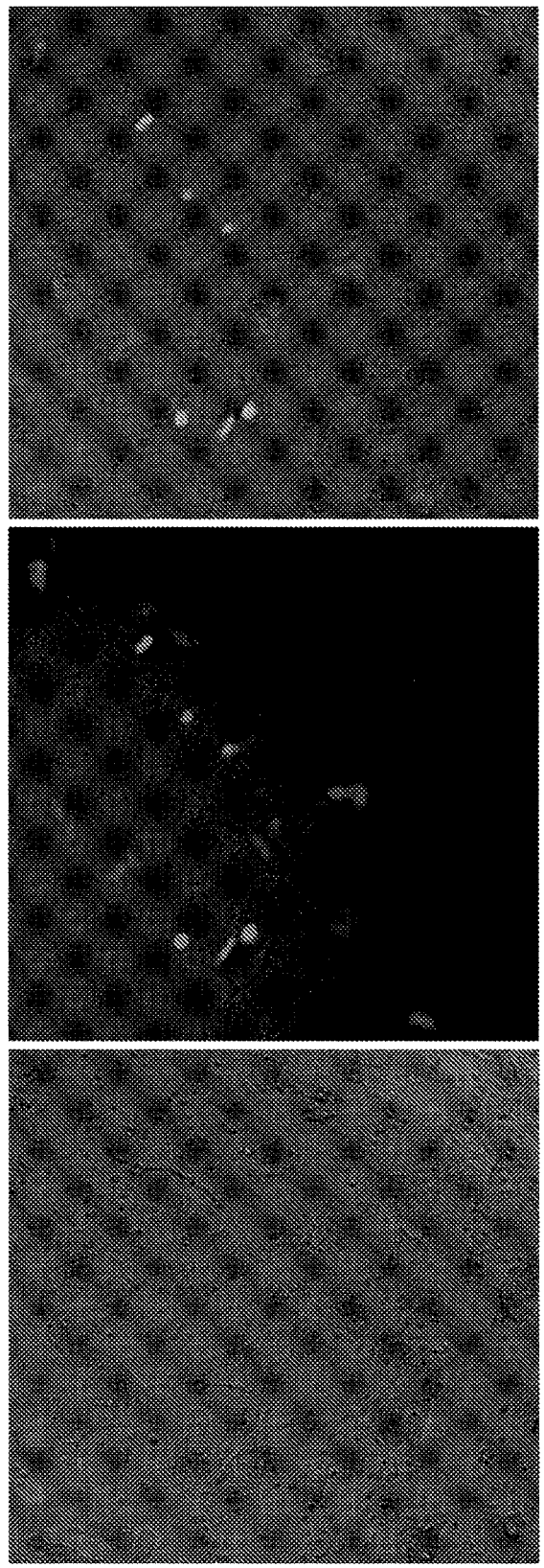
FIG. 17 shows GFP DNA Expression of mESC after 24 h. Fluorescence microscopy image shows the GFP expression in mouse embryonic stem cells (mESC) 24 hours after DFE delivery of GFP DNA plasmid.
Figure 18:
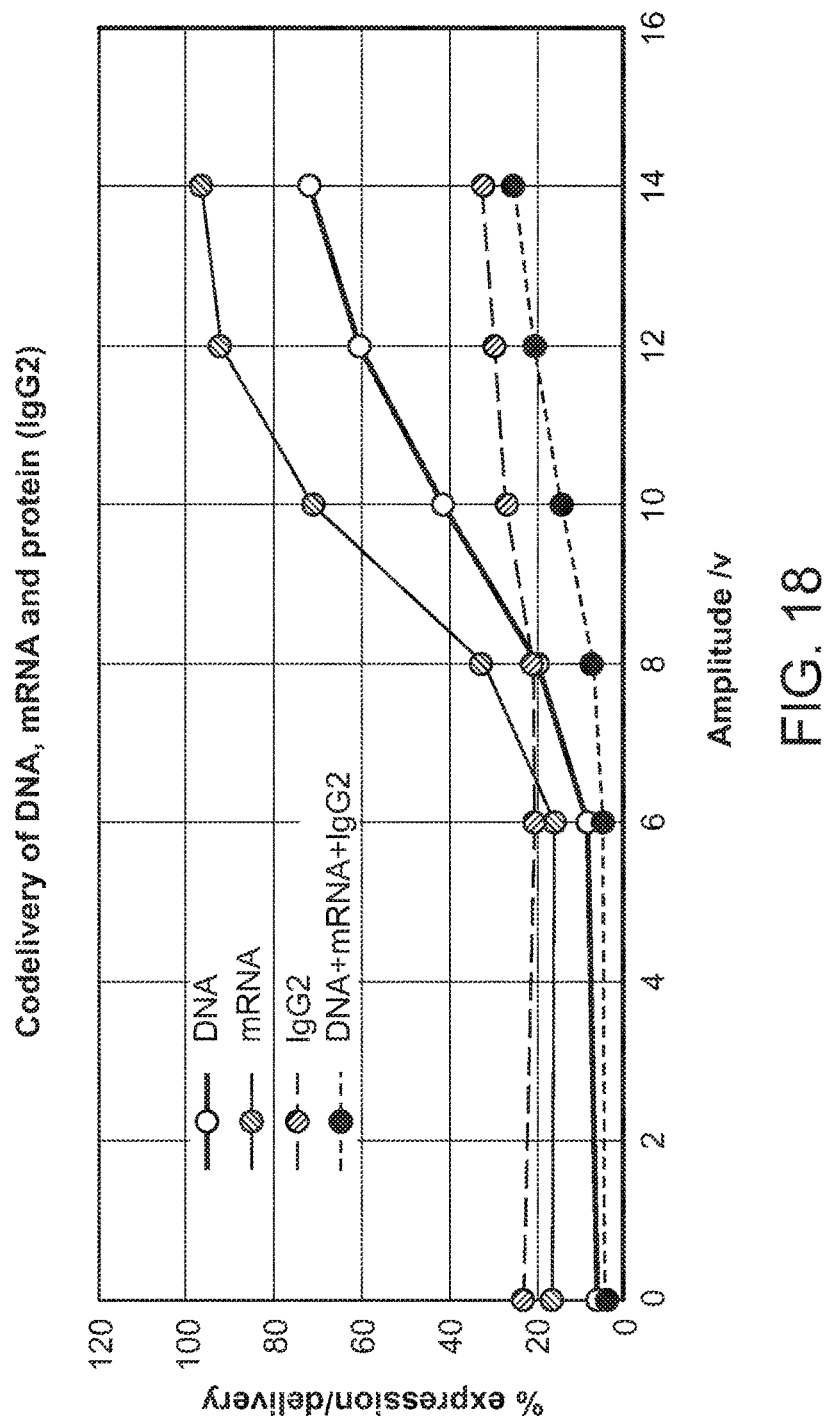
FIG. 18 is a line graph illustrating codelivery of DNA, mRNA and protein (IgG2) into cells. This figure shows the delivery efficiency of each material at different amplitudes when codelivered. The y-axis is % expression/delivery. So for mRNA and DNA it is % expression while for IgG2 it is % delivery.
Figure 19:
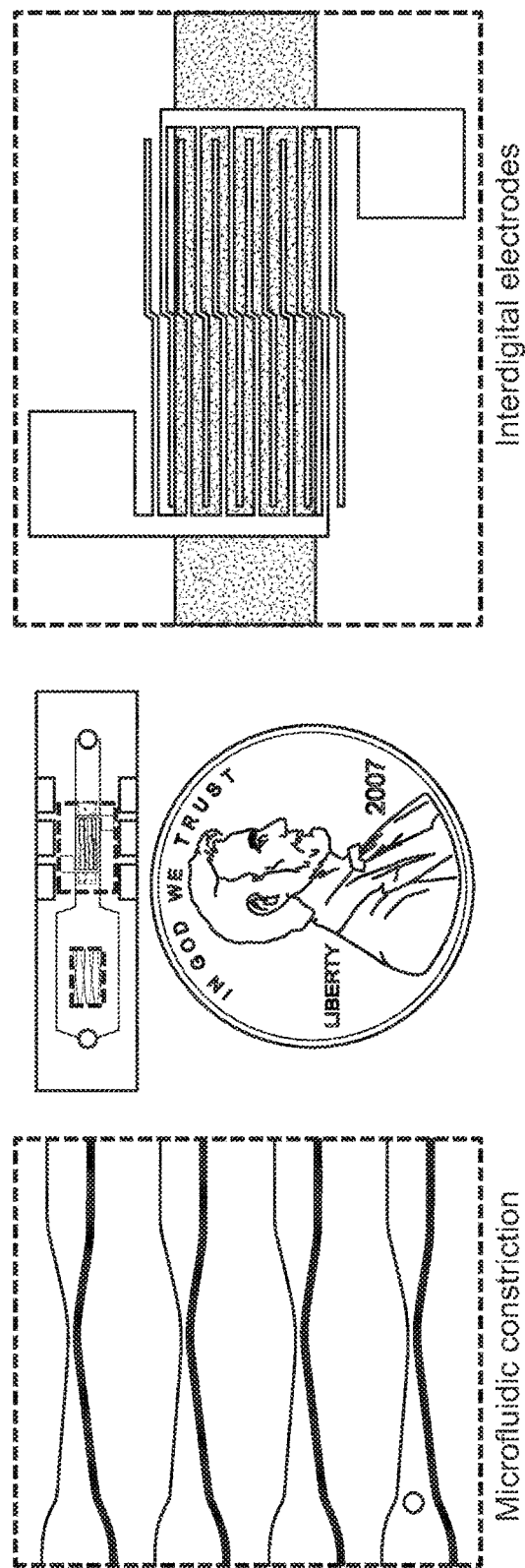
FIG. 19 illustrates an exemplary device of the invention.
Figure 20:
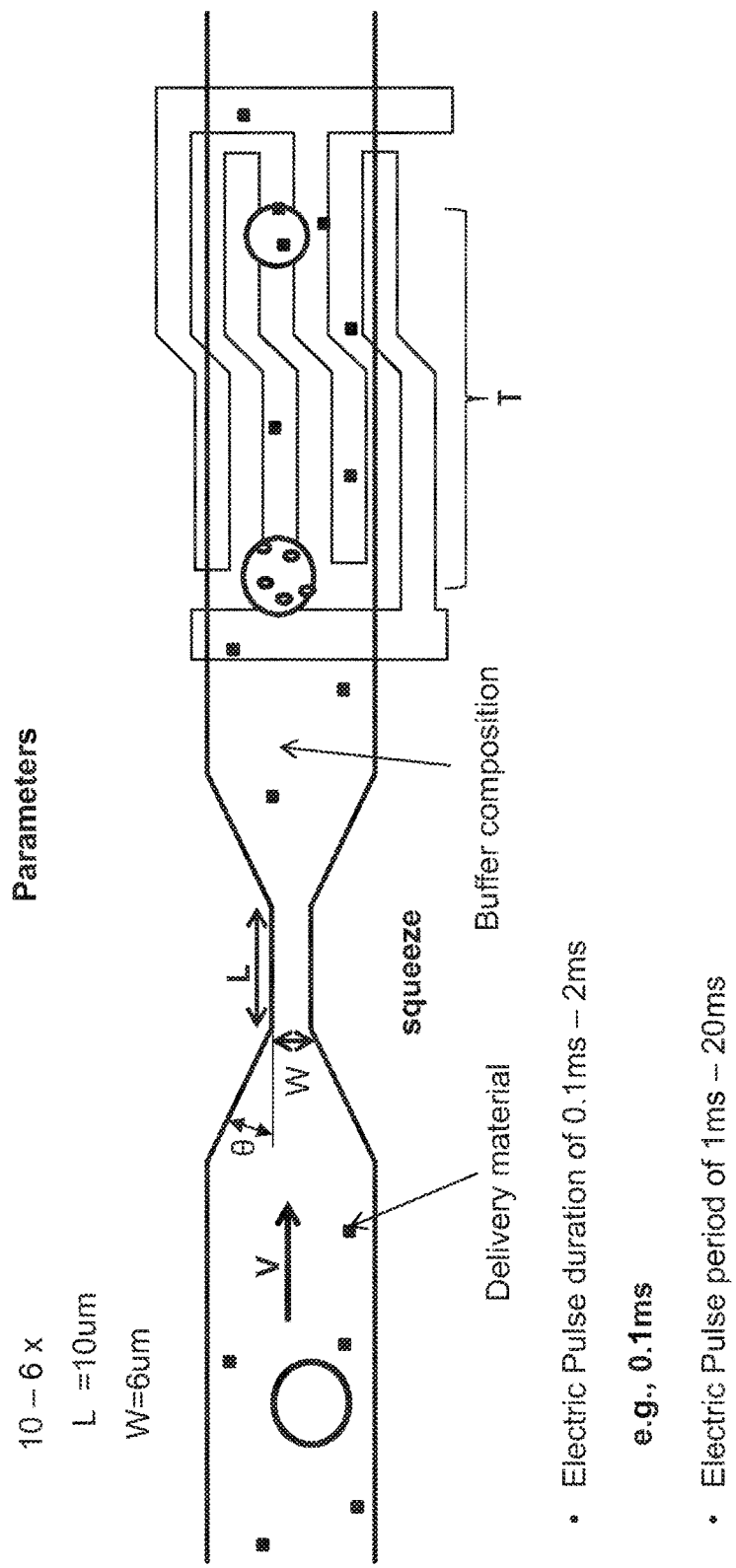
FIG. 20 is a cartoon with non-limiting examples of device parameters.

To further investigate the mechanism of DFE delivery, a comparative study was carried out on the ability to transfect HeLa cells with GFP plasmid DNA using DFE and other four widely used DNA transfection techniques: microinjection, lipofectonnine 2000, ME (microfluidic (without squeeze)+electric field) and BEP (bulk electroporation, using NEON electroporation system, a common commercial electroporation tool). GFP expression was analyzed using flow cytometry after treatment with each technique, as shown in FIG. 11. BEP and ME showed a similar expression kinetics as GFP was gradually expressed within the first 24 hours after treatment. 70% of the transfected cells expressed GFP between 4-48 hours. In microinjection and DFE, however, more than 80% of the GFP-expressing cells (the cells that express GFP fluorescence after 48 hours) had measurable expression within the first hour post treatment, indicating that DNA transcription/translation occurred soon after treatment. The remaining 20% ultimately GFP expressing cells (the cells that expressed GFP after 48 hours) had detectable expression 1 to 4 hours post treatment. Microinjection is broadly accepted as a means of facilitating direct injection of materials into the nucleus. The fact that microinjection and DFE share similar DNA expression kinetics is strong evidence that DNA delivered by DFE was immediately accessible for transcription in the nucleus. By contrast, in the lipofection (Lipofectamine 2000) case, minimal GFP fluorescence was found in the first 4 hours post treatment, and more than 95% of transfected cells expressed GFP between 4-48 h after treatment. Fluorescence images of GFP expressed cells by DFE, BEP, and Lipofection are shown in FIG. 15. To better understand the mechanism of DFE, the fluorescence intensity of expressed GFP in the HeLa cells was compared statistically, as shown in FIGS. 16A-16B. In BEP, the migration to nucleus and subsequent transcription required many hours, and GFP fluorescence was increasing throughout the whole 24 hours. The fluorescence intensity of the majority of the transfected cells started to increase right after treatment and become saturated within 6 hours, indicating that the DNA transcription occurred from a similar starting time point when DNA was delivered into the nucleus.

To further explore the working mechanism of DNA transfer, the distribution of DNA was directly visualized at the single cell level using CY3 labeled plasmid DNA. Cells were first incubated with DAPI and Cell Mask green plasma membrane stain for nucleus and membrane staining, and then mixed with labeled DNA right before treatment of DFE, BEP, and mechanical disruption. After treatment, cells were incubated in culture medium for 2 minutes and then fixed using a cell fixation kit. Optical measurements were carried out using a Nikon A1R confocal microscope. When an electric pulse of 15 ms/1200V, known to permeabilize cells, was applied, a sharp CY3 fluorescence appeared at the plasma membrane level, indicating the absorption and accumulation of DNA on the membrane. This result was consistent with previous studies that demonstrate asymmetric embedding of DNA into the plasma membrane. In mechanical disruption, little or no fluorescence of labeled DNA was detected in the cytoplasm with the confocal microscope although previous studies based on flow cytometry have demonstrated some delivery of labeled DNA. In DFE, labeled DNA fluorescence was found to be distributed in the cytoplasm, nucleus, and plasma membrane. Interestingly, the DNA in the plasma membrane was distributed in a bipolar manner relative to BEP's unipolar profile—potentially indicating the route of labelled DNA entry and exit from the cell during its exposure to the electric field. The direct visualization of DNA in the cytoplasm and nucleus further indicates that DFE is capable of more effective delivery of DNA directly to the nucleus. Such results demonstrate that DFE provides a more powerful means of facilitating efficient delivery of functional materials to the cytosol, nucleus and other subcellular organelles inside a cell.

Intracellular delivery is a challenging process that plays an important role in a diversity of applications. Liposome and nanoparticle based methods have difficulty translating to primary cells or non-nucleic acids, electroporation has toxicity issues and can be ineffective for macromolecules that are not highly charged, and mechanical disruption methods can struggle to provide adequate nuclear delivery. The DFE combines the efficacy of mechanical membrane disruption with the driving force of a field—thus maintaining the robust delivery capabilities of mechanical disruption while enhancing nuclear delivery of charged cargo such as nucleic acids, e.g., plasmids.

DNA transport from the plasma membrane to the nucleus and subsequent transcription is a complicated, most likely active, process that can take hours and may vary dramatically among different cell types. This process is essential in electroporation and carrier-based methods such as Lipofection, and is thought to hinder the DNA transfection of hard-to-transfer cells such as immune cells and stem cells. The data described herein demonstrate that DFE delivers DNA directly into the cytoplasm and nucleus by coupling mechanical disruption and an electric field. Cells were first passed through microchannels with constriction to generate perturbations on the plasma membrane. Without wishing to be bound by any scientific theory, the results indicate that a following exposure to an electric field drives surrounding DNA into the cytoplasm and nucleus. HeLa cells, GFP plasmid DNA, and Cy3 fluorescence labeled plasmid DNA were used to investigate and examine the working mechanism of DFE at the single cell level and the statistical level. This is the most rapid expression of naked DNA plasmid in a high throughput setting demonstrated without carrier assistance. The visualization of DNA transfer process using different techniques was compared. The DNA expression dynamics of Lipofection in FIG. 10 shows that DNA transfer to the nucleus and subsequent transcription can require over 4 hours in HeLa cells. DNA expression with conventional electroporation was slightly faster. There is ongoing debate regarding how DNA migrates into the nucleus during the electroporation process. Some believe that electric pulse permeabilizes the cell membrane and electrophoresis drives DNA directly into the nucleus, while others observe that DNA first form aggregates at electropermeabilized areas of the plasma membrane and then migrates toward the nucleus through a biologically active process. In the BEP results described in this example, 20% of transfected cells express GFP within the first hour and 80% express throughout the next 20 hours. This could be an indication that both of the aforementioned mechanisms occurred in BEP. The small portion of cells that express GFP immediately after treatment may have direct electrophoresis of DNA into the nucleus while the majority of cells that express GFP after 4 hours, like Lipofection, must transport the DNA to the nucleus for expression.

The DFE delivery paradigm combines membrane disruption and field effects to achieve greater efficacy, e.g., a synergistic effect, compared to any individual technique. Electroporation can address DNA transfection for many cell types but has limitations in delivering some materials, such as proteins, and could be toxic. The mechanical disruption techniques, such as squeezing, have shown significant success in delivery of a variety of materials, including proteins and nanomaterials, to a diversity of cell types with minimal toxicity. However, they have had limited success with DNA presumably due to ineffective nuclear delivery. By combining mechanical disruption and electric field effects, DFE has demonstrated better, e.g., synergistic outcomes for DNA expression and is capable of delivering proteins, milestones that are difficult to accomplish with any of the aforementioned methods individually.

Device Fabrication and Experimental Setup

A silicon wafer was bonded to a Pyrex wafer to form the DFE microfluidic device. Two major steps were involved in the fabrication: (1) the fabrication of microfluidic channels on silicon wafer, and (2) the fabrication of microfluidic electrodes on Pyrex wafer. The device was mounted onto a holder with inlet and outlet reservoirs. Electric pulses were generated from a function generators (Agilent E4422B) and gained through an amplifier to drive the device through the wire bonded to the electrode pads using conductive epoxy. Solutions of cells, mixed with desired delivery material (cargo compounds or compositions), are placed in the inlet reservoir. This reservoir is then connected to a compressed air line controlled by a regulator. A pressure (0-20 psi) is used to drive the fluid through the device, at the same time, electric pulses are applied to the device when cells pass through. Cells are collected from outlet reservoir subjected to further treatment.

As indicated above, two major steps were involved in the fabrication of the microfluidic device (FIG. 13): (1) the fabrication of electrodes on Pyrex wafer, and (2) the fabrication of microfluidic channel on silicon wafer. FIG. 13 (*a-d*) shows the process of electrodes. A layer of photoresist (SPR3012, MicroChem, Newton, Mass.) was spin-coated on a 6 inch Pyrex wafer, patterned with a UV light source, and developed in a photoresist developer (MF CD-26, Microposit). A double-layer metal (Ti/Pt, 50 Å/500 Å) was subsequently deposited on the wafer using an e-beam evaporator (Semicore Corp), followed by a lift-off process to remove the photoresist and form the electrodes and pads. Two steps of photolithography were involved to fabricate silicon microfluidic channels, as shown in FIG. 13 (*e-h*). The silicon wafer was first patterned by photoresist (Shipley 1827, MicroChem, Newton, Mass.) and etched by a Deep Reactive Ion Etching (DRIE, Adixen, Hingham, Mass.). A second photolithography and DRIE were applied to etch through the silicon wafer to form the inlet and outlet for the microfluidic device.

Finally, silicon layer was sealed with Pyrex layer using anodic bonding at 300 and 800 V, and diced into separate chip with a dimension of 6×23 mm$^2$. The final device is shown in FIG. 9B. The width of electrode finger and spacing gap of device used in our setup are 40 μm and 60 μm, respectively. The height of the microfluidic channel in silicon substrate is 20 μm.

Cell Culture. HeLa cells were cultured in 75 T flasks containing 20 mL of DMEM culture medium supplemented with 10% fetal bovine serum (FBS, Invitrogen 16000). Cells were seeded into T flasks at 37 C in a humidified atmosphere containing 5% $CO_2$.

Delivery Materials. Fluorescently labeled molecules, including dextran and plasmid DNA, were mixed with cell solution at a concentration of 0.1 mg/mL. GFP DNA plasmid was used to measure the DNA transfection.

Lipofection. Lipofectamine 2000 DNA transfection kit was used to represent Lipofection technique. the DNA-lipid complex was prepared by combining 2 uL of Lipofection 2000 reagent with 1 ug of DNA plasmid in 100 uL of Opti-MEM medium.

Microinjection. The microinjection of DNA plasmid into HeL cells was operated by very experienced and well trained staff at the Massachusetts Institute of Technology. 30 cells were injected for each run. The DNA concentration in the buffer for injection.

OTHER EMBODIMENTS

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

What is claimed is:

1. A method for delivering a compound or composition into a cell, the method comprising:
    providing a cell in a payload-containing cell suspension;
    passing the cell suspension through a microfluidic channel that includes a cell-deforming constriction;
    passing the cell through the constriction such that a pressure is applied to the cell causing perturbations of the cell membrane large enough for the payload to pass through the cell membrane and into the cytosol of the cell; and
    contacting the cell with an electric field,
    wherein the electric field has a strength or pulse strength that is about 0.1-10 kV/cm and a pulse duration of about 50-2000 microseconds.

2. The method of claim 1, wherein the step of contacting the cell with an electric field translocates the payload from a first location in the cell to a second location inside the cell after the payload has entered the cell.

3. The method of claim 1, wherein the cell is contacted with a magnetic field, and the magnetic field is generated by at least one electromagnet.

4. The method of claim 1, wherein the electric field is generated by one or more electrodes.

5. The method of claim 4, wherein the cell is one of a plurality of cells, and each cell is passed through one of a plurality of parallel microfluidic channels, wherein each microfluidic channel of the plurality of parallel microfluidic channels includes a cell-deforming constriction, and wherein the plurality of cells is passed through the electric field.

6. The method of claim 4, wherein the electric field is generated by two electrodes to drive the payload into the cell.

7. The method of claim 4, wherein the electric field is generated by a plurality of electrode pairs in which electrode size varies between electrode pairs.

8. The method of claim 4, wherein at least one of the one or more electrodes is driven by a function generator coupled to the electrode, the function generator driving the electrode to generate the electric field.

9. The method of claim 1, wherein the cell is passed through the microfluidic channel in a first device and then removed from the first device and contacted with the electric field in a second device.

10. The method of claim 1, wherein the microfluidic channel and the electric field are within one device.

11. The method of claim 10, wherein
    (a) the cell passes through the constriction to the field in a continuous flow, wherein after passing through said constriction, the cell contacts or passes through a portion of the electric field; or
    (b) after passing through the constriction the cell flows into and remains within a zone of the device where the cell is contacted with the field.

12. The method of claim 1, wherein the payload comprises one or more of
    (a) a protein;
    (b) a small molecule;
    (c) a sugar;
    (d) polymers of biological, synthetic, organic, or inorganic molecules;
    (e) a charged molecule or composition comprising a charged molecule; or
    (f) an uncharged molecule.

13. The method of claim 1, wherein the payload is driven into one or more of
    (a) the nucleus of the cell;
    (b) a mitochondrion of the cell; or
    (c) an organelle of the cell other than the nucleus or a mitochondrion of the cell.

14. The method of claim 1, wherein
    the diameter of the constriction is about 20-99% of the diameter of the cell passing therethrough.

15. The method of claim 1, wherein the cell is a prokaryotic cell or a eukaryotic cell.

16. The method of claim 1, wherein the diameter of the constriction is about 4 µm, 5 µm, 6 µm, 7 µm, 8 µm, 9 µm, 10 µm, 15 µm, 20 µm, 4 µm-10 µm, or 10 µm-20 µm.

17. The method of claim 1, wherein the length of the constriction is about 10 µm, 15 µm, 20 µm, 24 µm, 30 µm, 40 µm, 50 µm, 60 µm, 10 µm-40 µm, 10 µm-50 µm, or 10 µm-60 µm.

18. The method of claim 1, wherein the cell is contacted with the electric field about 0.0001 s, 0.001 s, 0.002 s, 0.003 s, 0.004 s, 0.005 s, 1 s, 2 s, 3 s, 4 s, 5 s, 6 s, 7 s, 8 s, 9 s, 10 s, 0.001 s-0.005 s, or 0.0001 s-10 s after exiting the cell-deforming constriction, or within about 0.0001 s, 0.001 s, 0.002 s, 0.003 s, 0.004 s, 0.005 s, 1 s, 2 s, 3 s, 4 s, 5 s, 6 s, 7 s, 8 s, 9 s, 10 s, 0.001 s-0.005 s, or 0.0001 s-10 after exiting the cell-deforming constriction.

19. The method of claim 1, wherein the exposure time of the cell to the electric field is about 10 ms-50 ms, 50 ms, 100 ms, or 10 ms-100 ms.

20. The method of claim 1, wherein the electric field is a pulsed direct electric current.

21. The method of claim 1, wherein the electric field is pulsed at about 50 µs-200 µs.

22. The method of claim 1, wherein the pulse strength of the electric field is about 1 kV/cm-3 kV/cm, 0.1 kV/cm-0.5 kV/cm, 0.1 kV/cm-1 kV/cm, 0.1 kV/cm-1.5 kV/cm, 0.1 kV/cm-2 kV/cm, 0.1 kV/cm-2.5 kV/cm, or 0.1 kV/cm-3 kV/cm.

23. The method of claim 1, wherein a pressure of about 10 psi-100 psi is used to pass the solution through the microfluidic channel.

24. The method of claim 1, wherein the cell passes through the microfluidic channel at a speed of about 300 mm/s, 100 mm/s-300 mm/s, 200 mm/s-700 mm/s, 250 mm/s-400 mm/s, 100 mm/s-1000 mm/s, or 1 mm/s-1000 mm/s.

25. The method of claim 1, wherein said microfluidic channel comprises multiple cell-deforming constrictions in series.

26. The method of claim 1, wherein said microfluidic channel comprises a single cell-deforming constriction.

27. The method of claim 1, wherein the cell is one of a plurality of cells, and about 80, 85, 90, 91, 92, 93, 94, 95, 96, 97, 98, 99, 90-95, or 80-100% of the cells are viable after passing through the electric field.

28. The method of claim 25, wherein the electric field is pulsed at a duration of about 0.1 ms, at a period of 1 ms-20 ms, 0.1 ms-2000 ms, or 1-200 ms.

29. The method of claim 1, wherein the cell passes through the electric field at a speed of about 100 mm/s, 170 mm/s, 300 mm/s, 100 mm/s-300 mm/s, 200 mm/s-700 mm/s, 250 mm/s -400 mm/s, 100 mm/s-1000 mm/s, or 1 mm/s-1000 mm/s.

30. The method of claim 1, wherein the perturbations of the cell membrane include a maximum diameter of about 1 nm-20 nm, 1 nm-600 nm, 4 nm, 5 nm, 6 nm, 7 nm, 8 nm, 9 nm, 10 nm, 12 nm, 14 nm, 16 nm, 18 nm, 20 nm, 25 nm, 50 nm, 75 nm, 100 nm, 150 nm, 200 nm, 250 nm, 300 nm, 350 nm, 400 nm, 450 nm, 500 nm, or 600 nm.

31. The method of claim 1, wherein perturbations of the cell membrane having a maximum diameter of about 1 nm-20 nm, 1 nm-600 nm, 4 nm, 5 nm, 6 nm, 7 nm, 8 nm, 9 nm, 10 nm, 12 nm, 14 nm, 16 nm, 18 nm, 20 nm, 25 nm, 50 nm, 75 nm, 100 nm, 150 nm, 200 nm, 250 nm, 300 nm, 350 nm, 400 nm, 450 nm, 500 nm, or 600 nm persist on the cell membrane for at least 1 min, 2 min, 3 min, 4 min, 5 min, 6 min, 7 min, 8 min, 9 min, 10 min, or 1 min-10 min.

\* \* \* \* \*

UNITED STATES PATENT AND TRADEMARK OFFICE
CERTIFICATE OF CORRECTION

PATENT NO. : 10,526,573 B2  
APPLICATION NO. : 15/526517  
DATED : January 7, 2020  
INVENTOR(S) : Xiaoyun Ding et al.

Page 1 of 1

It is certified that error appears in the above-identified patent and that said Letters Patent is hereby corrected as shown below:

In the Specification

At Column 6, Line 35: "about 1°, 50°," should read --about 1°, 5°,--

At Column 6, Line 36: "45°, 50°, 60°," should read --45°, 50°, 55°, 60°,--

At Column 11, Line 50: "electropenneabilized" should read --electropermeabilized--

At Column 12, Line 52: "nano particle delivery" should read --nanoparticle delivery--

At Column 39, Line 51: "lipofectonnine 2000" should read --lipofectamine 2000--

At Column 42, Lines 45-46: "the DNA-lipid complex" should read --The DNA-lipid complex--

In the Claims

At Column 45, Claim 28, Line 7: "The method of claim 25" should read --The method of claim 1--

Signed and Sealed this  
Twentieth Day of October, 2020

Andrei Iancu  
*Director of the United States Patent and Trademark Office*